(12) United States Patent
Lowe et al.

(10) Patent No.: US 8,715,330 B2
(45) Date of Patent: May 6, 2014

(54) TEMPERATURE AND FLOW CONTROL METHODS IN A THERMAL THERAPY DEVICE

(75) Inventors: Mark H. Lowe, Danville, CA (US);
Krister Bowman, Oakland, CA (US);
Joseph Metro, Martinez, CA (US)

(73) Assignee: CoolSystems, Inc., Concord, CA (US)

( * ) Notice: Subject to any disclaimer, the term of this patent is extended or adjusted under 35 U.S.C. 154(b) by 448 days.

(21) Appl. No.: 12/910,772

(22) Filed: Oct. 22, 2010

(65) Prior Publication Data

US 2011/0098793 A1   Apr. 28, 2011

Related U.S. Application Data

(66) Substitute for application No. 61/254,064, filed on Oct. 22, 2009.

(51) Int. Cl.
*A61F 7/00* (2006.01)
(52) U.S. Cl.
USPC .......................................... 607/104; 607/108
(58) Field of Classification Search
USPC .................. 607/104–106, 108–112, 114, 81, 607/85–87; D23/314, 316; 4/675, 678
See application file for complete search history.

(56) References Cited

U.S. PATENT DOCUMENTS

| | | |
|---|---|---|
| 1,958,899 A | 5/1934 | MacAdams |
| 2,146,622 A | 2/1939 | Carlo |
| 2,413,386 A | 12/1946 | Schulz |
| 2,510,125 A | 6/1950 | Meakin |
| 2,531,074 A | 11/1950 | Miller |
| 2,540,547 A | 2/1951 | Rodert |
| 2,608,690 A | 9/1952 | Kolb et al. |
| 2,703,770 A | 3/1955 | Melzer |
| 2,726,658 A | 12/1955 | Chessey |
| 2,954,898 A | 10/1960 | Feeberg |
| 3,261,042 A | 7/1966 | Baker |
| 3,320,682 A | 5/1967 | Sliman |
| 3,354,898 A | 11/1967 | Barnes |
| 3,561,435 A | 2/1971 | Nicholson |
| 3,738,367 A | 6/1973 | Hardy |
| 3,744,555 A | 7/1973 | Fletcher et al. |
| 3,830,676 A | 8/1974 | Elkins |
| 3,871,381 A | 3/1975 | Roslonski |

(Continued)

FOREIGN PATENT DOCUMENTS

| | | |
|---|---|---|
| CN | 201001805 | 1/2008 |
| EP | 0412708 A1 | 2/1991 |

(Continued)

OTHER PUBLICATIONS

Lowe et al.; U.S. Appl. No. 12/982,266 entitled "Reinforced therapeutic wrap and method," filed Dec. 30, 2010.

(Continued)

*Primary Examiner* — Linda Dvorak
*Assistant Examiner* — Adam Avigan
(74) *Attorney, Agent, or Firm* — Shay Glenn LLP

(57) ABSTRACT

A controlled temperature therapy system has a pump, a reservoir, and a therapy component. The reservoir has an inlet in communication with the therapy component and an outlet in communication with the pump. The reservoir may also include a baffle adjacent the outlet. The inlet may be a movable inlet, a nozzle or include a flow directing surface.

34 Claims, 56 Drawing Sheets

(56) References Cited

U.S. PATENT DOCUMENTS

| | | |
|---|---|---|
| 3,901,225 A | 8/1975 | Sconce |
| 3,993,053 A | 11/1976 | Grossan |
| 4,020,209 A | 4/1977 | Yuan |
| 4,026,299 A | 5/1977 | Sauder |
| 4,116,476 A | 9/1978 | Porter et al. |
| 4,118,946 A | 10/1978 | Tubin |
| 4,147,921 A | 4/1979 | Walter et al. |
| 4,149,529 A | 4/1979 | Copeland et al. |
| 4,149,541 A | 4/1979 | Gammons et al. |
| 4,170,998 A | 10/1979 | Sauder |
| 4,194,247 A | 3/1980 | Melander |
| 4,335,726 A | 6/1982 | Kolstedt |
| 4,338,944 A | 7/1982 | Arkans |
| 4,412,648 A | 11/1983 | Ford et al. |
| 4,436,125 A | 3/1984 | Blenkush |
| 4,460,085 A | 7/1984 | Jantzen |
| 4,471,759 A | 9/1984 | Anderson et al. |
| 4,478,436 A | 10/1984 | Hashimoto |
| 4,547,906 A | 10/1985 | Nishida |
| 4,550,828 A | 11/1985 | Baldwin et al. |
| 4,597,384 A | 7/1986 | Whitney |
| 4,678,027 A | 7/1987 | Shirey et al. |
| 4,691,762 A | 9/1987 | Elkins et al. |
| 4,699,613 A | 10/1987 | Donawick et al. |
| 4,718,429 A | 1/1988 | Smidt |
| 4,738,119 A | 4/1988 | Zafred |
| 4,753,268 A | 6/1988 | Palau |
| 4,765,338 A | 8/1988 | Turner et al. |
| 4,844,072 A | 7/1989 | French et al. |
| 4,884,304 A | 12/1989 | Elkins |
| 4,925,603 A | 5/1990 | Nambu |
| 4,955,435 A | 9/1990 | Shuster et al. |
| 4,964,282 A | 10/1990 | Wagner |
| 4,964,402 A | 10/1990 | Grim et al. |
| 4,976,262 A | 12/1990 | Palmacci |
| 5,002,270 A | 3/1991 | Shine |
| 5,014,695 A | 5/1991 | Benak et al. |
| 5,022,109 A | 6/1991 | Pekar |
| 5,033,136 A | 7/1991 | Elkins |
| 5,052,725 A | 10/1991 | Meyer et al. |
| 5,056,563 A | 10/1991 | Glossop |
| 5,072,875 A | 12/1991 | Zacoi |
| 5,074,285 A | 12/1991 | Wright |
| 5,076,068 A | 12/1991 | Mikhail |
| 5,080,089 A | 1/1992 | Mason et al. |
| 5,080,166 A | 1/1992 | Haugeneder |
| 5,086,771 A | 2/1992 | Molloy |
| 5,097,829 A | 3/1992 | Quisenberry |
| 5,104,158 A | 4/1992 | Meyer et al. |
| 5,113,877 A | 5/1992 | Johnson, Jr. et al. |
| 5,163,425 A | 11/1992 | Nambu et al. |
| 5,163,923 A | 11/1992 | Donawick et al. |
| 5,172,689 A | 12/1992 | Wright |
| 5,201,552 A | 4/1993 | Hohmann et al. |
| 5,230,335 A | 7/1993 | Johnson, Jr. et al. |
| 5,241,951 A | 9/1993 | Mason et al. |
| 5,243,706 A | 9/1993 | Frim et al. |
| 5,245,221 A | 9/1993 | Schmidt et al. |
| 5,269,369 A | 12/1993 | Faghri |
| 5,294,156 A | 3/1994 | Kumazaki et al. |
| 5,305,712 A | 4/1994 | Goldstein |
| 5,314,455 A | 5/1994 | Johnson, Jr. et al. |
| 5,316,547 A | 5/1994 | Gildersleeve |
| 5,336,249 A | 8/1994 | Mahawili |
| 5,353,605 A | 10/1994 | Naaman |
| 5,354,101 A | 10/1994 | Anderson, Jr. |
| 5,354,103 A | 10/1994 | Torrence et al. |
| 5,383,689 A | 1/1995 | Wolfe, Sr. |
| RE34,883 E | 3/1995 | Grim |
| 5,395,399 A | 3/1995 | Rosenwald |
| 5,407,421 A | 4/1995 | Goldsmith |
| 5,411,541 A | 5/1995 | Bell et al. |
| 5,415,625 A | 5/1995 | Cassford et al. |
| 5,417,720 A | 5/1995 | Mason |
| 5,427,577 A | 6/1995 | Picchietti et al. |
| 5,441,533 A | 8/1995 | Johnson et al. |
| 5,449,379 A | 9/1995 | Hadtke |
| 5,451,201 A | 9/1995 | Prengler |
| 5,466,250 A | 11/1995 | Johnson, Jr. et al. |
| 5,470,353 A | 11/1995 | Jensen |
| 5,476,489 A | 12/1995 | Koewler |
| 5,484,448 A | 1/1996 | Steele et al. |
| 5,486,207 A | 1/1996 | Mahawili |
| 5,494,074 A | 2/1996 | Ramacier, Jr. et al. |
| 5,496,358 A | 3/1996 | Rosenwald |
| 5,520,622 A | 5/1996 | Bastyr et al. |
| 5,524,293 A | 6/1996 | Kung |
| 5,527,268 A | 6/1996 | Gildersleeve et al. |
| 5,533,354 A | 7/1996 | Pirkle |
| 5,539,934 A | 7/1996 | Ponder |
| 5,553,712 A | 9/1996 | Tisbo et al. |
| 5,554,119 A | 9/1996 | Harrison et al. |
| 5,556,138 A | 9/1996 | Nakajima et al. |
| 5,564,124 A | 10/1996 | Elsherif et al. |
| 5,630,328 A | 5/1997 | Hise et al. |
| 5,638,707 A | 6/1997 | Gould |
| 5,645,671 A | 7/1997 | Tillinghast |
| 5,647,051 A | 7/1997 | Neer |
| D382,113 S | 8/1997 | DuRapau |
| 5,662,239 A | 9/1997 | Heuvelman |
| 5,662,695 A | 9/1997 | Mason et al. |
| 5,683,118 A | 11/1997 | Slocum |
| 5,728,058 A | 3/1998 | Ouellette et al. |
| 5,732,464 A | 3/1998 | Lamont |
| 5,792,216 A | 8/1998 | Kappel |
| 5,806,335 A | 9/1998 | Herbert et al. |
| 5,833,638 A | 11/1998 | Nelson |
| 5,862,675 A | 1/1999 | Scaringe et al. |
| 5,865,841 A | 2/1999 | Kolen et al. |
| 5,866,219 A | 2/1999 | McClure et al. |
| 5,868,690 A | 2/1999 | Eischen, Sr. |
| 5,895,418 A | 4/1999 | Saringer |
| 5,913,885 A | 6/1999 | Klatz et al. |
| 5,920,934 A | 7/1999 | Hannagan et al. |
| 5,933,002 A | 8/1999 | Jacobsen et al. |
| 5,948,012 A | 9/1999 | Mahaffey et al. |
| 5,951,598 A | 9/1999 | Bishay et al. |
| 5,967,225 A | 10/1999 | Jenkins |
| 5,968,072 A | 10/1999 | Hite et al. |
| 5,970,519 A | 10/1999 | Weber |
| 5,980,561 A | 11/1999 | Kolen et al. |
| 5,984,885 A | 11/1999 | Gaylord, Jr. et al. |
| 5,989,285 A | 11/1999 | DeVilbiss et al. |
| 5,992,459 A | 11/1999 | Sugita et al. |
| 6,030,412 A | 2/2000 | Klatz et al. |
| 6,036,107 A | 3/2000 | Aspen et al. |
| 6,036,718 A | 3/2000 | Ledford et al. |
| 6,048,326 A | 4/2000 | Davis et al. |
| 6,053,169 A | 4/2000 | Hunt |
| 6,055,670 A | 5/2000 | Parker |
| 6,074,413 A | 6/2000 | Davis et al. |
| 6,083,256 A | 7/2000 | Der Ovanesian |
| 6,086,609 A | 7/2000 | Buckley |
| 6,105,382 A | 8/2000 | Reason |
| 6,109,338 A | 8/2000 | Butzer |
| 6,117,164 A | 9/2000 | Gildersleeve et al. |
| 6,146,413 A | 11/2000 | Harman |
| 6,156,059 A | 12/2000 | Olofsson |
| 6,176,869 B1 | 1/2001 | Mason et al. |
| 6,261,314 B1 | 7/2001 | Rich |
| 6,306,112 B2 | 10/2001 | Bird |
| 6,328,276 B1 | 12/2001 | Falch et al. |
| 6,352,550 B1 | 3/2002 | Gildersleeve et al. |
| 6,354,635 B1 | 3/2002 | Dyson et al. |
| 6,361,514 B1 | 3/2002 | Brown et al. |
| 6,368,357 B1 | 4/2002 | Schon et al. |
| 6,371,976 B1 | 4/2002 | Vrzalik et al. |
| 6,382,678 B1 | 5/2002 | Field et al. |
| 6,440,159 B1 | 8/2002 | Edwards et al. |
| 6,443,498 B1 | 9/2002 | Liao |
| 6,508,831 B1 | 1/2003 | Kushnir |
| 6,547,284 B2 | 4/2003 | Rose et al. |
| 6,551,347 B1 | 4/2003 | Elkins |
| 6,551,348 B1 | 4/2003 | Blalock et al. |

(56) References Cited

U.S. PATENT DOCUMENTS

| | | |
|---|---|---|
| 6,620,187 B2 | 9/2003 | Carson et al. |
| 6,641,601 B1 | 11/2003 | Augustine et al. |
| 6,645,232 B2 | 11/2003 | Carson |
| 6,660,027 B2 | 12/2003 | Gruszecki et al. |
| 6,699,267 B2 | 3/2004 | Voorhees et al. |
| 6,818,012 B2 | 11/2004 | Ellingboe |
| 6,823,682 B1 | 11/2004 | Jenkins et al. |
| 6,926,311 B2 | 8/2005 | Chang et al. |
| 6,942,015 B1 | 9/2005 | Jenkins |
| 6,962,600 B2 | 11/2005 | Lennox et al. |
| 7,008,445 B2 | 3/2006 | Lennox |
| 7,060,086 B2 | 6/2006 | Wilson et al. |
| 7,125,417 B2 | 10/2006 | Mizrahi |
| 7,141,131 B2 | 11/2006 | Foxen et al. |
| 7,156,054 B1 | 1/2007 | York |
| 7,306,568 B2 | 12/2007 | Diana |
| 7,434,844 B2 | 10/2008 | Kao |
| 7,448,653 B2 | 11/2008 | Jensen et al. |
| 7,490,620 B2 | 2/2009 | Tesluk et al. |
| 7,871,427 B2 | 1/2011 | Dunbar et al. |
| 7,914,563 B2 | 3/2011 | Mason et al. |
| 8,512,263 B2 | 8/2013 | Gammons |
| 2002/0041621 A1 | 4/2002 | Faries et al. |
| 2002/0082668 A1 | 6/2002 | Ingman |
| 2002/0093189 A1 | 7/2002 | Krupa |
| 2002/0108279 A1 | 8/2002 | Hubbard et al. |
| 2003/0060761 A1 | 3/2003 | Evans et al. |
| 2003/0199818 A1 | 10/2003 | Waldhauser et al. |
| 2004/0068309 A1* | 4/2004 | Edelman .................. 607/104 |
| 2004/0158303 A1 | 8/2004 | Lennox et al. |
| 2004/0225341 A1 | 11/2004 | Schock et al. |
| 2005/0136213 A1 | 6/2005 | Seth et al. |
| 2005/0143796 A1 | 6/2005 | Augustine et al. |
| 2005/0143797 A1 | 6/2005 | Parish et al. |
| 2006/0190062 A1 | 8/2006 | Worthen |
| 2006/0200057 A1 | 9/2006 | Sterling |
| 2007/0118194 A1 | 5/2007 | Mason et al. |
| 2007/0161932 A1 | 7/2007 | Pick et al. |
| 2007/0161933 A1 | 7/2007 | Ravikumar |
| 2007/0191918 A1 | 8/2007 | MacHold et al. |
| 2007/0282230 A1 | 12/2007 | Valderrabano et al. |
| 2008/0000474 A1 | 1/2008 | Jochle et al. |
| 2008/0058911 A1 | 3/2008 | Parish et al. |
| 2008/0060374 A1* | 3/2008 | Gammons et al. ........... 62/259.3 |
| 2008/0065172 A1 | 3/2008 | Magdych |
| 2008/0067095 A1 | 3/2008 | Mueller |
| 2008/0234788 A1 | 9/2008 | Wasowski |
| 2008/0275534 A1 | 11/2008 | Noel |
| 2008/0283426 A1 | 11/2008 | Primer et al. |
| 2009/0038195 A1 | 2/2009 | Riker et al. |
| 2009/0183410 A1 | 7/2009 | Tursso et al. |
| 2010/0006631 A1 | 1/2010 | Edwards et al. |
| 2010/0076531 A1 | 3/2010 | Beran et al. |
| 2010/0089896 A1 | 4/2010 | Bart |
| 2010/0161013 A1 | 6/2010 | Heaton |
| 2011/0087142 A1 | 4/2011 | Ravikumar et al. |
| 2011/0152983 A1 | 6/2011 | Schirrmacher et al. |
| 2011/0307038 A1 | 12/2011 | Stiehr |

FOREIGN PATENT DOCUMENTS

| | | |
|---|---|---|
| EP | 0535830 A1 | 4/1993 |
| EP | 1393751 A1 | 3/2004 |
| EP | 1972312 A2 | 9/2008 |
| IT | 330552 | 10/1935 |
| JP | 2000288007 A | 10/2000 |
| KR | 20-0153967 | 8/1999 |
| KR | 100654317 B1 | 12/2006 |
| WO | WO2005/082301 A1 | 9/2005 |
| WO | WO2006/110405 A2 | 10/2006 |

OTHER PUBLICATIONS

Lowe, U.S. App. No. 13/441,761 entitled "System for Providing Treatment to a Mammal and Method," filed Apr. 6, 2012.

Lowe, U.S. Appl. No. 13/441,767 entitled "Control Unit for a Therapy System and Method ," filed Apr. 6, 2012.

Lowe, U.S. App. No. 13/441,770 entitled "Thermal Therapy System," filed Apr. 6, 2012.

Lowe et al.; U.S. Appl. No. 13/525,701 entitled "Adjustable Patient Therapy Device," filed Jun. 18, 2012.

* cited by examiner

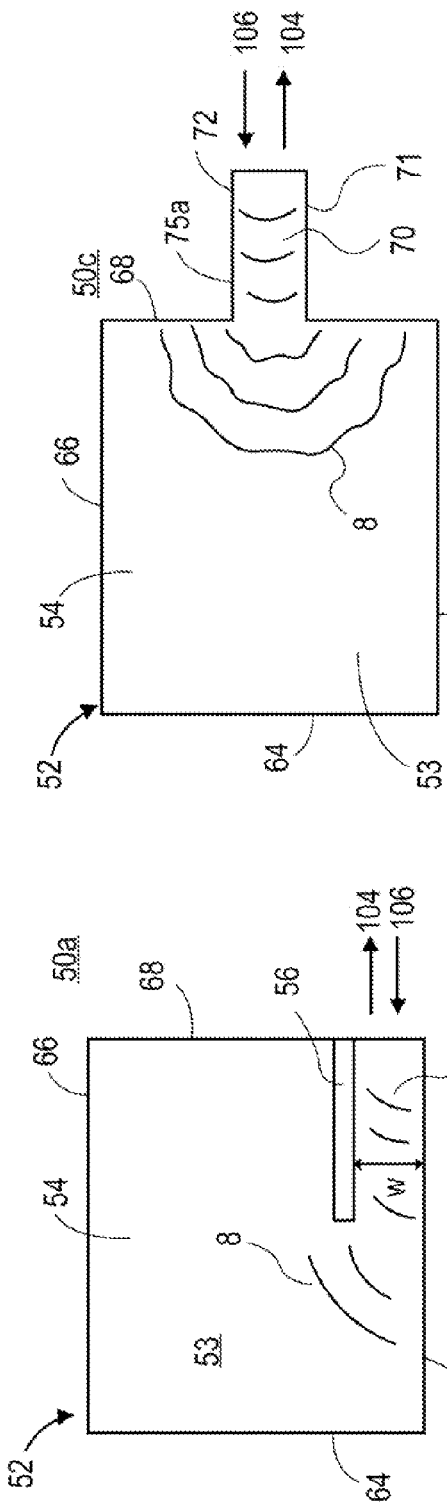
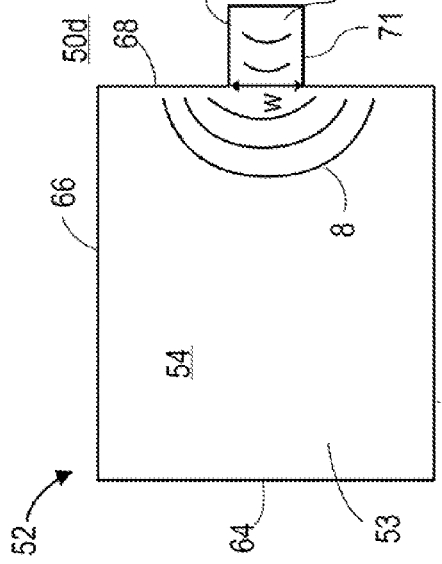
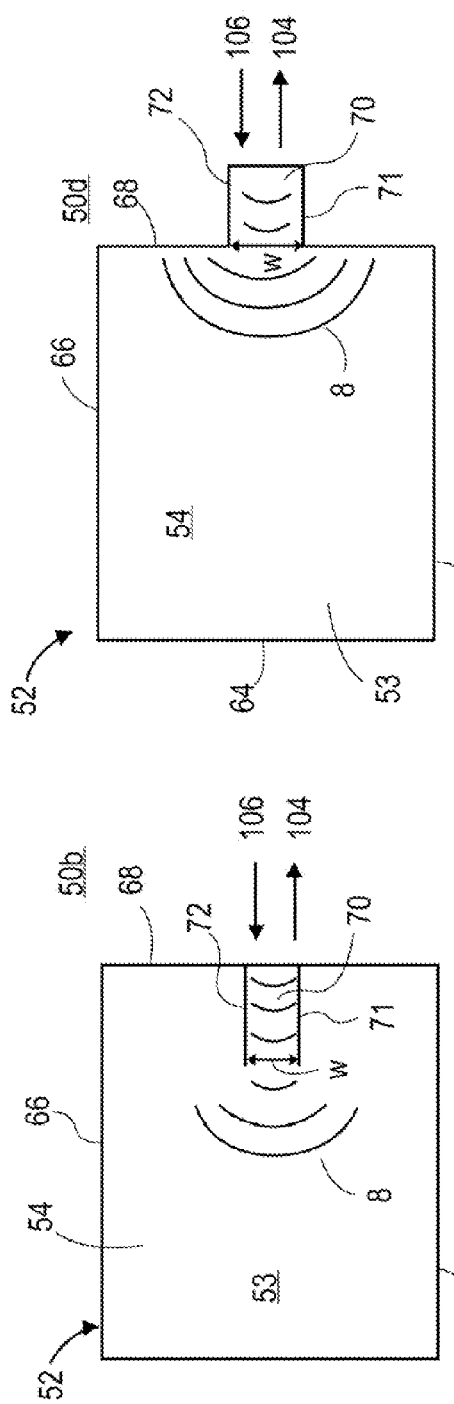

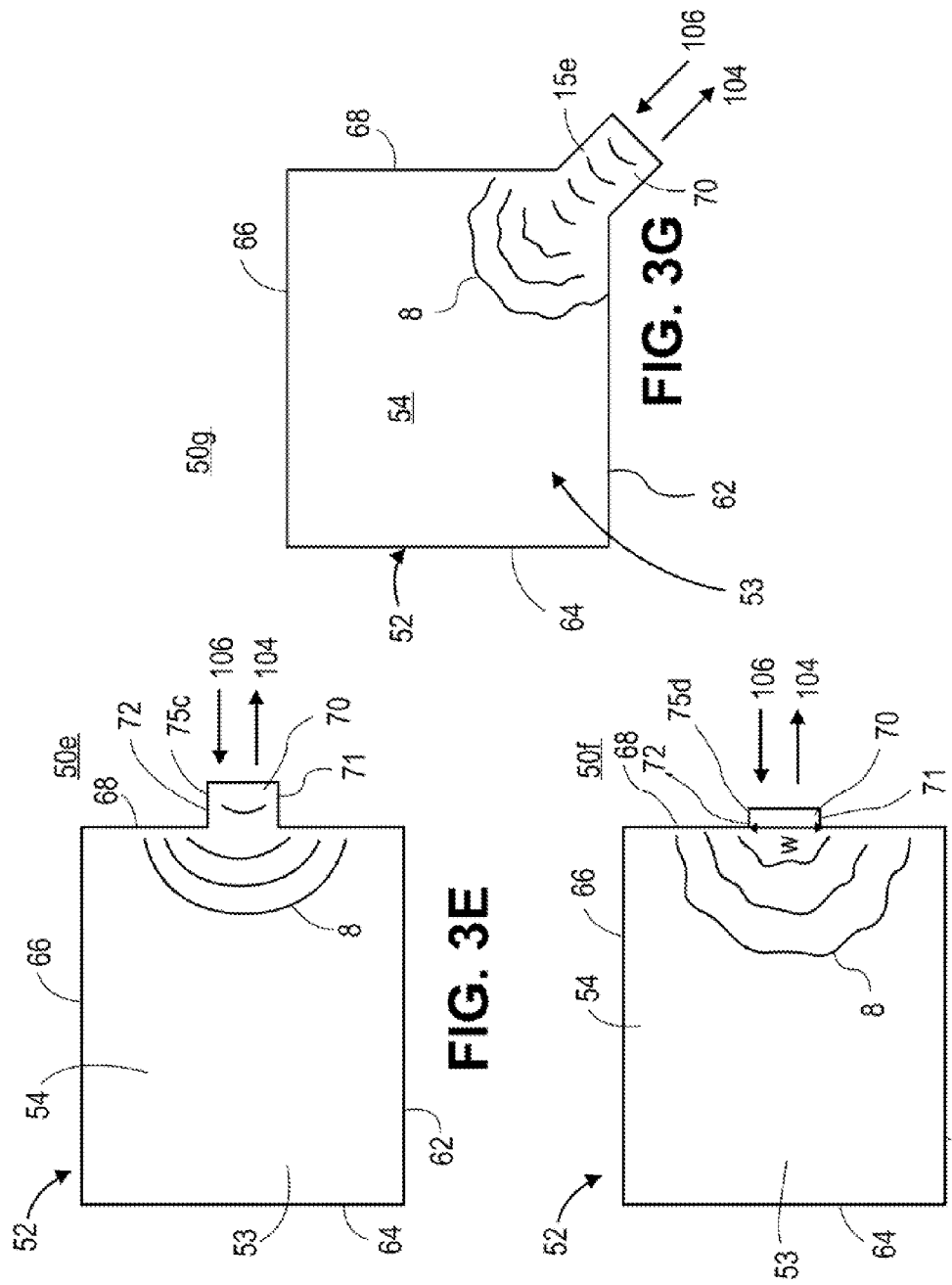

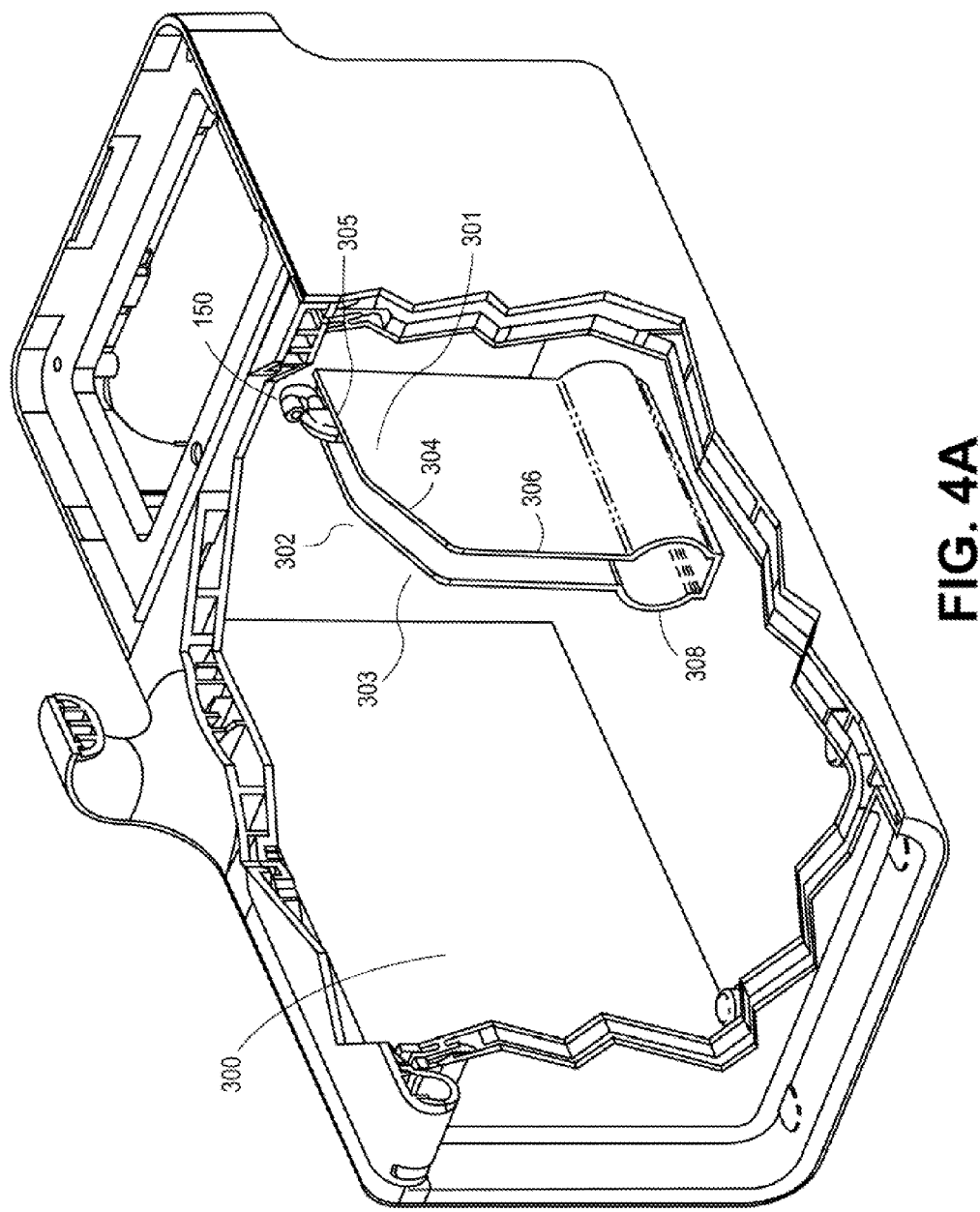

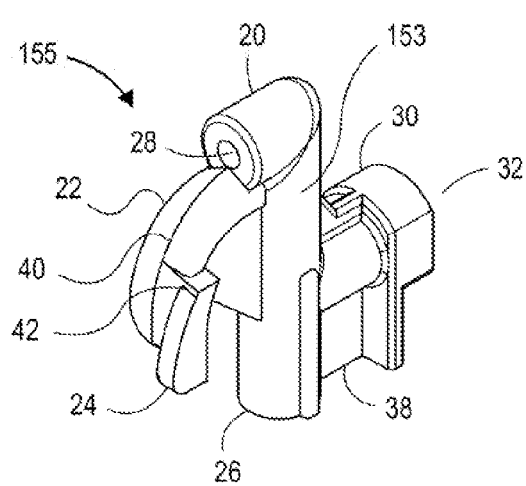
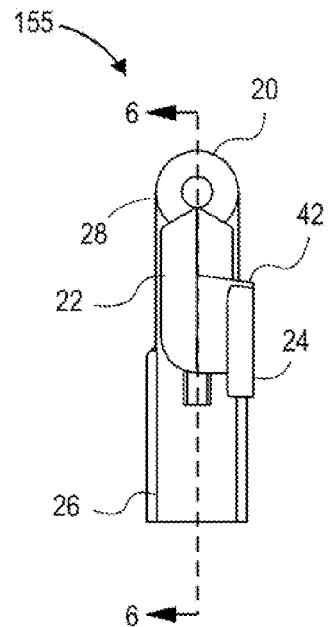
FIG. 7       FIG. 8
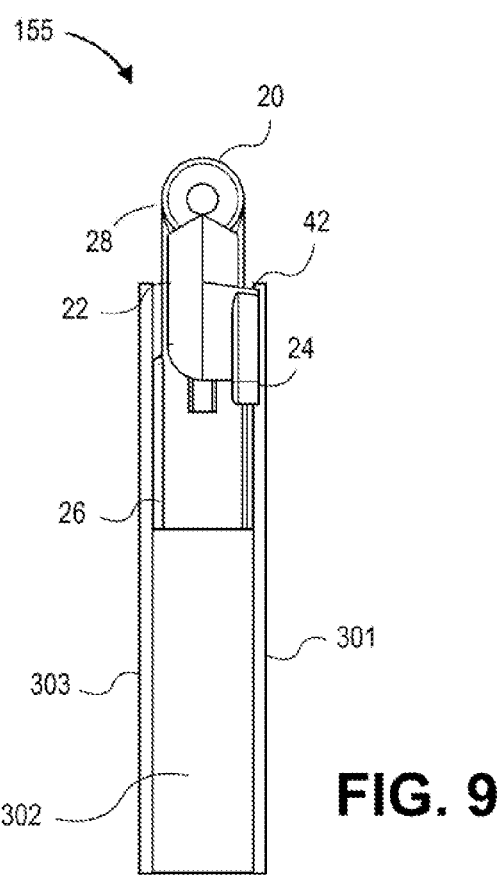
FIG. 9

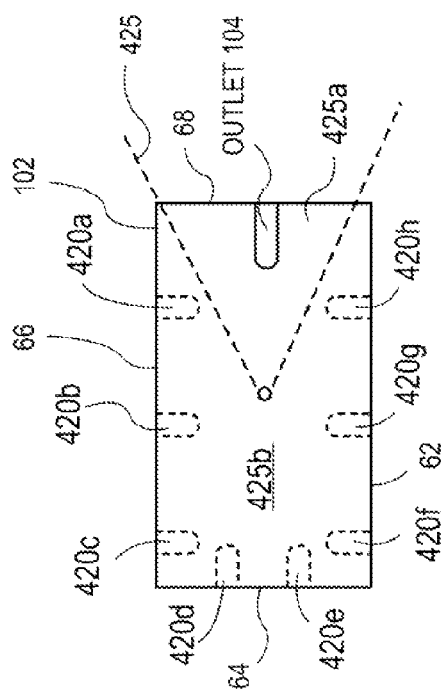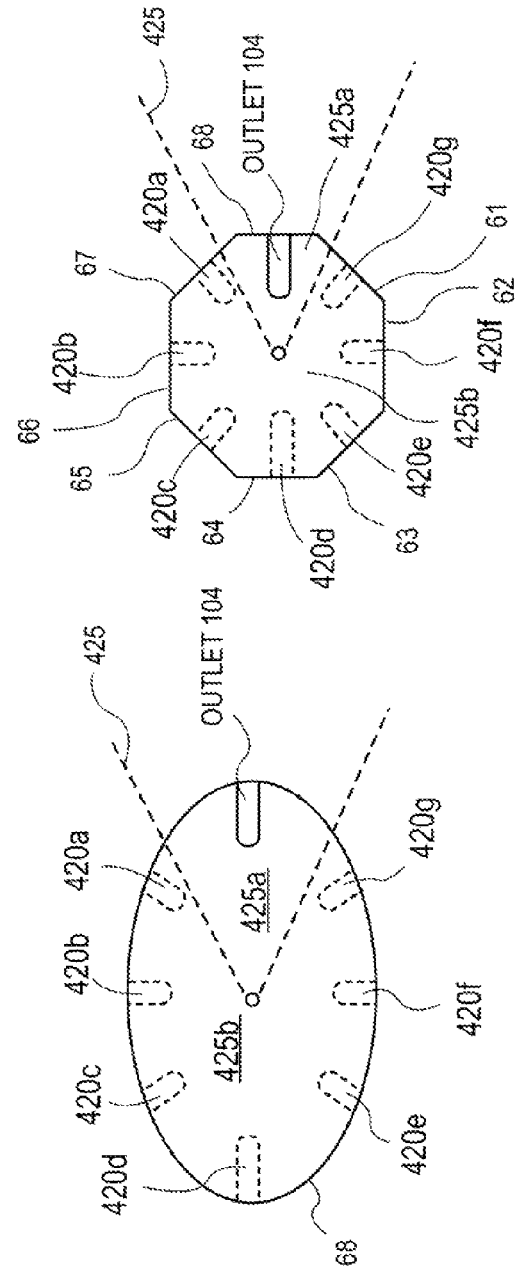

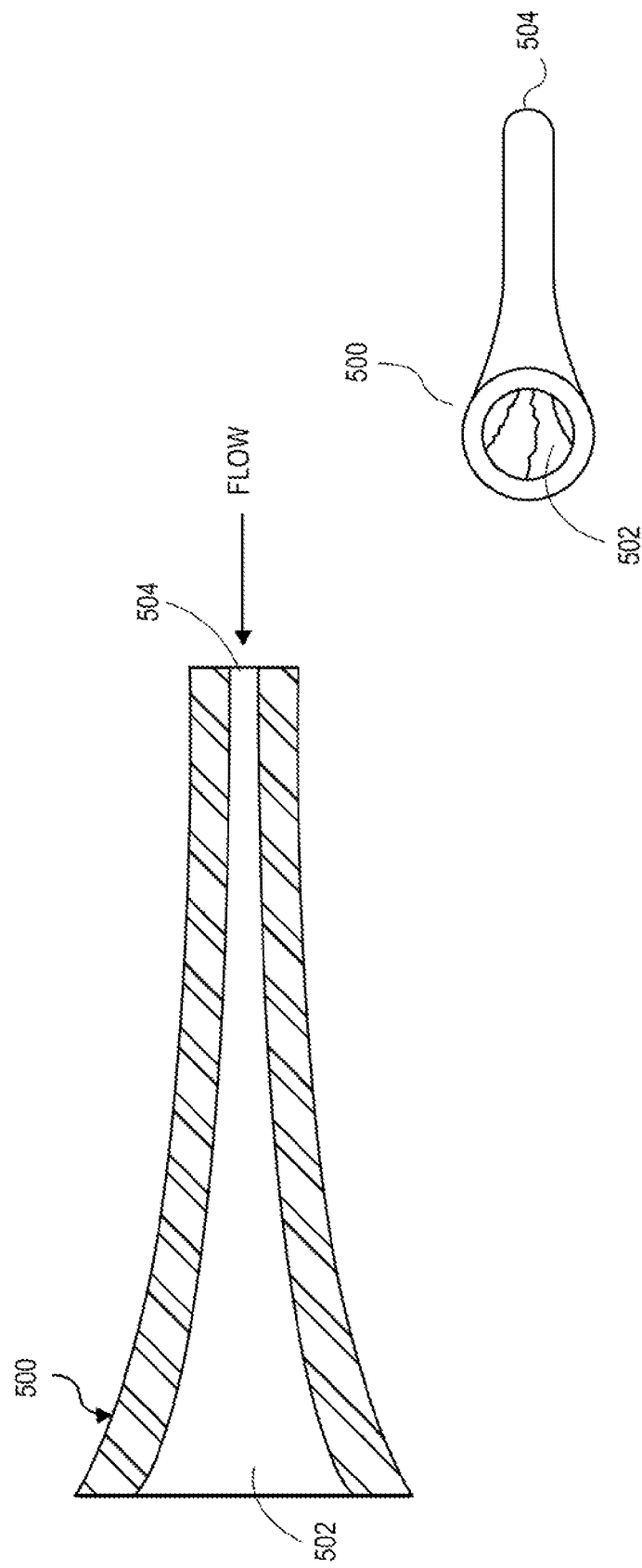

SECTION A-A

TEMPERATURE AND FLOW CONTROL METHODS IN A THERMAL THERAPY DEVICE

CROSS REFERENCE TO RELATED APPLICATIONS

This application claims priority to U.S. Provisional Application No. 61/254,064 filed on Oct. 22, 2009, entitled, "TEMPERATURE AND FLOW CONTROL METHODS IN A THERMAL THERAPY DEVICE."

FIELD OF THE INVENTION

The present invention relates generally to thermal therapy systems.

BACKGROUND OF THE INVENTION

A typical thermal therapy device comprises a control unit with a thermal fluid reservoir, a pump, a return line, fluid lines serving a thermal therapy pad (herein referred to as a "wrap") that makes contact with the skin (either directly or indirectly) of a patient. There is a need for additional capabilities in adjusting the system temperature for a variety of reasons, including patient comfort and safety. Described herein are a number of improvements in both temperature and flow control as well as reservoir improvements that contribute individually or collectively to improved systems and methods for controlled thermal therapy.

SUMMARY OF THE INVENTION

Performance of the thermal therapy device is improved by adjusting the flow rate and temperature of the thermal therapy device.

One aspect of the invention helps to create temperature gradients in the reservoir to encourage fluid leaving the reservoir outlet side to have warmer temperatures when warmer wrap temperatures are desired. A diffuser may be used to slow the velocity of the return fluid in order to minimize turbulence and subsequent mixing in the reservoir.

Another aspect of the invention is to provide a reservoir comprising a nozzle coupled to the reservoir inlet. The nozzle is configured to optimize flow returning from the wrap to the reservoir. The nozzle allows return fluid to land proximal to the reservoir outlet in low and medium flow rates, and far from the inlet at higher flow rates. The performance of the thermal therapy device may be improved by providing return stream vector control with a moving return nozzle directing the return stream in the direction of the reservoir outlet. Performance of the thermal therapy device may also be improved by providing a return stream vector control with a diverter valve Another aspect of the invention improves the performance of the thermal therapy device with the addition of a baffle or a partial wall to the reservoir. The baffle may be a pair of walls generally parallel and with minimal spacing in between the walls. The baffle extends far enough into the reservoir fluid so as to prevent ice from gathering close to the reservoir outlet. The baffle is further configured to allow fluid to flow from the nozzle into the baffle region of the reservoir. Another aspect of the invention is a filter assembly configured to be inserted inside the filter receptacle of the baffle. Through the use of nozzles and baffles, temperature gradients within the reservoir can be effectively set up when desired.

Another aspect of the invention improves the performance of the thermal therapy device by providing robust mixing methods for cold temperatures. One such robust mixing method is to return the water far away from the inlet. Another robust mixing method directs a return stream to push ice towards reservoir outlet. Another mixing method comprises an agitator or impeller to stir the reservoir fluid.

Another aspect of the invention provides a set point control system in a thermal therapy device. The flow rate may be controlled through the control system by using a closed feedback loop based on temperature of the wrap or fluid leaving the control unit.

In one aspect of the present invention, there is a reservoir for a controlled temperature therapy system having a pump and a therapy component. The reservoir includes a container with an interior defined by a floor and at least one wall; an inlet in fluid communication with the interior and in fluid communication with the therapy component; an outlet in fluid communication with the interior and in fluid communication with the pump; and a baffle created by a first wall and a second wall within the interior such that the outlet is between the first wall and the second wall and the spacing between the first and second walls is less than the width of the interior adjacent the inlet.

In another aspect, there is a temperature controlled therapy system having a reservoir; an outlet in the reservoir; a therapy wrap having an inlet and an outlet; a pump having an inlet in communication with the reservoir outlet and an outlet in communication with the therapy wrap inlet; an inlet in communication with the therapy wrap outlet, the inlet having an opening directed towards an interior of the reservoir; and a movable structure connected to the inlet to cause movement of the inlet to alter the orientation of the opening within the interior of the reservoir.

In another aspect, there is a temperature controlled therapy system having a reservoir; an outlet in the reservoir; a therapy wrap having an inlet and an outlet; a pump having an inlet in communication with the reservoir outlet and an outlet in communication with the therapy wrap inlet; a valve in communication with the therapy wrap outlet; a first inlet in the reservoir in communication with the valve and positioned to direct flow from the first inlet into the reservoir; and a second inlet in the reservoir in communication with the valve.

In another aspect, there is a temperature controlled therapy system having a reservoir; an outlet in the reservoir; a therapy wrap having an inlet and an outlet; a pump having an inlet in communication with the reservoir outlet and an outlet in communication with the therapy wrap inlet; a valve in communication with the therapy wrap outlet; an inlet in the reservoir in communication with the valve and positioned to direct flow from the inlet into the reservoir; and a movable inlet in the reservoir in communication with the valve, the movable inlet connected to a movable structure that moves the movable inlet.

In another aspect, there is provided a temperature controlled therapy system, having a reservoir; an outlet in the reservoir; a therapy wrap having an inlet and an outlet; a pump having an inlet in communication with the reservoir outlet and an outlet in communication with the therapy wrap inlet; an inlet in communication with the therapy wrap outlet, the inlet having an opening directed towards an interior of the reservoir; and a flow control surface adjacent the opening wherein fluid moving from a proximal end to a distal end of the flow control surface is directed towards the outlet.

In alternative embodiments, an aspect of the invention may also include one of the first wall and the second wall is provided by a wall of the interior, or where the first wall and the second wall are joined to form a baffle assembly, or the baffle is contained within a recess formed in the wall penetrated by the outlet. In other alternatives, the outlet is in fluid communication with the interior through a penetration in the at least one wall at a location closer to the floor than the inlet or the spacing between the first and second walls is less than the width of a wall penetrated by both the inlet and the outlet. The baffle assembly is formed as part of the container in some embodiments, or the baffle assembly is an insert attached to the interior. In one alternative, the inlet is spaced at a distance from the floor so that in use the inlet is above the level of the heat transfer fluid used in the reservoir.

In still other alternatives, an aspect of the invention may also include a movable inlet configured to alter the orientation of the inlet opening relative to the interior. In additional or alternative configurations, the movable inlet alters the orientation of the inlet opening relative to the interior by operation of an actuator, by operation of a pivoting mechanism, by operation of a rotating mechanism, by operation of a pull wire, or by operation of a shape memory alloy element. In still other aspects, an inlet may have an opening shaped to produce a spray pattern, such as a flat, conical or jet pattern.

In still other alternatives, an aspect of the invention may also include a filter within the reservoir. The filter may be provided over the outlet. In addition, the filter may be a filter cartridge having a housing shaped to fit between the first wall and the second wall to align a filter within the cartridge over the outlet and a filter within the cartridge or a filter material between the first wall and the second wall and adjacent to the outlet.

In still other alternatives, an aspect of the invention may include an actuator. The actuator may have any of a number of configurations such as a linkage connected proximal to the distal portion of the inlet and to a control located outside of the reservoir, a shape memory alloy element extending along the inlet and connected a controller located outside of the reservoir, or the shape memory alloy element extending along the inlet is disposed within a wall of the inlet. In still other alternatives, there is a flow directing surface extending beyond an opening of the inlet, wherein the shape memory alloy element extending along the inlet is disposed within or along the flow directing surface. Alternatively, actuation of the shape memory alloy element causes the flow directing surface to be directed towards the outlet, to be directed away from the outlet or to provide a response of the shape memory alloy element when actuated produces an adjustable bending angle on the flow directing surface or where the adjustable bending angle on the flow directing surface provides for a range of flow directing surface positions from a first direction towards an outlet and a second direction towards a structure within a reservoir. The structure within a reservoir is a wall of the reservoir or a portion of a baffle. The baffle may also include a dividing wall positioned relative to the first wall and the second wall.

In still other alternatives, an aspect of the invention may include a pivoting structure connected to the inlet to alter the direction of a flow exiting the inlet. The pivoting structure is connected to the inlet to alter the direction of a flow exiting the inlet about a generally vertical axis of the container. The pivoting structure is connected to the inlet to alter the direction of a flow exiting the inlet about a generally horizontal axis of the container. The pivoting structure is connected to the inlet to alter the direction of a flow exiting the inlet generally between the first wall and the second wall. The pivoting structure is connected to the inlet to alter the direction of a flow exiting the inlet generally between the first wall and the second wall and then across the first wall or across the second wall.

In still other alternatives, an aspect of the invention may also include a tongue adjacent to the inlet and extending towards the container floor. The tongue may have a surface adjacent the inlet with a concave shape, a surface adjacent the inlet with a convex shape, a surface adjacent the inlet with a u-shaped profile, a u-shaped profile extending along a ridge extending from a point adjacent the inlet towards the distal portion of the tongue, a surface adjacent the inlet with a v-shaped profile. In other alternatives, there is a ridge along the tongue surface adjacent the inlet and extending towards the interior, the ridge remains generally along the central portion of the tongue between the first wall and the second wall, or the ridge position begins in a central portion of the tongue near the inlet and then moves towards the first wall or the second wall in the proximal portion of the tongue. In still other alternatives, there is a directing structure adjacent the distal portion of the tongue shaped to direct flow along the directing structure towards the first wall or the second wall. In another aspect, the tongue outer surface having an overall curvature from a proximal end adjacent the inlet to a distal end wherein the overall curvature of the tongue outer surface controls the trajectory of a fluid flowing from the outlet to remain on the outer surface.

In one alternative, the inlet includes a nozzle. Various alternatives include: a pivot point on the proximal portion of the nozzle that permits the movement of the distal tip of the nozzle, the movement of the distal tip is generally parallel to the floor of the container, the movement of the nozzle directs a fluid flow over the first wall or the second wall, the movement of the nozzle distal tip is generally parallel to a wall joined to the wall penetrated by the inlet, the movement of the nozzle distal tip is generally between a position that directs flow from the nozzle towards the floor or a wall unconnected to the wall penetrated by the inlet.

In still other alternatives, there is a handle connected to the nozzle such that rotation of the handle produces rotation of the nozzle about the pivot point. There may also be a motor connected to the nozzle such that rotation of the motor produces rotation of the nozzle about the pivot point with a computer controller in communication with the motor and providing control signals to move the nozzle in response to a feedback signal.

In still other embodiments, there is a second inlet penetrating a wall of the container; and a valve having an inlet in communication with the therapy component and an outlet in communication with the inlet and the second inlet. In one aspect, operation of the valve adjusts the relative amounts of flow between the inlet and the second inlet. The inlet may be directing flow generally downward toward the outlet.

In still other aspects, there is a diffuser within the interior and adjacent the inlet such that a portion of the fluid moving through the inlet moves through the diffuser. The diffuser may be a screen at least partially covering the inlet, a structure at least partially blocking the fluid exiting the inlet from directly entering the interior or a a funnel in communication with the inlet such that the portion of fluid moving through the diffuser is all of the fluid moving through the inlet. In still other alternatives, the reservoir includes an impeller, or an opening in a wall of the reservoir; and an air source connected to the opening.

In still other alternatives, there is a knob connected to the movable structure so that rotation of the knob causes the movement of the inlet to alter the orientation of the opening within the interior of the reservoir or a pivoting structure to move the inlet. In addition, a motor may be attached to the movable structure such that operation of the motor causes the movement of the inlet to alter the orientation of the opening within the interior of the reservoir. There is also a controller that accepts a user input to operate the motor or a system controller in communication with the pump and the motor including instructions in computer readable code to operate the pump and to activate the motor. In one alternative, the opening in the inlet is configured as a nozzle. There may also be at least one sensor providing feedback to the system controller wherein the motor moves the movable structure in response to the feedback received from the sensor. The instructions may also include a controlled movement of the movable structure in response to feedback received by the system controller. There may also be a baffle within the reservoir adjacent the outlet.

In still other alternatives, there may be a knob connected to the first inlet or the second inlet wherein movement of the knob alters the orientation of an attached inlet. A motor may be attached to the first inlet or the second inlet wherein operation of the motor causes movement of an attached inlet. There may also be a controller that accepts user input to activate the motor. Additionally, there may be a system controller in communication with the pump and the motor including instructions in computer readable code to operate the pump and the motor to adjust conditions in the controlled therapy system. A baffle may be provided within the reservoir adjacent the outlet. The second inlet may also include a flow directing tongue positioned to direct flow from the second inlet towards the outlet. The second inlet may be configured as a nozzle.

In still other aspects, there is a knob connected to the movable inlet so that movement of the knob moves the movable inlet. There may also be a motor attached to the movable structure such that operation of the motor causes movement of the movable inlet along with a controller that accepts user input to activate the motor. In still other aspects, there may also be a system controller in communication with the pump and the motor including instructions in computer readable code to operate the pump and the motor to adjust conditions in the controlled therapy system.

BRIEF DESCRIPTION OF DRAWINGS

FIGS. 3A-3G illustrate top down views of different reservoir and baffle configurations.

FIGS. 4A and 4B are isometric views of a short baffle and long baffle, respectively, within a reservoir.

FIGS. 7, 8 and 9 are isometric and end views, respectively, of an inlet having a flow directing surface or tongue with an additional directing surface. FIGS. 8 and 9 illustrate the inlet in relation to the baffles walls and the proximity of the additional directing surface to the baffle walls.

FIGS. 30A, 30B and 30C illustrate top down views of rectangular, round and polygonal shaped reservoirs, respectively, and the alternative inlet locations shown in phantom.

FIGS. 33B and 33C are section and isometric views of the diffuser of FIG. 33A.

DETAILED DESCRIPTION OF THE INVENTION

Figure 1:
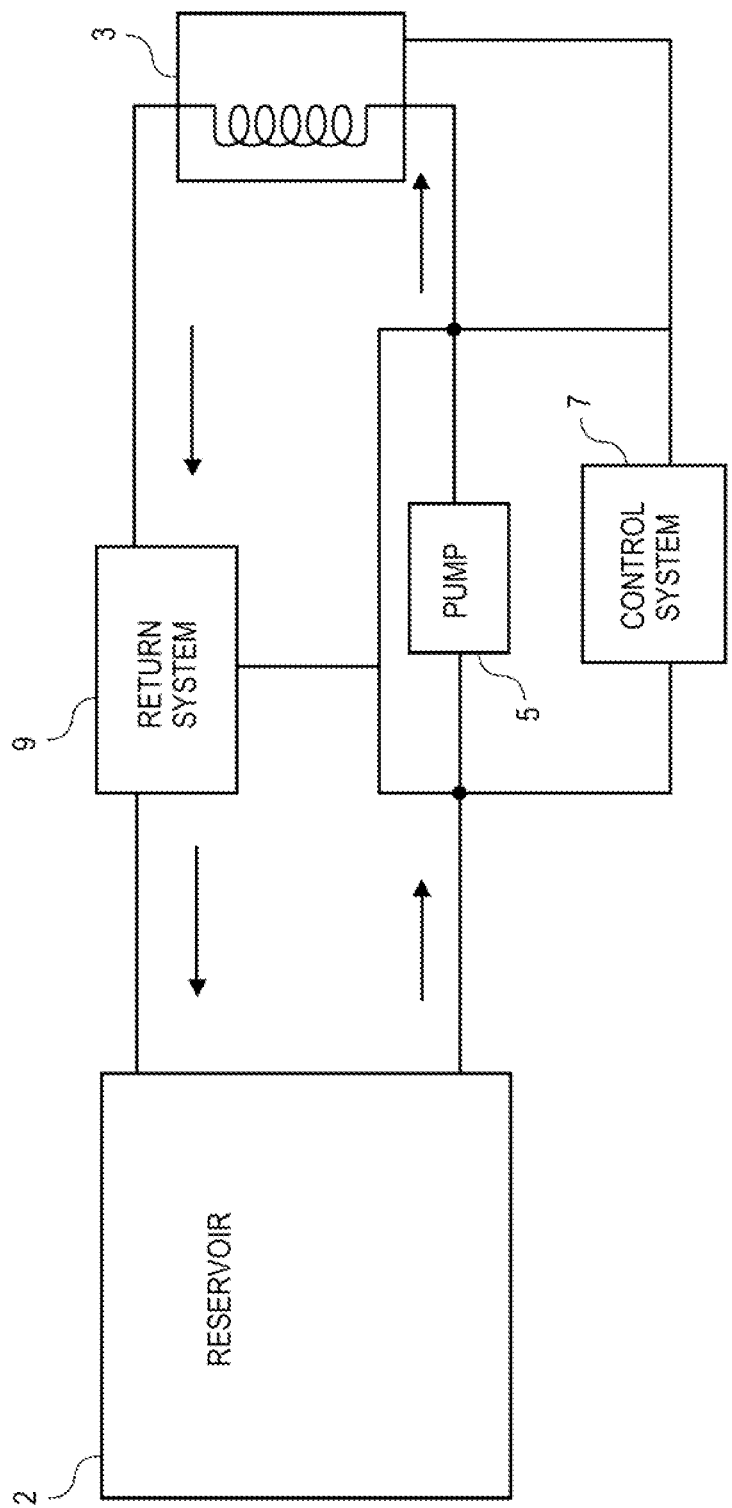
FIG. 1 illustrates an embodiment of a simplified thermal therapy device.

The subject matter of the present application is related to subject matter described in: U.S. patent application Ser. No. 09/127,256 (filed Jul. 31, 1998) entitled, "Compliant Heat Exchange Panel" issued on Apr. 3, 2007 as U.S. Pat. No. 7,198,093; U.S. patent application Ser. No. 09/798,261 (filed Mar. 1, 2001) entitled, "Shoulder Conformal Therapy Component of an Animate Body Heat Exchanger"; U.S. patent application Ser. No. 09/901,963 (filed Jul. 10, 2001) entitled, "Compliant Heat Exchange Splint and Control Unit"; U.S. patent application Ser. No. 09/771,123 (filed Jan. 26, 2001) entitled, "Wrist/Hand Conformal Therapy Component of an Animate Body Heat Exchanger"; U.S. patent application Ser. No. 09/771,124 (filed Jan. 26, 2001) entitled, "Foot/Ankle Conformal Therapy Component of an Animate Body Heat Exchanger"; U.S. patent application Ser. No. 09/771,125 (filed Jan. 26, 2001) entitled, "Conformal Therapy Component of an Animate Body Heat Exchanger having Adjustable Length Tongue"; U.S. patent application Ser. No. 10/784,489 (filed Feb. 23, 2004) entitled, "Therapy Component of an Animate Body Heat Exchanger" which is a continuation of U.S. patent application Ser. No. 09/765,082 (filed Jan. 16, 2001) entitled, "Therapy Component of an Animate Body Heat Exchanger and Method of Manufacturing such a Component" issued on Feb. 24, 2004 as U.S. Pat. No. 6,695,872 which is a continuation-in-part of U.S. patent application Ser. No. 09/493,746 (filed Jan. 28, 2000) entitled, "Cap And Vest Garment Components Of An Animate Body Heat Exchanger" issued on Jan. 30, 2001 as U.S. Pat. No. 6,178,562; U.S. patent application Ser. No. 10/122,469 (filed Apr. 12, 2002) entitled, "Make-Break Connector For Heat Exchanger" issued on Mar. 29, 2005 as U.S. Pat. No. 6,871,878; U.S. patent application Ser. No. 10/637,719 (filed Aug. 8, 2003) entitled, "Apparel Including a Heat Exchanger" issued on Sep. 19, 2006 as U.S. Pat. No. 7,107,629; U.S. patent application Ser. No. 12/208,240 (filed Sep. 10, 2008) entitled, "Modular Apparatus for Therapy of an Animate Body" which is a divisional of U.S. patent application Ser. No. 10/848,097 (filed May 17, 2004) entitled, "Modular Apparatus for Therapy of an Animate Body"; U.S. patent application Ser. No. 11/707,419 (filed Feb. 13, 2007) entitled, "Flexible Joint Wrap"; U.S. patent application Ser. No. 11/854,352 (filed Sep. 12, 2007) entitled, "Make-Break Connector Assembly with Opposing Latches", each of the above listed applications is incorporated herein by reference in its entirety.

In conventional thermal control systems using flow control to adjust system temperature, the fluid leaving the reservoir is often near freezing. A result of supplying such cold fluid is that very cold water is supplied to the wrap, even in instances when a warmer temperature setting is desired.

In aspects of the present invention, the performance of the thermal therapy device is improved by adjusting the flow rate, the temperature and providing additional features to the thermal therapy device. In a typical return flow arrangement, the velocity of the fluid is proportional to the flow rate. The higher the fluid velocity, the further the return stream would fall from a reservoir inlet wall. The further the fluid falls from the reservoir inlet wall, the temperature of fluid proximal to the reservoir outlet decreases in temperature. Such a condition would be ideal for the coldest wrap temperature setting. Conversely, the lower the flow rate, the slower the fluid velocity and the closer the return fluid would fall to the reservoir inlet wall. In this condition, the inlet temperature to the pump would be warmer. This may require relatively slow flow rates in order for the return stream to fall close enough to the reservoir outlet to significantly affect outlet temperature. Low flow rates cause higher temperature deltas between the inlet and outlet of the wrap, which provides for uneven cooling of the mammalian body part.

Reducing the flow rate of the fluid of a given temperature through the thermal therapy device will reduce the amount of energy removed from (or added to) the patient. Conversely, increasing the flow rate will increase the amount of energy removed from (or added to) a patient. In a cold therapy device, with the wrap applied to a mammalian body, the temperature of the fluid leaving the wrap is warmer than the temperature of the fluid entering the wrap because the mammalian body is much warmer than the thermal fluid. The average wrap temperature could be defined as the average of the wrap inlet temperature and wrap outlet temperature. The difference between the wrap outlet temperature and the wrap inlet temperature will be referred to as "temperature delta" through the wrap. The temperature delta through the wrap depends on fluid flow rate, heat load, and the specific heat of the thermal fluid.

As the fluid flow rate into the wrap becomes slower, the temperature delta increases as does the average wrap temperature. Therefore, to increase the desired average wrap temperature, the flow may be slowed sufficiently and a desired average wrap temperature may be achieved.

The temperature leaving the thermal reservoir is often nearly freezing (assuming again that ice water is used as the thermal fluid). This results in near freezing fluid entering the wrap because the reservoir temperature is typically very even. In order for a warmer average wrap temperature to be achieved, substantially warmer fluid must leave the wrap.

For example, if an average Wrap temperature of 5° C. was desired, and if we assume a wrap inlet temperature of 1° C. (not 0° C. due to a small amount of warming that would occur between the reservoir and the wrap) then a wrap outlet temperature of 11° C. may be needed (i.e., 11−1)/2=5). In this example, the temperature delta across the Wrap is 10° C., which is quite large. This may result in near freezing fluid entering the wrap which may be uncomfortable at best and, at worst, result in cold burns during extended periods of use.

Performance of the thermal therapy device is improved using several methods. Pre-warming the water prior to entering the wrap is desirable.

For example, assume an average wrap temperature of 5° C. was desired. If the inlet fluid was 4° C., a required outlet temperature would be 6° C. to achieve a average wrap temperature of 5° C. This would yield a temperature delta of 2° C. which provides much more even cooling than the example mentioned above. In order to achieve this desired wrap temperature, a higher fluid flow rate through the wrap would be required. Other methods of pre-warming the water prior to entering the wrap include adding a fluid heater to the system or allowing waste heat (i.e. from the pump motor) to heat the water.

FIG. 1 illustrates an embodiment of a simplified thermal therapy system 1. The thermal therapy system comprises a reservoir 2, a wrap 3, a pump 5, a control system 7 and return system 9. The arrows indicate the fluid flow exiting/leaving the reservoir 2 into the wrap 3 as well as leaving the wrap 3 and entering the reservoir 2. The system 1 may be controlled manually by a user or simply operate in on/off modes. Alternatively, the system 1 may utilize a computer control system 7 monitors or regulates fluid flow through pump 5 and the wrap 3. One or more sensors (not shown in FIG. 1 but described elsewhere below) may monitor temperature, flow rate or other characteristics of the therapy system 1. The sensor information is then used by the control system 7 to operate components of the therapy system to produce the desired therapeutic result with the wrap 3. As shown in FIG. 1, the control system 7 may be configured to regulating the return system 9. The return system 9 may be conduit used to return the heat transfer fluid in the system back to the reservoir 2. Additionally or alternatively, the return system 9 may include valves, diverters or other flow control elements (see e.g., FIGS. 44A-44C, 45, 46 and 47). In addition, the reservoir 2 may include one or more (i.e., multiple) reservoir inlets or reservoir outlets, a baffle, a filter, a diffuser or any of the reservoir improvements described herein.

One method to improve the performance of the thermal therapy device 1 is to encourage fluid leaving the reservoir outlet side of the reservoir 2 to have warmer temperatures when warmer wrap temperatures are desired. As a result, a high degree of thermal gradients across the reservoir are formed. When cold temperatures are desired, one would encourage the reservoir outlet side of the reservoir to have cold temperatures. One possible range of temperatures for these gradients may be between 0° C. and 15° C., with a preferred range between 0° C. and 10° C. Generally, reservoir fluid mixture temperatures mentioned below may also be in the ranges of 0° C. and 15° C. Other temperatures ranges may also be used.

Figure 2:
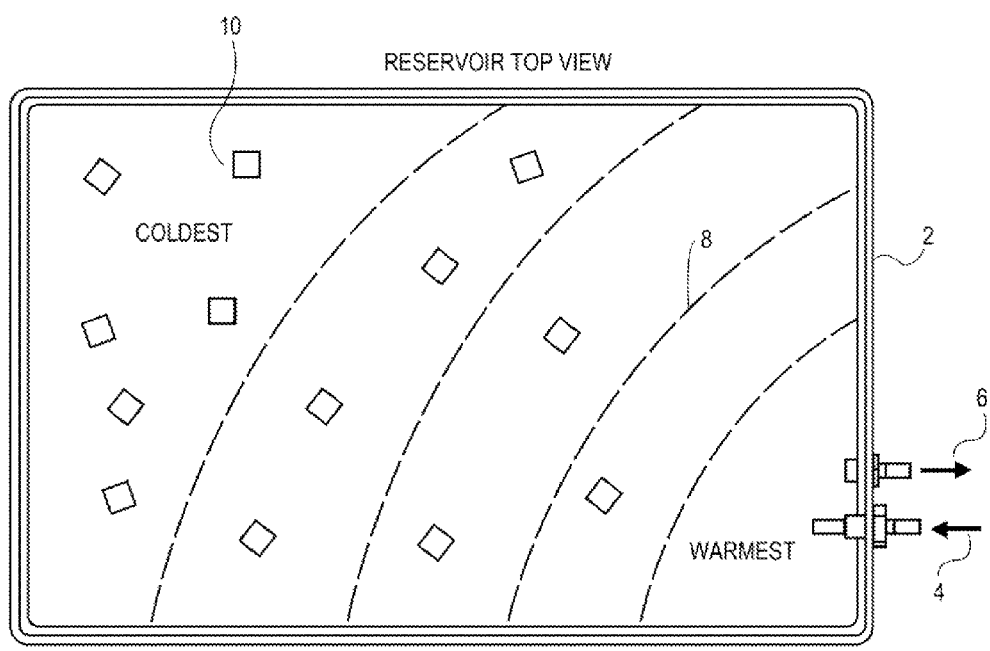
FIG. 2 illustrates an embodiment of gradients created in the reservoir in which warm reservoir fluid is collecting most proximal to the reservoir outlet.

FIG. 2 illustrates isotherms 8 created in a conventional reservoir 2. The top down view of FIG. 2 illustrates reservoir 2 comprising a reservoir inlet 4 and reservoir outlet 6. The warmer fluid from wrap 3 enters through inlet 4. Since at low pump speeds, the warmer water remains generally close to the inlet, isotherms 8 are produced in the reservoir fluid mixture 10 made of a fluid and ice. The isotherms 8 are created as a result of warmer temperatures in different areas of the reservoir 2. One shortcoming of the conventional reservoir is that as pump speeds increase, the warmer return water is sprayed farther into the reservoir and separated from the outlet. In addition, the increased velocity of the return flow may also cause circulation of the water and ice mixture and actually cause ice to circulate around within the reservoir or perhaps remain in proximity to the outlet thereby decreasing the reservoir temperature near the outlet.

One method of creating isotherms is to provide proximal return streams where warm water is returned from the wrap 3 through the reservoir inlet 4 in close proximity to the reservoir outlet 6 while mitigating the unwanted effects described above. The various improvement described herein provide improvements and methods for achieving and maintaining the isotherms 8 closer to the reservoir outlet. The result is increased control over reservoir temperatures thereby enabling improved wrap temperature control.

Another method to improve the performance of the thermal therapy device 1 is the addition of a baffle or partial wall to the reservoir 2. The baffle may be a set of walls generally parallel and spaced close together that extend far enough into the ice bath so as to prevent ice from gathering too close to the reservoir outlet. The baffle may be referred to as an ice baffle.

By adding a baffle to a reservoir, ice is prevented from immediately gathering around the reservoir outlet and returning the water from the wrap directly over the reservoir outlet, an area of the reservoir most proximate to the outlet can be warmer. If the return stream is oriented in a horizontal direction, the slower the flow rate, the closer the return fluid lands to the reservoir outlet, which in turn, more effectively warms the surrounding reservoir fluid most proximal to the reservoir outlet. This provides a higher inlet temperature to the wrap 3, thus allowing the pump speed to be increased for the same average wrap 3 temperature. This then allows for a smaller temperature delta between the inlet and outlet of the wrap and thus a more consistent wrap temperature.

Conversely, the faster the flow rate, the higher the velocity of the return stream, and the further the return stream lands from the reservoir outlet. This results in less local warming of the fluid most proximal to the reservoir outlet fluid, and provides a colder temperature at the wrap. Thus, by varying the flow rate in thermal therapy systems having one or more of the inventive aspects described herein, the outlet temperature of the reservoir fluid can be affected, thus affecting the internal wrap temperature in much the same manner.

FIGS. 3A, 3B, 3C, 3D, 3E, 3F and 3G illustrate top down views of a number of alternative baffle and reservoir embodiments. The reservoir is a container 52 with an interior 54 defined by a floor 53 and at least one wall. There is an inlet 106 in fluid communication with the interior 54 and in fluid communication with a therapy component 3. There is also an outlet 104 in fluid communication with the interior 54 through a penetration in the at least one wall at a location closer to the floor 53 than the inlet 106. The outlet 104 in fluid communication with the pump 5. A baffle is created by a first wall and a second wall within the interior 54. The first and second walls are spaced apart wider than the outlet 104 but narrower than the width of the interior adjacent the inlet 106.

In some embodiments, the inlet 106 and/or the associated inlet are placed in a location to that the inlet is above the surface of the heat transfer fluid when in use. When in use the heat transfer fluid exiting the inlet 106 enters the interior 54—in some cases—above the surface of the heat transfer fluid within the container 52. It is to be appreciated that the inlet may be a movable inlet as described herein that is positioned to adjust between a position below the surface of the heat transfer fluid 10 and above the surface of the heat transfer surface 10.

FIG. 3A is a top down view of a reservoir 50a. The reservoir 50a has a container 52 made of a floor 53 and walls 62, 64, 66 and 68. A baffle 58 is formed by a wall 56 within the interior 54 and a portion of the wall 62. The wall 56 and the portion of the wall 62 are spaced apart by a width w wider than the outlet 104 but narrower than the width of the interior adjacent the inlet 106.

FIG. 3B is a top down view of a reservoir 50b. The reservoir 50b has a container 52 made of a floor 53 and walls 62, 64, 66 and 68. A baffle 70 is formed by a wall 71 and wall 72 within the interior 54. The baffle may be formed by attaching the walls 71, 72 to the container interior or as a separate component (i.e., a standalone baffle) as described in the embodiments below. The walls 71, 72 are spaced apart by a width w that is wider than the outlet 104 but narrower than the width of the interior adjacent the inlet 106. In addition, the walls 71, 72 are spaced narrower than the reservoir width. In other words, the baffle is narrower than the adjacent container wall. In the illustrated example, the baffle 70 is narrower than the wall 68.

FIGS. 3C-3G illustrate alternative reservoir configurations where the baffle is formed by or contained within a wall recess 75.

FIG. 3C is a top down view of a reservoir 50c. The reservoir 50c has a container 52 made of a floor 53 and walls 62, 64, 66 and 68. A recess 75a is formed in wall 68. The recess 75a may be used to provide a baffle 70. Alternatively, a baffle 70 is formed by a wall 71 and wall 72 inserted into the recess 75a. The baffle may be formed by attaching the walls 71, 72 to the recess 75a interior. Alternatively, the baffle 70 may be a separate component (i.e., a standalone baffle as described in the embodiments below) placed into the recess 75a. The walls 71, 72 are spaced apart by a width w that is wider than the outlet 104 but narrower than the width of the interior adjacent the inlet 106. In addition, the walls 71, 72 are spaced narrower than the reservoir width. In other words, the baffle is narrower than the adjacent container wall. In the illustrated example, the baffle 70 is narrower than the wall 68.

FIG. 3D is a top down view of a reservoir 50d. The reservoir 50d has a container 52 made of a floor 53 and walls 62, 64, 66 and 68. A recess 75b is formed in wall 68. The recess 75b is narrower than the recess 75a. The recess 75b may be used to provide a baffle 70 that is narrower than the baffle provided by recess 75a. Alternatively, a baffle 70 is formed by a wall 71 and wall 72 inserted into the recess 75b. The baffle may be formed by attaching the walls 71, 72 to the recess 75b interior. Alternatively, the baffle 70 may be a separate component (i.e., a standalone baffle as described in the embodiments below) placed into the recess 75b. The walls 71, 72 are spaced apart by a width w that is wider than the outlet 104 but narrower than the width of the interior adjacent the inlet 106. In addition, the walls 71, 72 are spaced narrower than the reservoir width. In other words, the baffle is narrower than the adjacent container wall. In the illustrated example, the baffle 70 is narrower than the wall 68.

FIG. 3E is a top down view of a reservoir 50e. The reservoir 50e has a container 52 made of a floor 53 and walls 62, 64, 66 and 68. A recess 75c is formed in wall 68. The recess 75c is narrower than the recess 75b. The recess 75c may be used to provide a baffle 70 that is narrower than the baffle provided by recess 75b. Alternatively, a baffle 70 is formed by a wall 71 and wall 72 inserted into the recess 75c. The baffle may be formed by attaching the walls 71, 72 to the recess 75c interior. Alternatively, the baffle 70 may be a separate component (i.e., a standalone baffle as described in the embodiments below) placed into the recess 75c. The walls 71, 72 are spaced apart by a width w that is wider than the outlet 104 but narrower than the width of the interior adjacent the inlet 106. In addition, the walls 71, 72 are spaced narrower than the reservoir width. In other words, the baffle is narrower than the adjacent container wall. In the illustrated example, the baffle 70 is narrower than the wall 68.

FIG. 3F is a top down view of a reservoir 50f. The reservoir 50f has a container 52 made of a floor 53 and walls 62, 64, 66 and 68. A recess 75d is formed in wall 68. The recess 75d is narrower than the recess 75c. The recess 75d may be used to provide a baffle 70 that is narrower than the baffle provided by recess 75c. Alternatively, a baffle 70 is formed by a wall 71 and wall 72 inserted into the recess 75d. The baffle may be formed by attaching the walls 71, 72 to the recess 75b interior. Alternatively, the baffle 70 may be a separate component (i.e., a standalone baffle as described in the embodiments below) placed into the recess 75d. The walls 71, 72 are spaced apart by a width that is wider than the outlet 104 but narrower than the width of the interior adjacent the inlet 106. In addition, the walls 71, 72 are spaced narrower than the reservoir width. In other words, the baffle is narrower than the adjacent container wall. In the illustrated example, the baffle 70 is narrower than the wall 68.

FIG. 3G is a top down view of a reservoir 50g. The reservoir 50g has a container 52 made of a floor 53 and walls 62, 64, 66 and 68. A recess 75e is formed between adjacent walls 62, 68. The recess 75e may be used to provide a baffle 70 in a different orientation to the interior 54. Alternatively, a baffle 70 is formed by a wall 71 and wall 72 inserted into the recess 75e. The baffle may be formed by attaching the walls 71, 72 to the recess 75e interior. Alternatively, the baffle 70 may be a separate component (i.e., a standalone baffle as described in the embodiments below) placed into the recess 75e. The walls 71, 72 are spaced apart a distance w wider than the outlet 104.

Figure 4B:
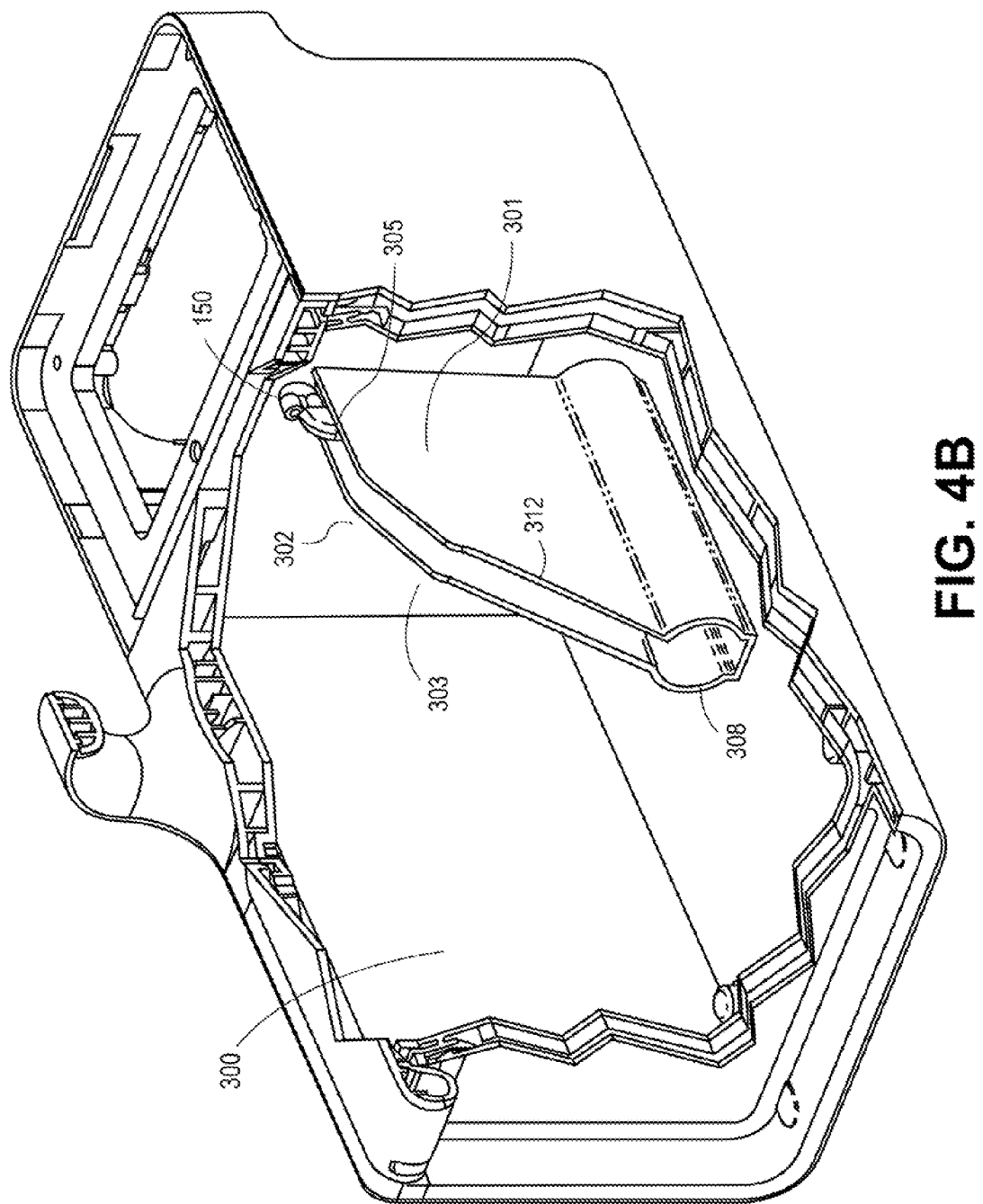

FIGS. 4A and 4B are isometric partial section views of a reservoir 300 with a baffle 302 disposed therein. Two alternatives of a baffle 302 are shown. Additional baffle alternatives are illustrated below.

The baffle 302 is comprised of two separated walls 301 and 303. The baffle 302 further comprises a filter access 308 at the bottom of the baffle 302. The filter access 308 is partially circular in shape to allow for easy access to the filter. A filter may be placed into the access 308 or it may receive a filter cartridge as described below (see for example FIGS. 27C, 38, 39-41D). Alternatively, the baffle may be just one wall as shown in FIG. 3A or 3H. In FIG. 4A, the baffle 302 comprises a horizontal portion 305, an angled portion 304 and a vertical portion 306. In FIG. 4B, the baffle 302 comprises a horizontal portion 305 and angled portion 312. In contrast to FIG. 4A, the baffle 302 illustrated in FIG. 4B is shaped such that the bottom edge is longer in length than the top edge which is closer to the reservoir inlet or nozzle 310.

In addition, the baffle may comprise of compartments or chambers of different shapes and sizes so as to prevent ice from gathering too close to the reservoir outlet. (See e.g., FIGS. 27A-27C).

Figure 32:
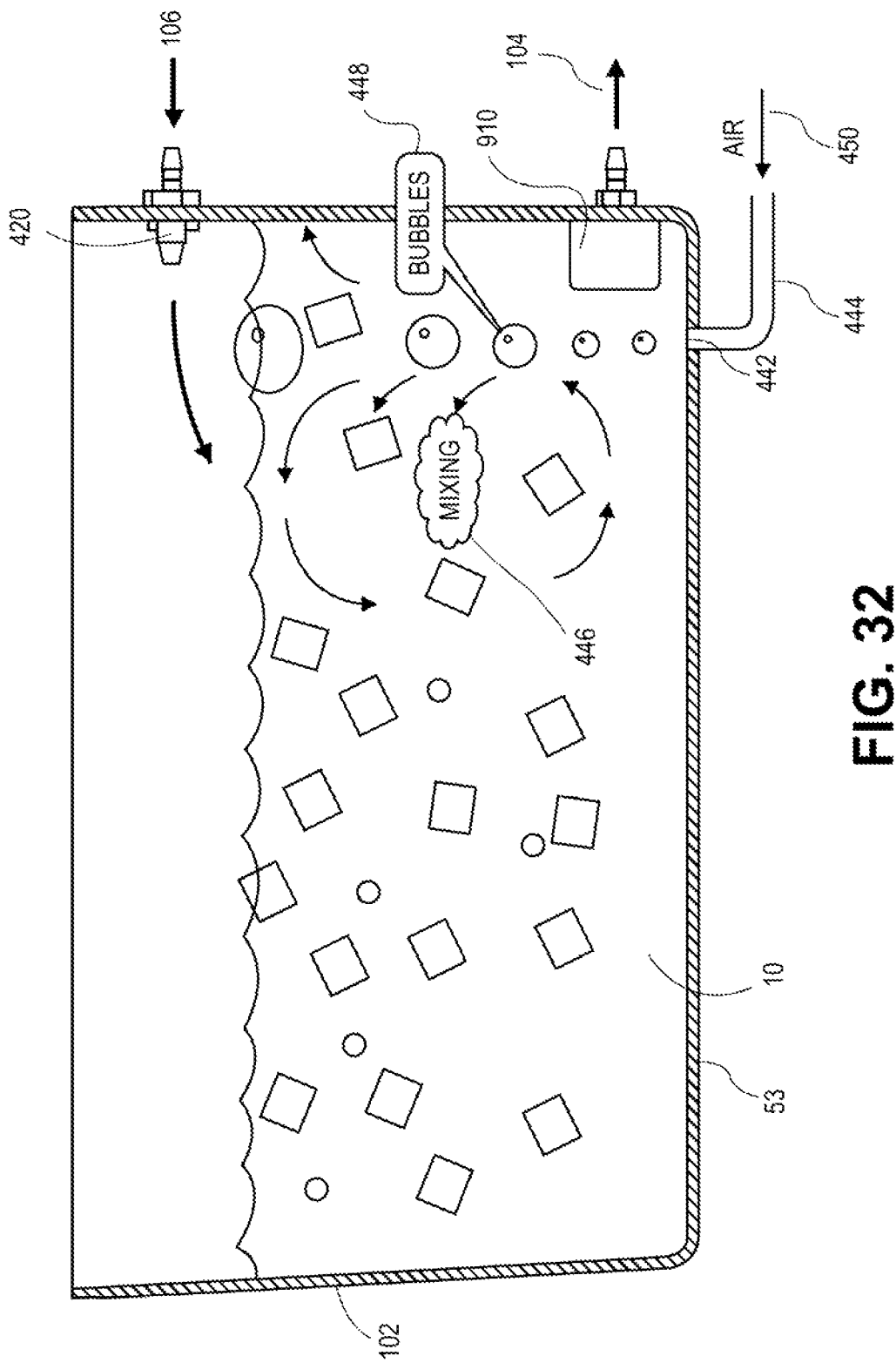
FIG. 32 is a top down view of a reservoir having an air bubbler in communication with the reservoir to encourage fluid mixing.
Figure 33A:
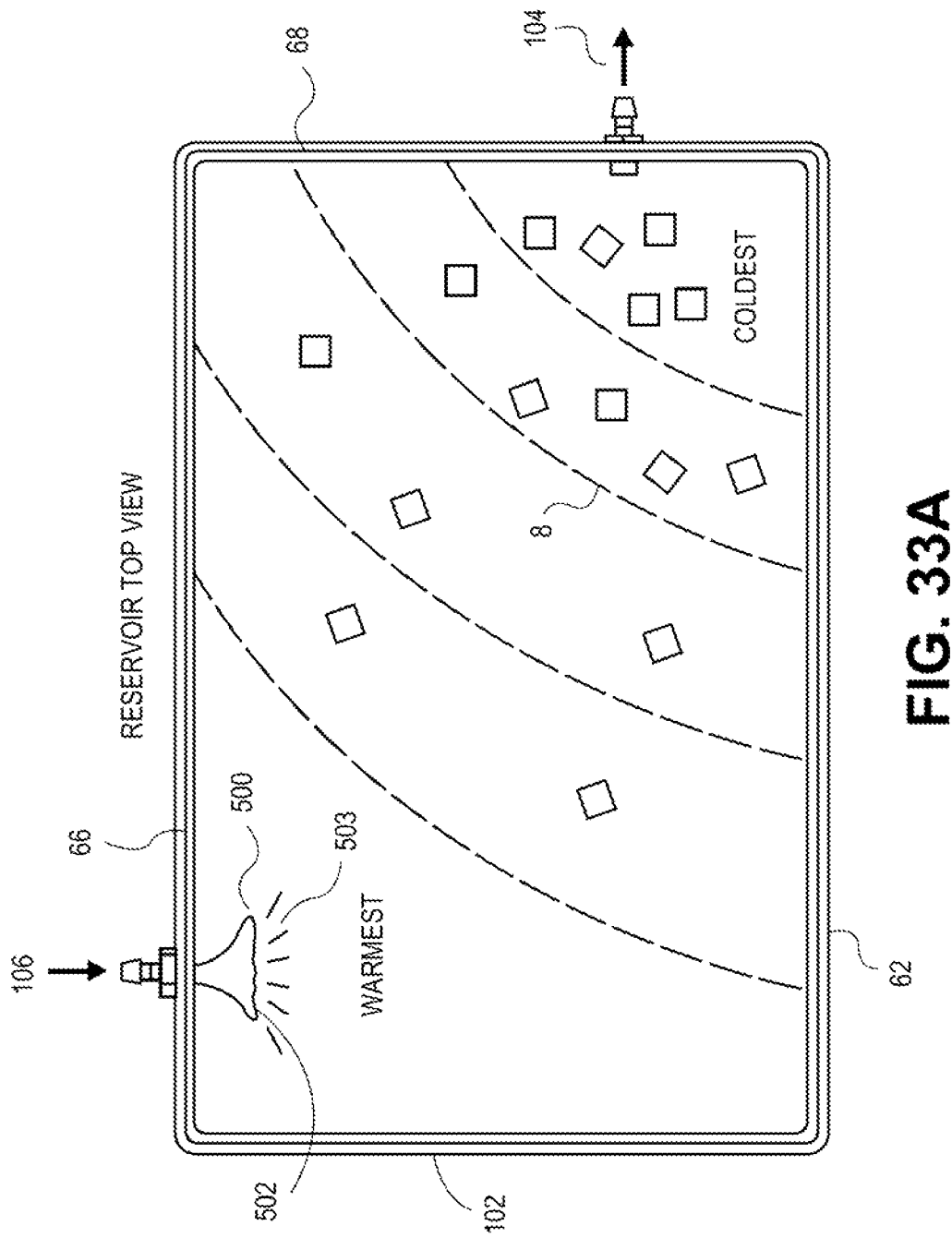
FIG. 33A is a top down view of a reservoir with a diffuser.
Figure 34:
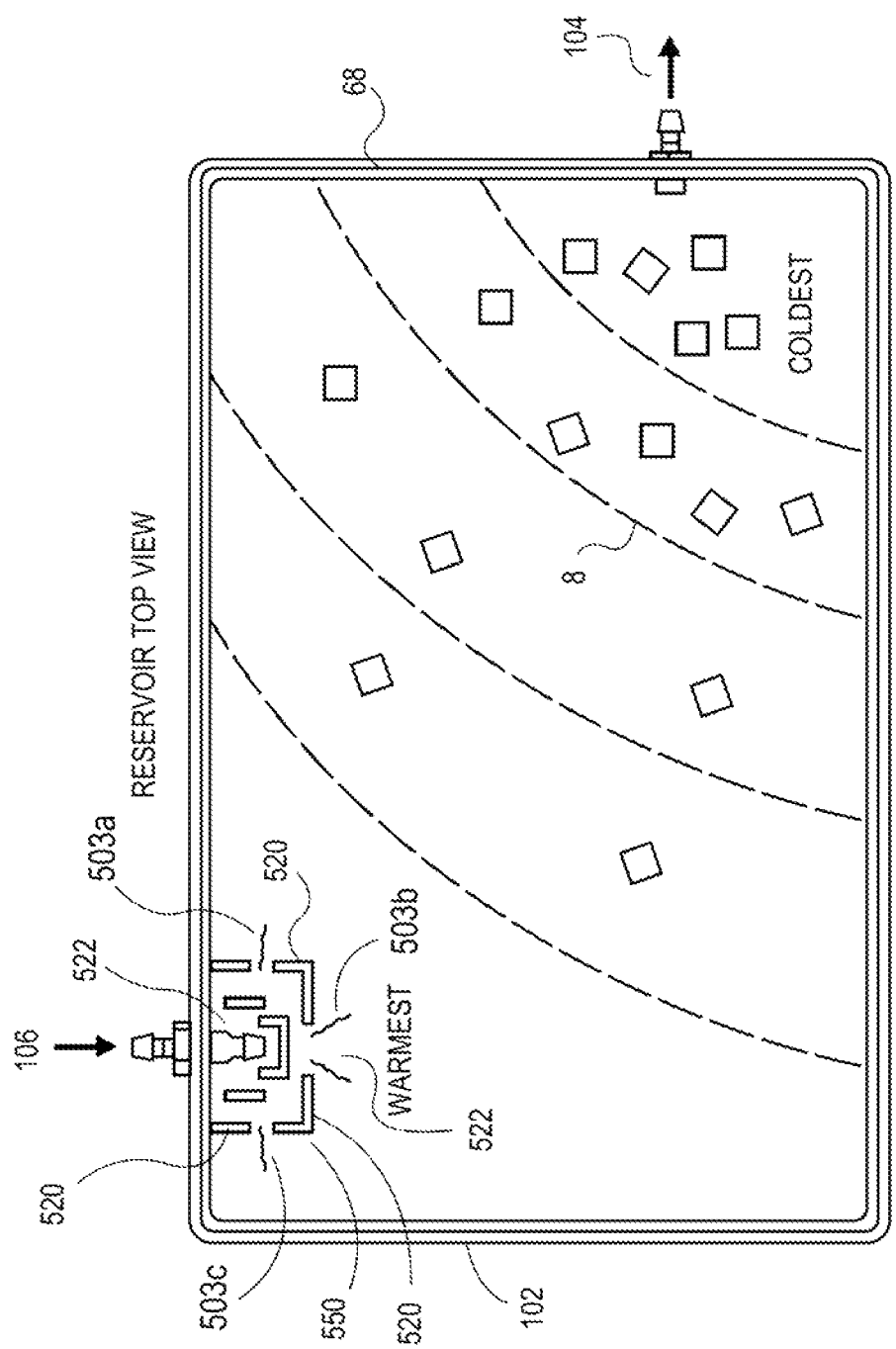
FIG. 34 is a top down view of a reservoir with a diffuser with multiple walls.
Figure 35:
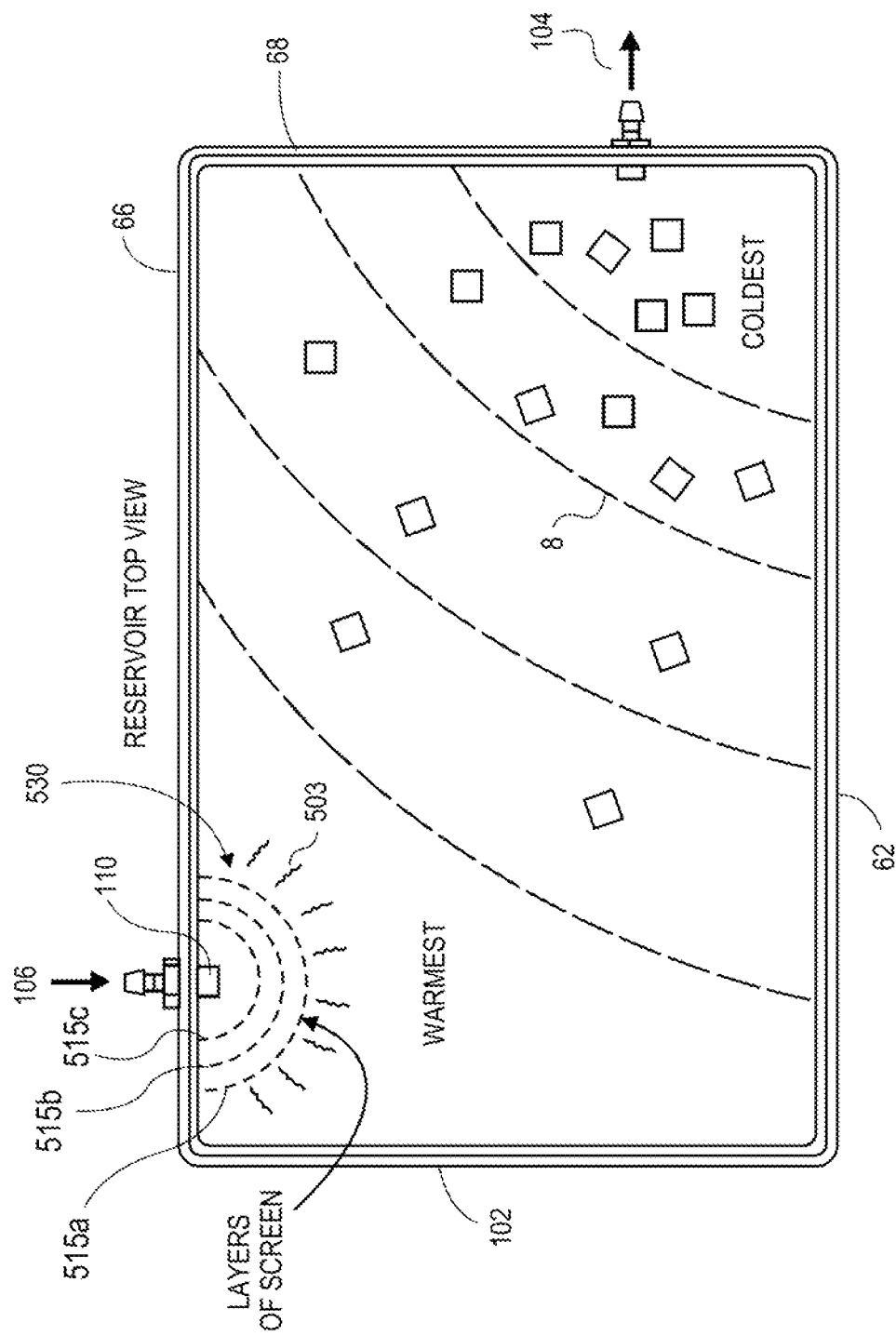
FIG. 35 is a top down view of a reservoir with a diffuser with multiple screens.

Another method to improve the performance of a thermal therapy system 1 is to provide improvements or alterations in the manner or device used as an inlet to the reservoir. For example, a conventional inlet may be used in combination with a baffle to achieve the reservoir performance improvements provided by the use of a baffle as described herein. The inlet may be modified in accordance with the alternatives that follow. Those improved inlets may also be used in conjunction with a baffle. However, the inlet improvements may also be used in reservoirs without baffles. A number of inlet improvements are described below including, for example: a flow modification feature or tongue (e.g., FIGS. 5-13), a movable inlet such as, for example, a pivoting inlet (e.g., FIGS. 21A, 21B, 22A-C, and 23-26), a flexing or deflectable inlet (e.g., FIGS. 18, 19 and 20), an inlet configured as a nozzle (e.g., FIGS. 16, 17, 28A, 29, and 32), and an inlet used in combination with a diffuser (FIGS. 33A, 34 and 35).

A flow directing element may be attached or coupled to the reservoir inlet or to provide an extension of a reservoir inlet. Embodiments of an inlet with a flow directing surface or tongue are illustrated in FIGS. 5-13 configured to optimize flow returning from the wrap 3 to the reservoir 2. A tongue portion 22 is connected to the body 153. The tongue portion 22 is configured to allow fluid leaving the front opening 28 to flow over and/or around the tongue portion 22 at low to medium flow rates, as illustrated by flow 108 in FIGS. 14A and 14B. At medium high flow rates, as shown in FIG. 14C, a portion of the fluid flow 108a remains over and/or around the tongue portion 22 and another portion of the fluid 108a breaks free and projects beyond the tongue portion 22. At high flow rates, the fluid breaks free and projects beyond the tongue portion 22, as illustrated in FIG. 14D with the flow 108.

Figure 5:
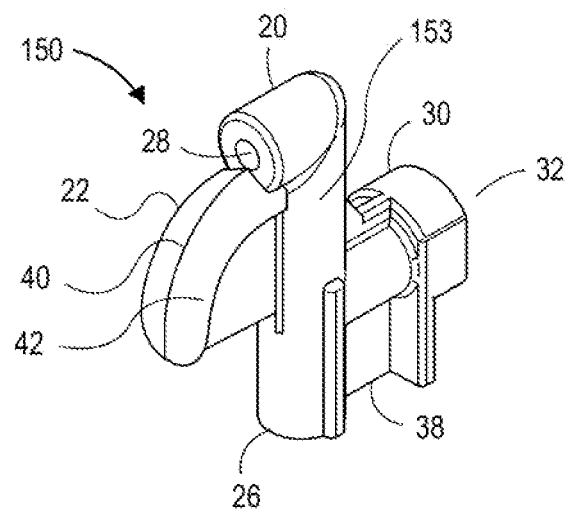
FIGS. 5 and 6 are isometric and section views, respectively, of an inlet having a flow directing surface or tongue.
Figure 6:
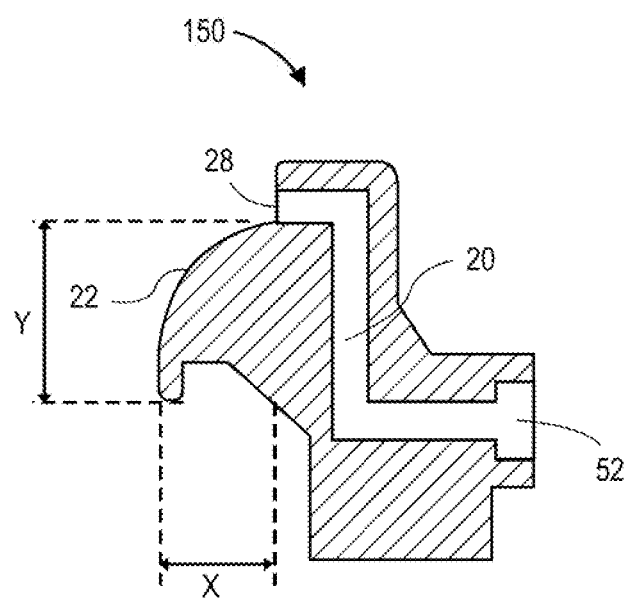

In particular, FIGS. 5 and 6 are isometric and cross section views, respectively of a flow directing inlet 150. The flow directing inlet 150 includes a body 153. A tubular portion 20 within the body 155 connects a back opening 52 with an opening or outlet 28. The back opening 52 is used to connect to the reservoir inlet 106 using any suitable means such as with a clamp, a barb fitting and the like. A tongue or flow directing surface 22 extends from the outlet 28 in a curve arc as best seen in FIG. 6. The tongue extends away from the outlet 28 and towards the reservoir floor. The length and shape of the tongue 22 produce a lateral separation x and a vertical separation y from the outlet 28 to the distal end of the tongue. The lateral separation x and the vertical separation y may vary depending upon a number of factors such as operating conditions in the system. The lateral separation x is typically about 2 cm and can range from about 0.5 cm to about 5 cm. The vertical separation y is typically about 3 cm and can range from about 0.5 cm to the height of the reservoir. As best seen in FIG. 5, the top surface of the tongue 22 includes an elevated portion or ridge 40. In one aspect, the ridge or elevated portion 40 is aligned with the outlet 28. The various embodiments of the flow directing inlet may be used alone or in conjunction with a baffle, as illustrated in FIGS. 4A and 4B.

The length, overall shape and contour (i.e., ridge 40) of the tongue 22 are selected to interact with the flow exiting outlet 28. In use, flow through the inlet 150 passes along the tubular portion 20 and out the front opening of outlet 28. Depending on the speed of the flow leaving the opening 28, the flow will either run along all or part of the length of the tongue or flow directing surface 22.

An alternative flow directing inlet is illustrated in FIGS. 7 and 8. FIGS. 7 and 8 are isometric and end views, respectively of a flow directing inlet 155. The flow directing inlet 155 is similarly constructed to the flow directing inlet 150. A tongue or flow directing surface 22 extends from the outlet 28 in a curve as best seen in FIG. 7. The tongue extends away from the outlet 28 and towards the reservoir floor. The length and shape of the tongue 22 produce a lateral separation from the outlet 28 to the distal end of the tongue. As best seen in FIG. 8, the top surface of the tongue 22 includes an elevated portion or ridge 40. In one aspect, the ridge or elevated portion 40 is aligned with the outlet 28.

In contrast to flow directing inlet 150, the flow directing inlet 155 includes a transition area or surface 42 extending from one side of the tongue 22 towards a directing structure 24. The length, overall shape and contour (i.e., ridge 40) of the tongue 22 are selected to interact with the flow exiting outlet 28. In use, flow through the inlet 155 passes along the tubular portion 20 within body 153 and out the front opening or outlet 28. Depending on the speed of the flow leaving the opening 28, the flow will either run along all or part of the length of the tongue or flow directing surface 22. Some of the flow falling away from the elevated portion 40 will flow onto the transition area 42. The transition area 42 is sloped towards the directing structure 24.

As best seen in FIG. 9 the directing structure 24 is bell-shaped structure positioned to direct the flow onto an adjacent baffle wall. As illustrated in FIG. 9, the directing structure 24 directs flow onto the interior of baffle wall 301. While described as two parts, it is to be appreciated that the tongue, transition structure and directing structure may be formed integrally and with other shapes suited to directing flow from the tongue to a baffle wall.

It is to be appreciated that the tongue may be of any shape, size or material configured to optimize flow returning from the wrap to the reservoir. Alternatively, the directing surface or tongue may have other shapes, sizes and components such that at low and medium flow rates, the surface tension acting between the surface and in the flow from the inlet directs the fluid downwards towards the reservoir inlet. At higher flow rates, the velocity is high enough such that the return fluid breaks free of the directing surface and projects far away from the reservoir inlet and the reservoir outlet.

Generally, the nozzle allows return fluid to land proximal to the reservoir outlet in low and medium flow rates, and far from the reservoir outlet at higher flow rates. The surface tension of the return fluid allows the fluid to flow across a properly engineered surface of the nozzle. The ranges for flow rates may be between 50 ml per minute and 1.5 liter per minute. A preferable range may be from 150 ml per minute to 550 ml per minute. One possible range for low flow rate may be 150 ml per minute to 249 ml/minute, for medium flow rate may be 250-350 ml/min and for high flow rate may be 351 ml per minute to 550 ml per minute. Other ranges may be desirable as well.

In addition, the tongue may be modified to further alter the interaction with the flow from the outlet 28. These alternatives are illustrated in FIGS. 10-13. In each of these embodiments, the modified flow inlet is positioned between the walls 301, 303 of a baffle 302. While illustrated as modifications of the flow directing inlet 155 with both a transition area 40 and flow directing structure 24, the modifications are not so limited. The modifications described in FIGS. 10-13 are also applicable to the flow directing inlet 150 illustrated in FIGS. 5 and 6.

FIGS. 10-13 each illustrate an alteration to the tongue 22. Specifically, the upper surface of the tongue 22 is modified from that of inlets 150, 155.

Figure 10:
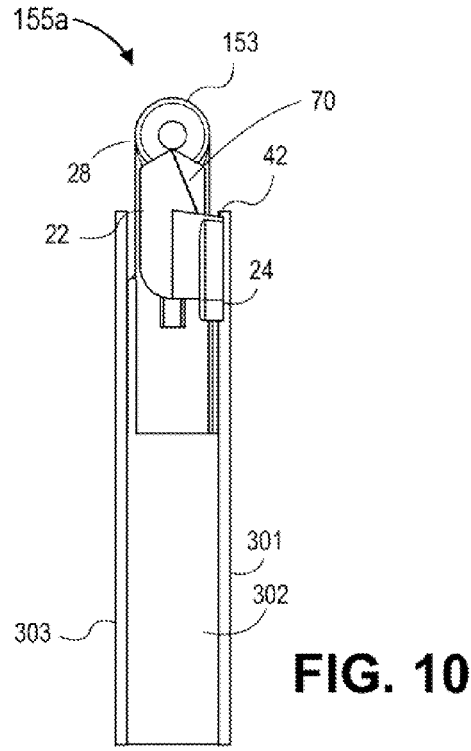
FIGS. 10, 11, 12 and 13 are end views of an inlet having a flow directing surface or tongue modified to alter the interaction of the surface of the tongue with the fluid flowing across it.

In FIG. 10, the upper ridge or elevation 70 moves from a centerline position near outlet 28 towards one side as it traverses towards the tongue distal end. In this manner, the angled ridge 70 will direct flow towards the wall 301. In the illustrated embodiment, the angled ridge 70 acts in furtherance of the purpose of transition area 42 and directing structure 24. While illustrated with the transition area 42 and the directing structure 24, the angled ridge 70 may be used without those additional structures.

Figure 11:
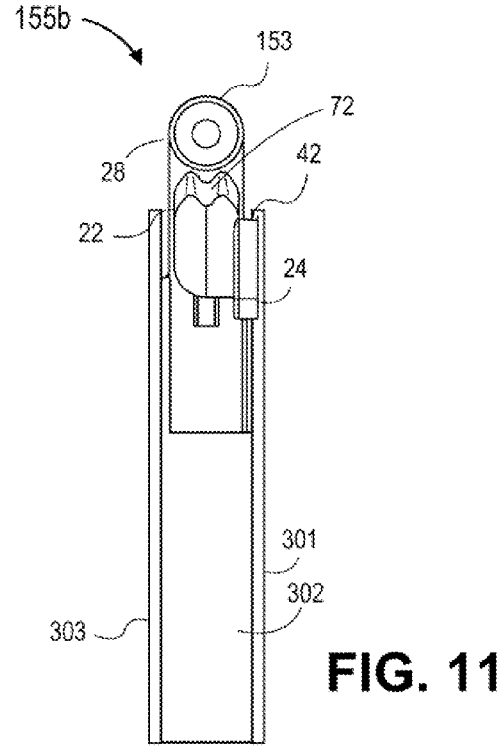

In FIG. 11, the upper surface of the tongue includes a groove or recess 72 along the centerline position near outlet 28 and extending towards the tongue distal end. The depth of the recess 72 and its general concave shape near the centerline permit the tongue upper surface to maintain a generally convex cross section. While illustrated as straight along the surface, the recess 72 may be angled as with angled ridge 70 to direct flow towards the wall 301. While illustrated with the transition area 42 and the directing structure 24, the recess 72 may be used without those additional structures.

Figure 12:
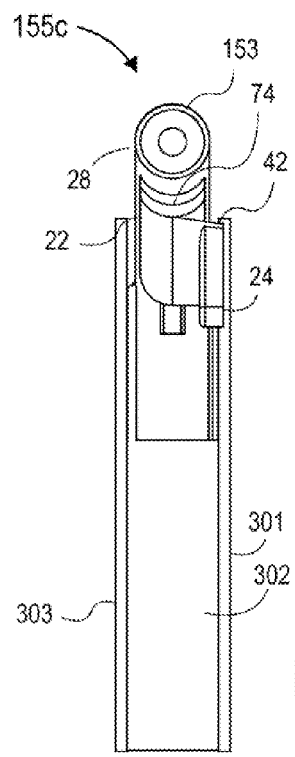

In FIG. 12, the upper surface of the tongue is shaped as an u-shaped groove or recess 74 along the centerline position near outlet 28 and extending towards the tongue distal end. The depth of the recess 74 alters the cross section of the tongue to have an overall concave shape. While illustrated as straight along the surface, the recess 74 may be angled as with angled ridge 70 to direct flow towards the wall 301. While illustrated with the transition area 42 and the directing structure 24, the recess 74 may be used without those additional structures.

Figure 13:
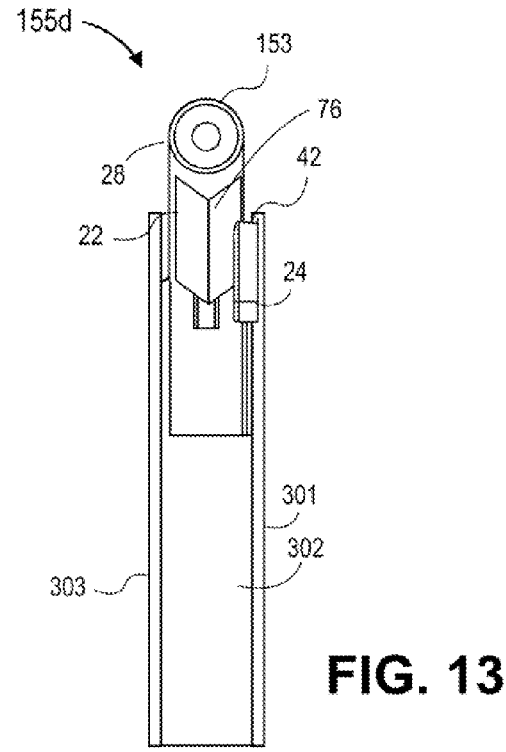

In FIG. 13, the upper surface of the tongue is shaped as a v-shaped groove or recess 76 along the centerline position near outlet 28 and extending towards the tongue distal end. The depth of the recess 76 alters the cross section of the tongue to have an overall v-shape. While illustrated as straight along the surface, the recess 76 may be angled as with angled ridge 70 to direct flow towards the wall 301. While illustrated with the transition area 42 and the directing structure 24, the recess 76 may be used without those additional structures.

Figure 16:
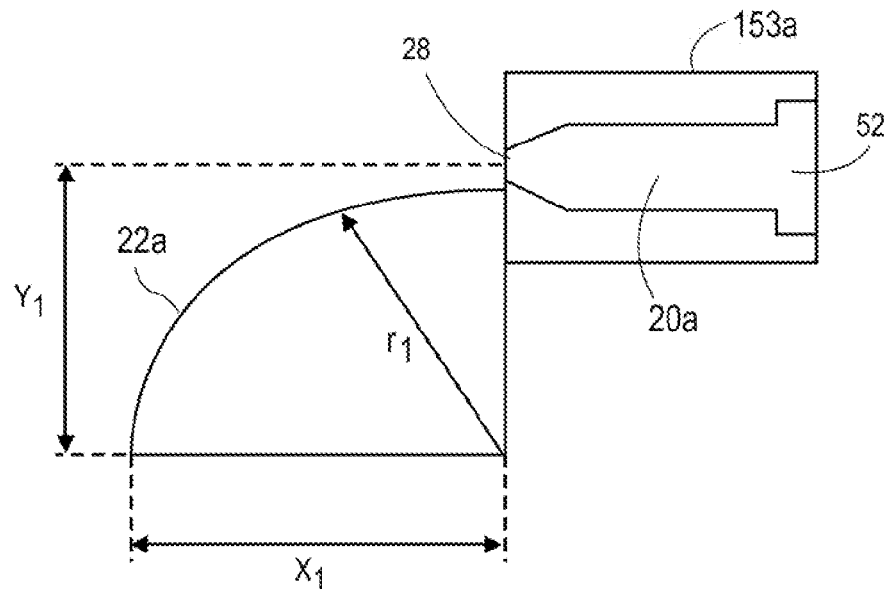
FIGS. 16 and 17 are section views of an inlet configured to provide a nozzle as well as a flow directing surface.
Figure 17:
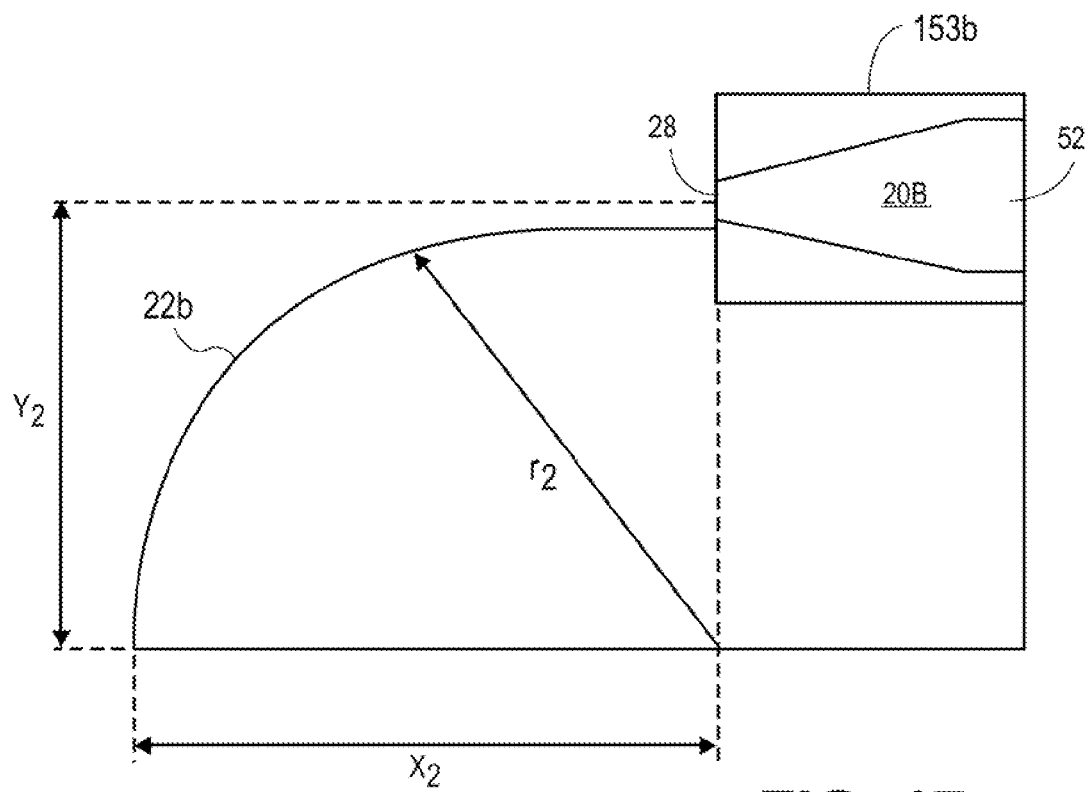

FIGS. 16 and 17 illustrate alterations to the body 153 and the tongue 22. In contrast to the generally constant bore diameter of the tubular portion 20 (see FIG. 6), the tubular portions 20a and 20b having variable bore diameters. In addition, the flow paths 20a, 20b place the outlet 28 in a more direct path with the opening 52 (in contrast to the rise found in tubing 20 of FIG. 6). Importantly, both tubular portions 20a, 20b have reduced diameters so that outlet 28 is now a nozzle outlet. It is to be appreciated that the bodies 153a, 153b illustrated in FIGS. 16 and 17 may be used as inlets only— without the tongue portion 22. In other words, the body 153a in FIG. 16 may be fabricated without a tongue 22 so that only the body 153a with outlet 28 is connected to a reservoir. Similarly, the body 153b in FIG. 17 may be fabricated without a tongue 22 so that only the body 153a with outlet 28 is connected to a reservoir.

FIGS. 16 and 17 also illustrate the additional variation possible with the tongue 22 to influence a wide range of fluid flows. The tongue 22 has a horizontal displacement (x) extending from the outlet 28 towards the reservoir interior— in general terms towards an opposite wall in the reservoir. The tongue 22 has a vertical displacement (y) extending from the outlet 28 towards the reservoir floor or bottom—in general terms towards the reservoir outlet. Tongues 22a and 22b both follow generally curved shapes. While not exactly circular, the tongue shape may be approximated as a section of a circle with a radius r.

FIG. 16 shows how the displacement x1, y1 produces a shorter radius tongue 22a of radius r1. In this way, the flow from outlet 28 will be directed nearly directly beneath the outlet 28 as a result of the small horizontal displacement x1. However, such a short radius r1 will likely only influence slower flow rates. As flow rate increases, the flow will likely separate from the tongue 22a and be directed more generally into the interior.

FIG. 17 shows how the displacement x2, y2 produces a longer radius tongue 22b of radius r2. In this way, the flow from outlet 28 will be directed towards an area at some distance from the outlet 28 as a result of the larger horizontal displacement x2. However, such a long radius r2 will likely influence a wider range of fluid flow rates. As flow rate increases, the flow will likely remain on the tongue 22b and directed generally towards the inlet. It is not until the flow rate increases more that the flow will separate from tongue 22b and be directed more generally into the interior.

The diameter of the front opening 28 may be adjusted in conjunction with the shape of the tongue portion 22 to effect performance of the nozzle 80. With the larger diameter of the front opening 28, the return fluid flow rate must be higher before the return stream begins to break away from the nozzle 80. Conversely, with a smaller diameter of the front opening 28, the return steam will break away from the nozzle at a lower flow rates.

The opening 52 may be placed over a barbed tube fitting or otherwise secured to and/or threaded in the reservoir wall.

Next, we compare operation of a system with two different reservoir configurations. In both configurations, the reservoir 102 includes an inlet 106, an outlet 104 and a baffle 302 and is shown in section view. The baffle 302 includes a filter opening 308 containing a filter cartridge 910 over the outlet 104. The wall 303 is visible in this view. In FIGS. 15A-15C, the inlet 106 is connected to an inlet tube 110. In FIGS. 14A-14D, the inlet 106 is in communication with a fluid directed surface inlet 150 aligning the opening 28 with a directed surface or tongue 22.

The sequences of FIGS. 14A-D and 15A-C illustrate return flow paths to the reservoir 102 at different flow rates. The reservoir 102 contains a heat exchange mixture 10. In these examples, the heat transfer mixture is water and ice. The inlet 106 penetrates the reservoir wall above the level of the heat transfer mixture. Both the outlet 28 and the outlet of the inlet tube 110 are positioned above the level of the heat transfer mixture 10. In the illustrated embodiments, the reservoir 102 is shown in section view. The reservoir 102 also contains a baffle 302, but in this view, only the wall 303 of the baffle is visible. The baffle also includes the filter channel 308 containing filter cartridge assembly 910 over the reservoir outlet 104. In use, the heat exchange mixture 10 fluid flows from the reservoir inlet 106 to an inlet tube 110 in FIGS. 15A-C. In use, the heat exchange mixture 10 fluid flows from the reservoir inlet 106 to an fluid directing inlet 150 with a flow directed surface or tongue 22 as shown in FIGS. 14A-14D.

The Low Flow Condition

Figure 14A:
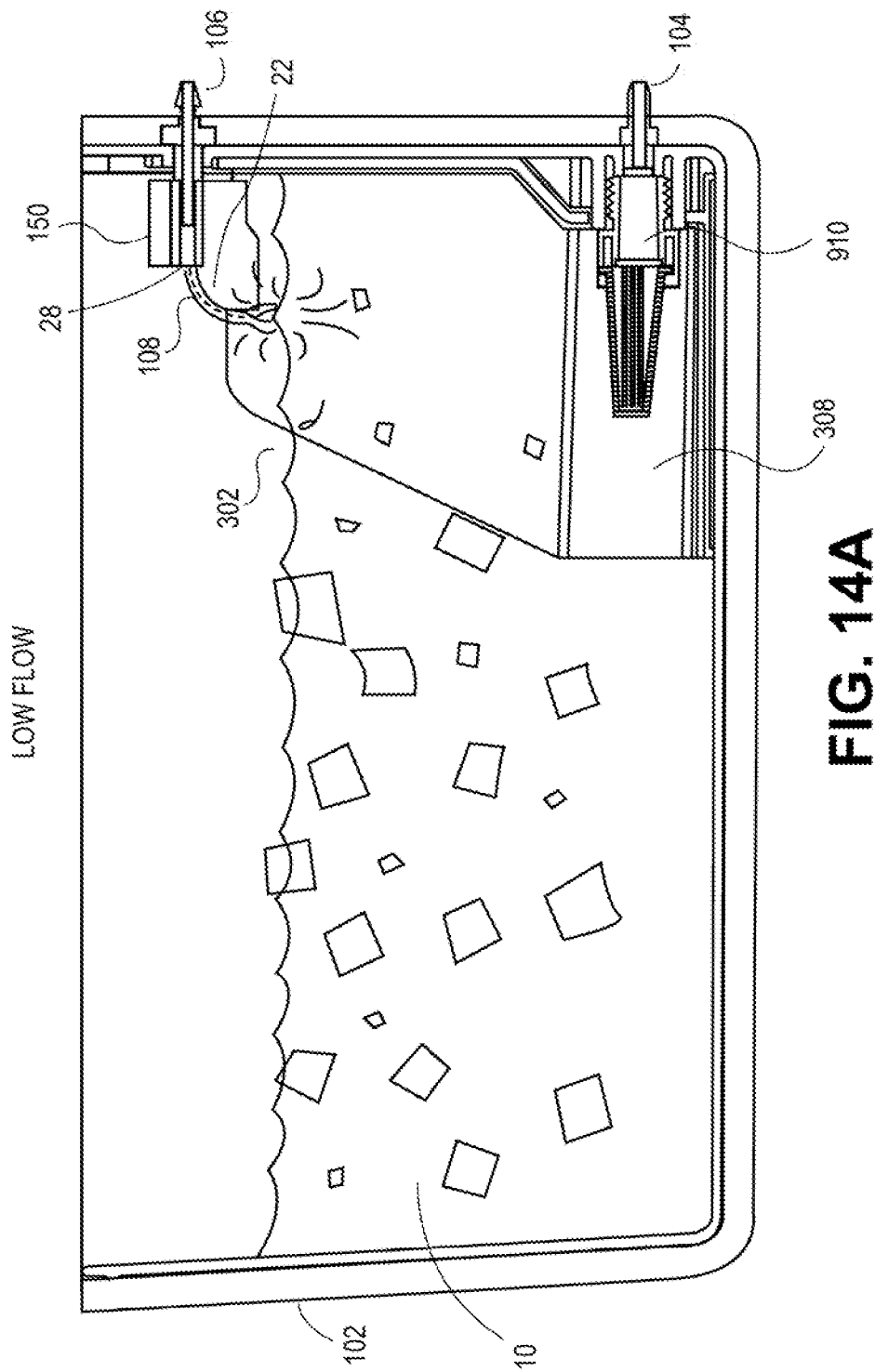
FIGS. 14A-14D illustrate a reservoir with a baffle and the variation of return flow at different flow rates for an inlet with a flow directing surface.
Figure 15A:
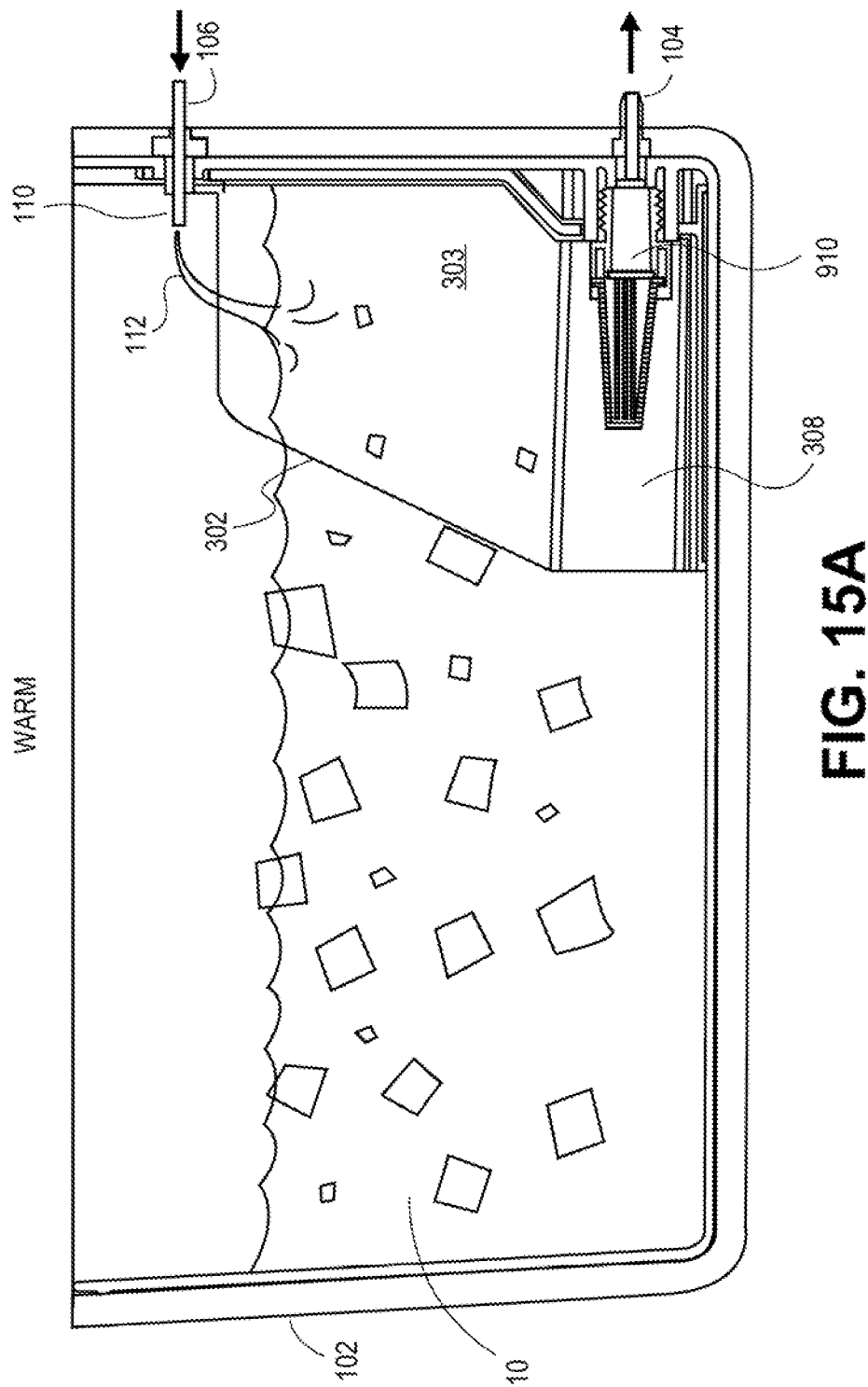
FIGS. 15A-15C illustrate a reservoir with a baffle and the variation of return flow at different flow rates for an inlet.
Figure 15B:
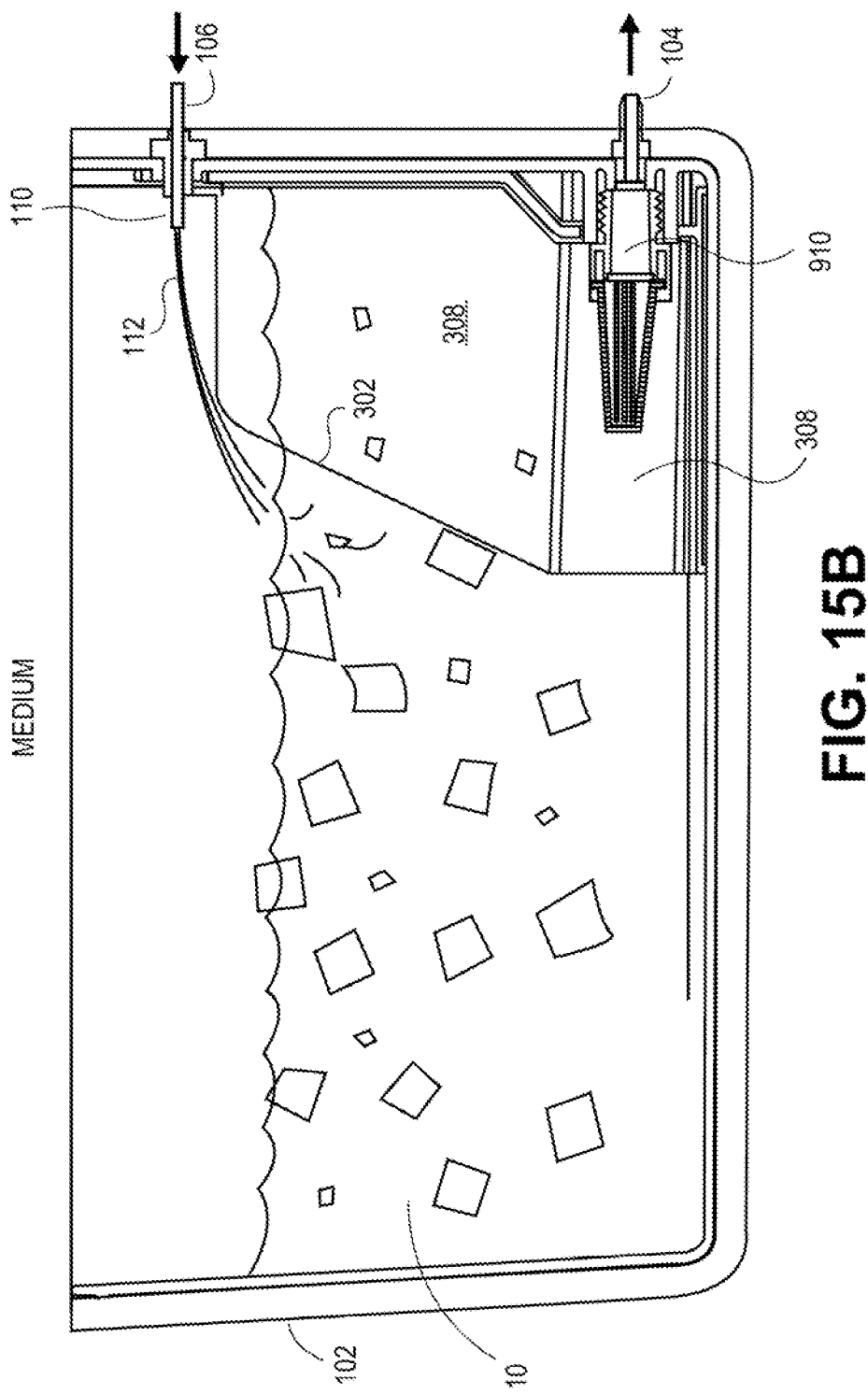
Figure 15C:
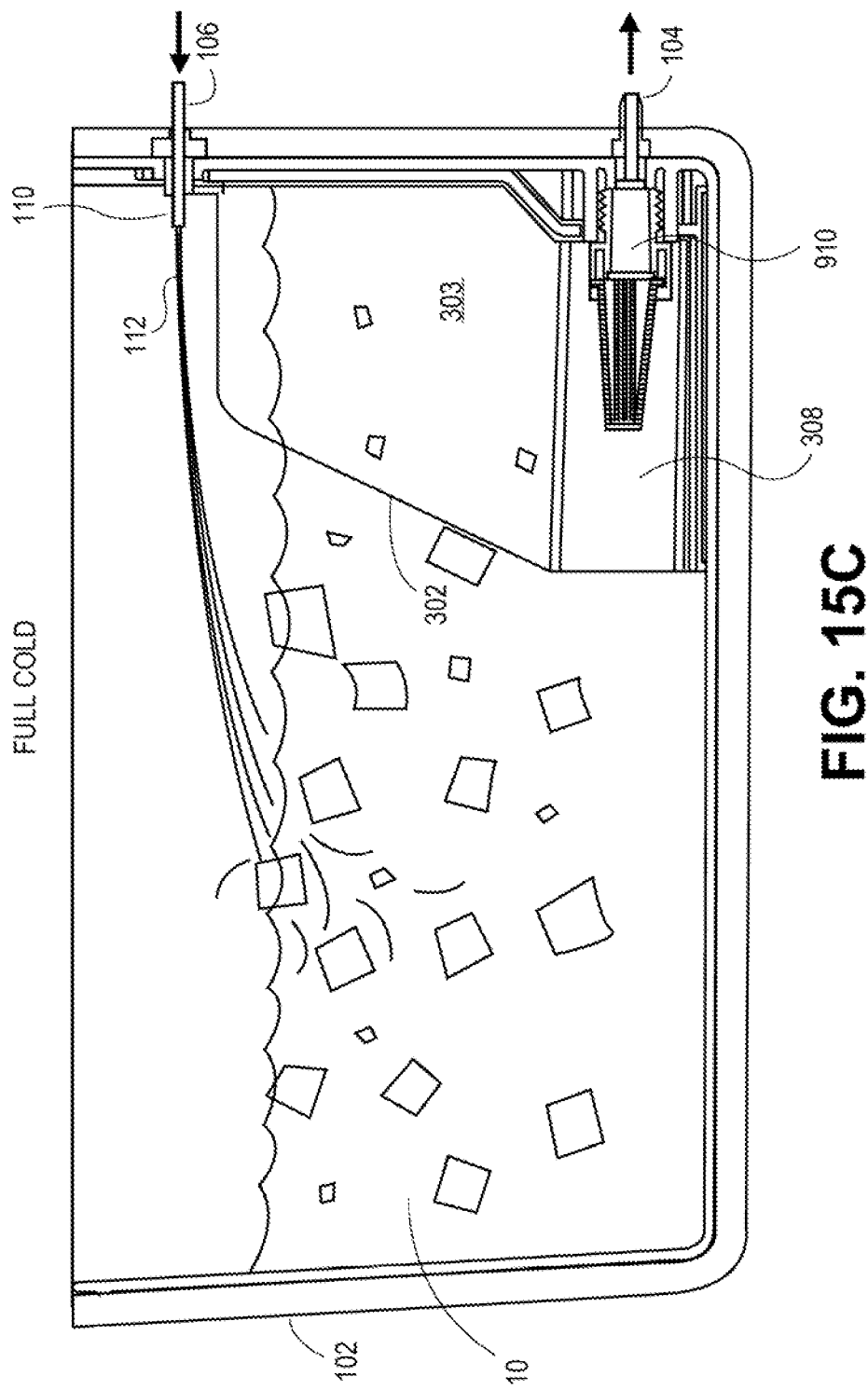

As illustrated in FIG. 14A, the flow rate of the return fluid 108 is shown exiting the reservoir inlet 106 through outlet 28 of the directed flow surface inlet 150. The directing surface or tongue 22 is shaped such that at low fluid flow rates, the fluid 108 runs over and around the tongue 22 and directed downwards towards the reservoir outlet 104 by both gravitational and surface tension forces. The tongue 22 assists in directing the flow 108 nearly directly downward towards the inlet at the bottom of baffle 302. In contrast, in FIG. 15A, the return fluid 112 flows out of pipe inlet 110 and is flows out of the reservoir outlet 104 and is directed downwards by only gravitational forces. While the flow 112 is also downward directed, it has a less direct flow towards the bottom of the baffle. The flow 112 is still between the baffle walls but is closer to flowing beyond the forward edge of the baffle wall (i.e., the edge furthest into the reservoir interior) than the flow 108.

The Intermediate Flow Condition

Figure 14B:
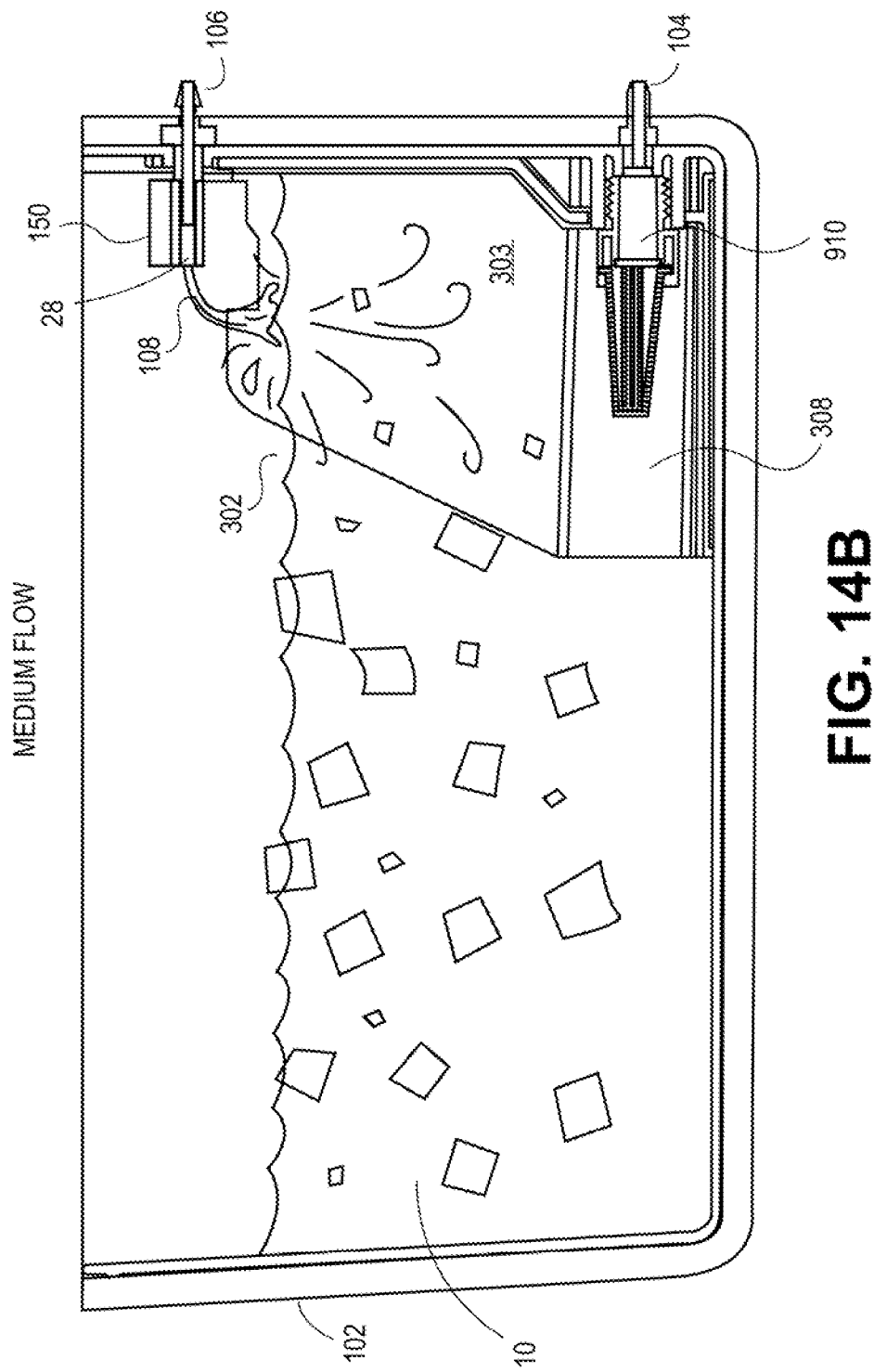
Figure 14C:
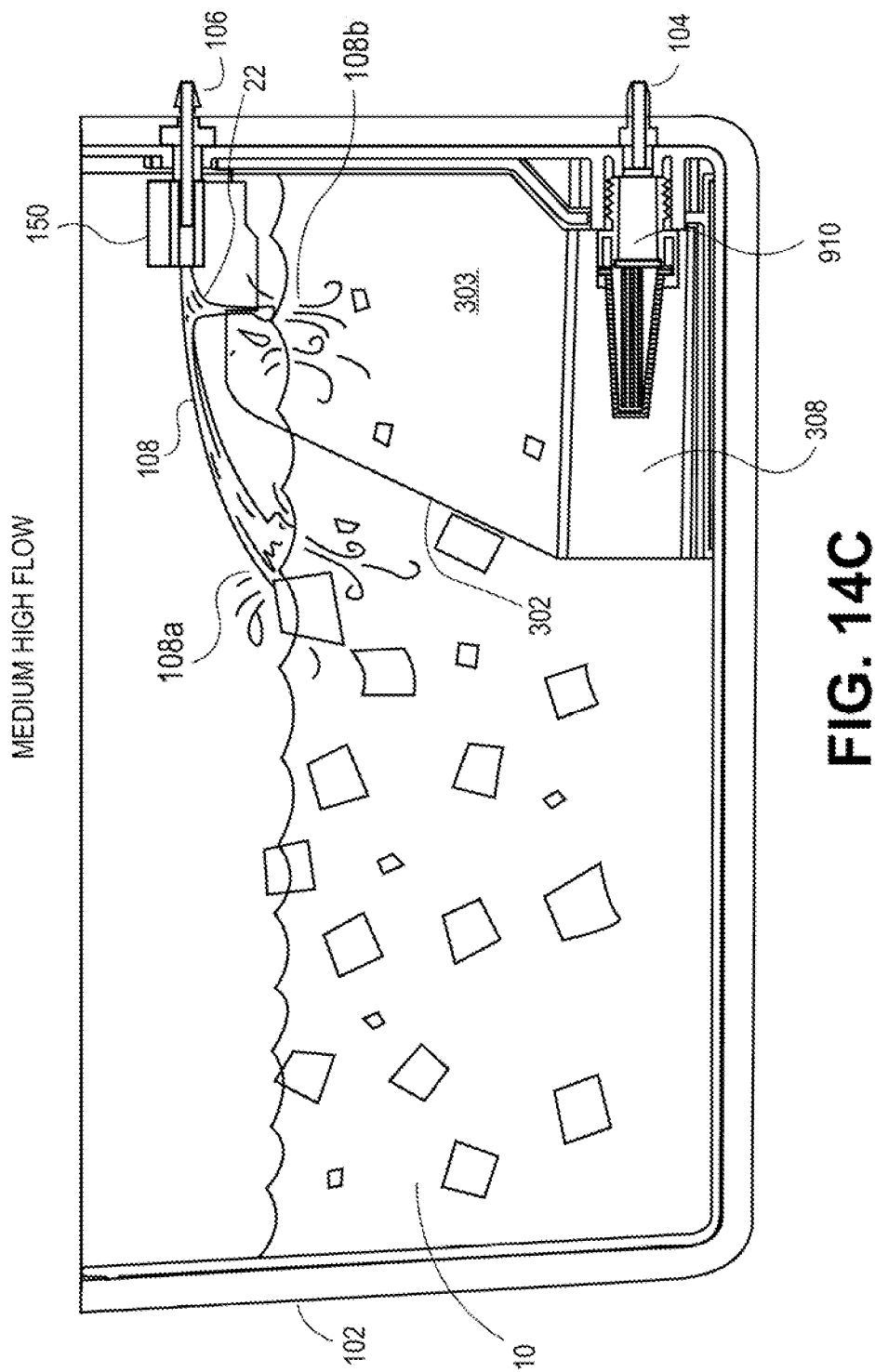
Figure 14D:
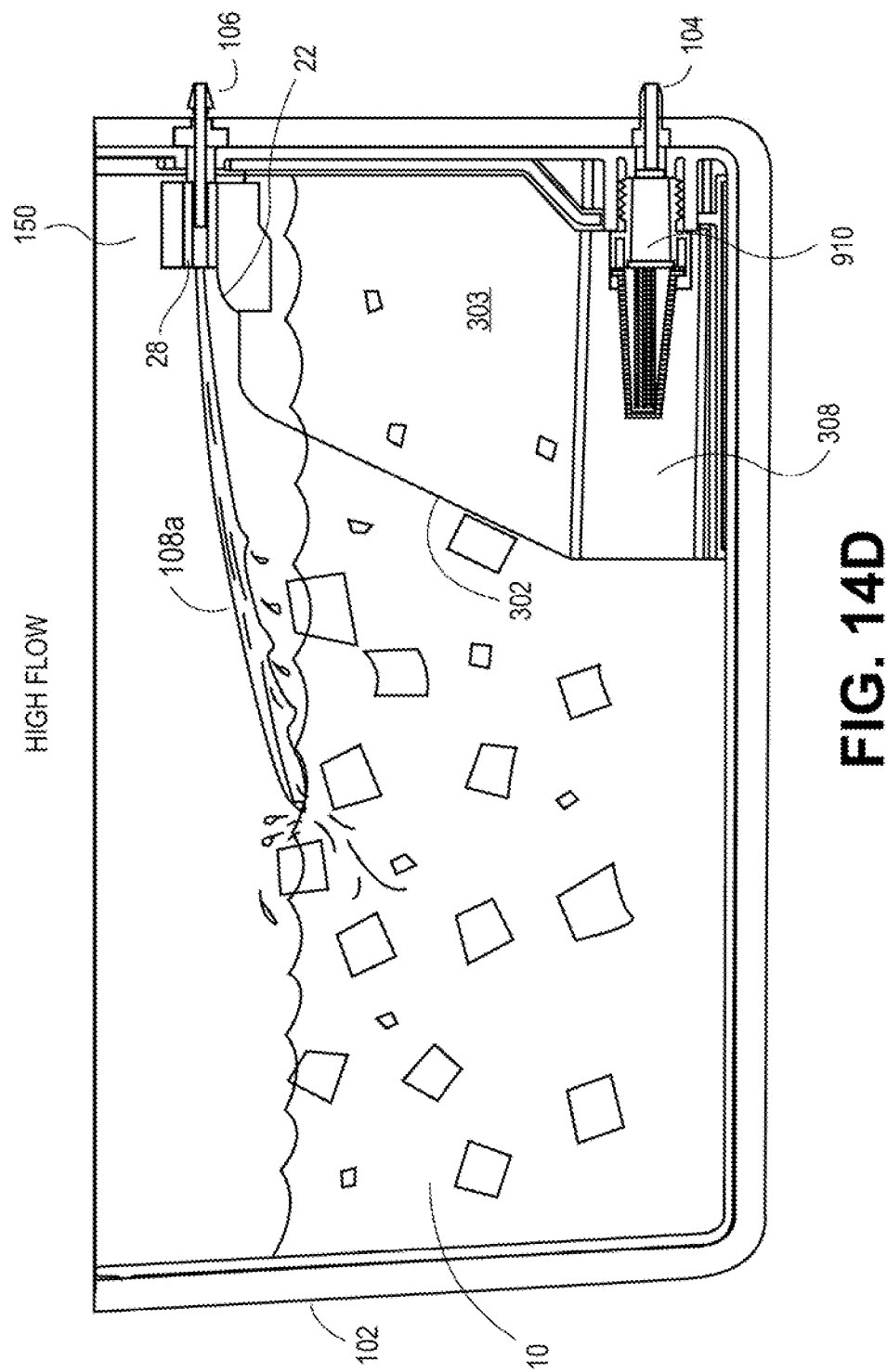

In FIG. 14B, return fluid 108 exits the reservoir inlet 106 through outlet 28 of the directed flow surface inlet 150. The shape of tongue 22 is such that even at medium fluid flow rates, the surface tension between the return fluid 108 and the tongue 22 maintains control of the direction of flow 108. As with FIG. 14A, the flow 108 is directed downwards towards the reservoir outlet 104. However, in FIG. 15B, the return fluid 112 the return fluid 112 flows out of pipe inlet 110 and is flows out of the reservoir outlet 104 and is directed downwards by only gravitational forces. As a result of the higher flow rate, the flow 112 is now less downwardly directed; it has a less direct flow towards the bottom of the baffle. The flow 112 is now beyond the baffle walls and entering the reservoir interior more towards the middle as opposed to the downwardly directed flow 108 in FIG. 14B.

The Medium High Flow Condition

In FIG. 14C, the increased fluid flow rate is beginning to overcome the surface tension between the fluid and the tongue 22. As a result, the fluid flow 108 is separating reflecting the decreasing influence of the tongue 22 at higher flow rates. A fluid flow portion 108a is projected further from the outlet 28 and beyond the baffle wall. The fluid flow 108a reflects that portion of the flow 108 that is free from the surface tension of tongue 22. Another fluid portion 108b maintains under the influence of the surface tension of tongue 22. As a result, the fluid flow 108b remains directed downwards towards the reservoir outlet 104 and the bottom of the baffle 302.

In FIG. 15C as with FIG. 15B, the increasing flow rate continues to project the fluid return 112 beyond the baffle wall and still further directed into the reservoir interior.

The High Flow Condition

In FIG. 14D, the increased fluid flow rate has now overcome the surface tension forces created by tongue 22. As a result, the return flow 108 is no longer separated into an outwardly projected flow 108a and downward flow 108b as in FIG. 14C but is instead entirely an outwardly projected flow 108a. In the case of both the inlet 110 and the directed surface inlet 150, further increase in flow rate will continue to direct the trajectory of the return flows 108, 112 beyond the baffle walls towards the reservoir interior. In both cases, the return fluid 112, 108 enters far from the reservoir outlet 104, thus minimizing the warming of the reservoir water most proximal to the reservoir outlet 104.

Another method to improve the performance of the thermal therapy device provides return stream vector control with a moving or movable inlet for directing the return stream within the reservoir interior. A movable inlet may direct the return flow in the direction of the reservoir outlet in order to keep the return fluid proximal to the reservoir outlet. When the warmer return water lands closer to the reservoir outlet, the water surrounding the reservoir outlet is warmed. The fluid flow rate may not need to be reduced. Instead, temperature control adjustments may be provided by adjusting the direction, orientation or attitude of the incoming fluid by moving the movable inlet to change the direction of the return stream.

As used herein, the return stream vector control enabled by the moving inlet is used to create temperature gradient/isotherms in the reservoir. The motion of a movable inlet may be provided in a number of different configurations including mechanical structures that provide movement such as pivoting structures, rotating structures, twisting structures and/or bending structures.

Still further, the inlet may be activated by physically changing conditions or further may be mechanically or electrically activated. Alteration of the tongue or deflection of an inlet may be accomplished by a number of different configurations either directly by the user or by a controller executing instructions or based on input from a user. A suitable actuator may be positioned alongside, on, within or in any other suitable orientation to cause deflection or controlled movement of the tongue or the inlet by the actuator. The deflection or movement of a tongue or inlet may be towards or away from a component in a reservoir or a portion of a reservoir.

Additionally or alternatively, the inlet may be moved by deflecting or manipulating all or part of the inlet in order to impart the desired directionality of the return flow from the inlet relative to the reservoir interior and/or components within the reservoir interior. Examples of inlet moving structures include linkages, rods, lines or other connectors attached between the proximal and distal ends of the inlet whereby the degree of movement of the linkage, rod, line or connector determines the amount of inlet flexion, bend or directionality imparted to the inlet.

Additionally or alternatively, the degree of inlet movement or deflection in a movable inlet is provided a suitably positioned actuator. An actuator includes any of a magnetic, electrical, electro active, mechanically or pneumatically operated structure positioned to interact with the inlet to provide the desired flexion or movement of the opening 28 relative to the reservoir interior or a structure within the reservoir interior. In one aspect, the actuator may include a shape memory alloy structure positioned relative to the inlet whereby the degree of activation of the shape memory alloy structure corresponds to the amount of inlet flexion, bend or directionality imparted to the inlet.

In still other additional alternatives, moving inlets may be used in combination with biasing structures. The biasing structure may be used to align the inlet with a preferred inlet direction. Actuation of the inlet movement device, structure or mechanism would then be used to overcome the bias condition and deflect the moving inlet. Once the movement device, structure or mechanism is removed, the bias would return the inlet to the preferred inlet direction.

Figure 18:
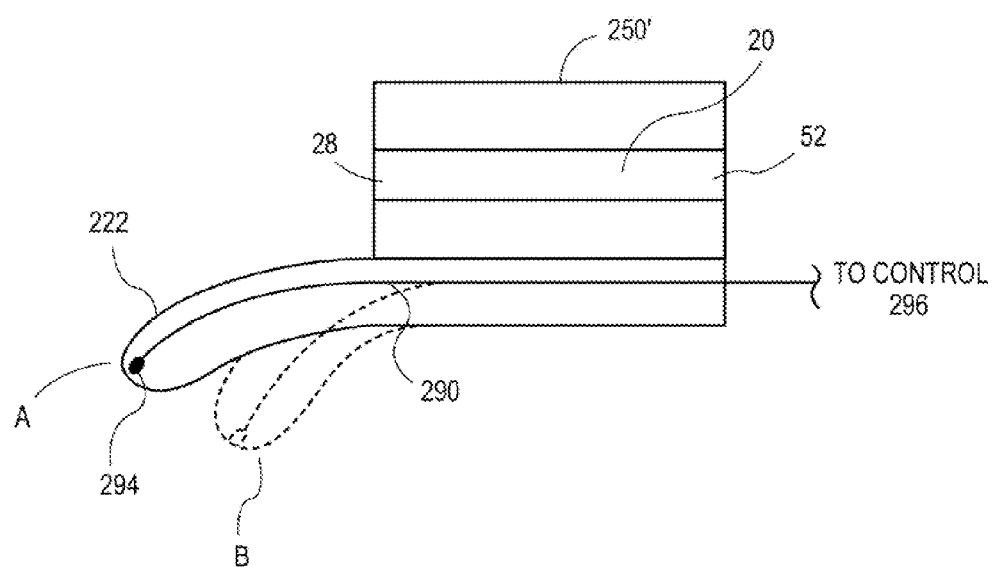
FIG. 18 illustrates a movable inlet configured with a variable flow directing surface.

FIG. 18 is a section view of an inlet 250' having a tongue 222 positioned adjacent the opening 28. An actuator 290 extends within the tongue 222 to a connection point 294 near the distal end. When the actuator 290 is not active, the tongue assumed a rest state A. When the actuator 290 is engaged or actuated, the tongue 222 deflects into state B. A control 296 is provided proximal to the inlet 250' and is connected to a controller or for use by a user. In one aspect, the actuator 290 is a wire connected at 294 to the tongue 222. In this aspect, the control 296 is a knob or handle.

Figure 19:
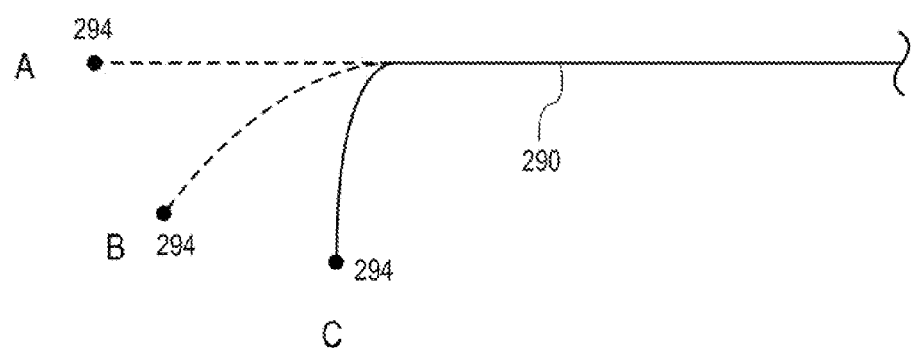
FIG. 19 illustrates an exemplary actuator for use with a movable inlet.

In another alternative shown in FIG. 19, the actuator 290 is a shape memory actuator (SMA) and the control 296 is a suitable electronic control and power system used for the controlled actuation of SMA. In this aspect, the SMA actuator 290 has a biased, inactive condition shown in condition A. As the SMA is actuated and it begins to deflect, it may curve into the bend shown in state B or be nearly downward in state C. In an embodiment of the tongue 222 when the actuator 290 is an SMA actuator, then the tongue could be altered by actuation of the SMA from a resting configuration (state A) to various bent configurations, for example states B and C. It is to be appreciated that the bias condition could be reversed such that the tongue 222 remains in state C when the SMA actuator 290 is inactive and actuation of the SMA actuator 290 produces states B and C.

Figure 20:
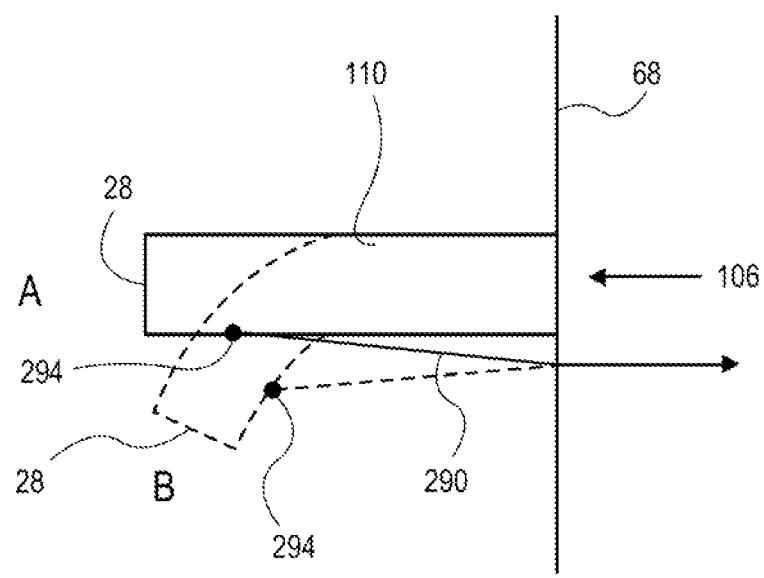
FIG. 20 illustrates a movable inlet in a straight configuration with a bend configuration in phantom.

FIG. 20 illustrated an inlet tube 110 connected to an actuator 290. The actuator 290 is connected near the distal end at point 294. When the actuator is not active, the inlet tube 110 is in a generally straight configuration as illustrated by state A. When the actuator 290 is active, the tip of inlet 110 or the opening 28 is aligned downwardly as indicated in state B (in phantom). In this illustrative embodiment, the actuator 290 is a pull wire. Other types of actuators may be used to deflect, bend or alter the position of an inlet in the systems described herein. The manner of actuation may depend upon the type of actuator 290 selected. Appropriate user interfaces, input devices, controls, power supplies and electronic support are provided to operate an actuator as described herein.

Figure 20A:
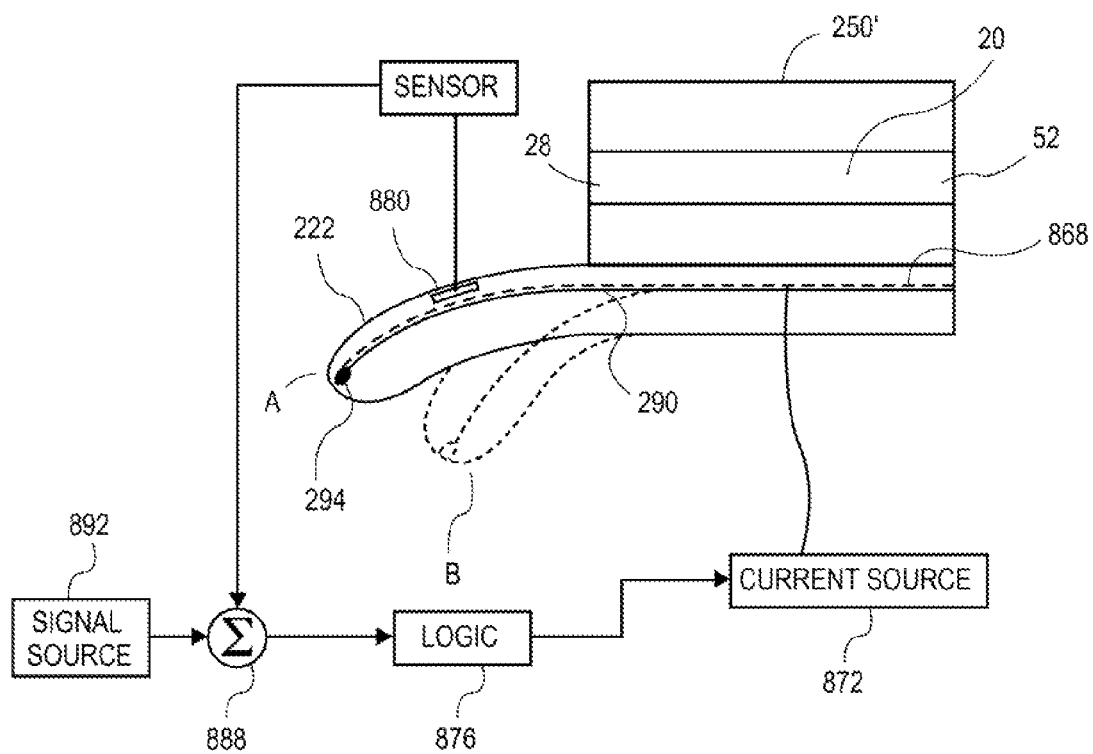
FIG. 20A illustrates a movable inlet with a tongue configured for movement by a shape memory alloy (SMA) element with a schematic representation of an exemplary SMA control system.

Referring to FIG. 20A, in one embodiment, the actuator 290 extending through tongue 222 comprises a shape memory alloy element 868 extending along the length of the actuator 290. Actuation (i.e. controlled deflection) of the actuator 290 can be controlled by the amount of electric current applied to the shape memory element 868. As electrical current is applied to the shape memory element 868, the shape memory alloy is heated above its activation temperature, allowing it to move towards its previously memorized shape. When the electrical current is removed, the shape memory alloy is cooled, preventing further movement of the actuator 290. Thus, an electrical current source 892 can be is coupled to the shape memory element 868 to selectively supply electrical current thereto. A control system can be configured to vary the amount of current supplied to the actuator, which will in turn vary the degree to which the actuator changes shape and thus the degree to which the tongue 222 is bent or deflected.

Referring still to FIG. 20A, a feedback control system can optionally be included to control the bending of the tongue 222. A strain gauge 880 can be located on the tongue 222. A sensor circuit 884 can produce a signal whose magnitude is indicative of the strain to which the tongue 222 is subjected, and this signal can be supplied to a summoning circuit 888. A signal source 892 can also supply a signal to the summoning circuit 888 in which the signal's value represent a degree of bending desired for the tongue 222. The summing circuit 888 can effectively compare the two input signals and, if there is a difference, signal the logic circuit 876 as to the amount of this difference. The logic circuit 876 can, in turn, signal the current source 872 to cause further bending (or unbending) of the tongue 222 so that the output signal of the sensor 884 will move closer in value to the signal supplied by the signal source 892. This feedback control system can ensure that the tongue 222 is bent as desired. A feedback circuit for a bending actuator is described further in U.S. Pat. No. 5,933,002, which is hereby incorporated by reference. In particular, the feedback system described by FIGS. 6 and 8 of U.S. Pat. No. 5,933,002 could be included as part of the actuator 290 described herein.

Figure 20B:
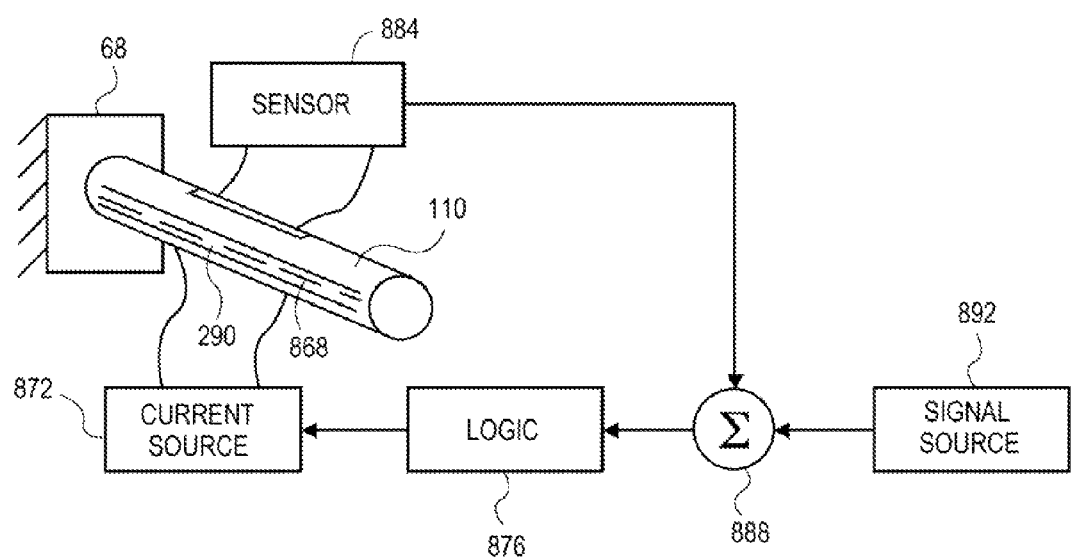
FIG. 20B illustrates a movable inlet configured for configured for movement by a shape memory alloy (SMA) element with a schematic representation of an exemplary SMA control system.

Referring to FIG. 20B, the actuator 290 extending along the inlet 110 can, similar to the embodiment of FIG. 20A, include a shape memory element 868 and/or a feedback control system. The shape memory element 868 can cause actuation of the actuator 290 to controllably bend the inlet 110. Similar to the embodiment of FIG. 20A, the feedback control system can be used to ensure that the desired amount of bending is obtained.

Figure 20C:
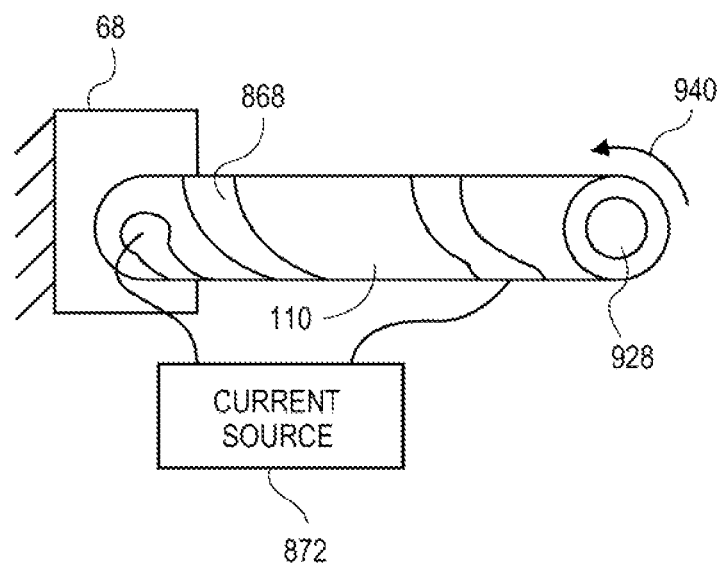
FIG. 20C illustrates a movable inlet configured for configured for movement by a shape memory alloy (SMA) element wrapped about the inlet.

The shape memory element 868 need not be linearly aligned with the inlet 110 or the tongue 222. Rather, the shape memory element 868 could be aligned off-axis or helically wound to allow the tongue 222 or inlet 110 to bend in different directions. For example, referring to FIG. 20C, the shape memory element 868 could be helically wound around the inlet 110. Supplying current to the helical shape memory element 868 of FIG. 20C can selectively cause a change in shape of the shape memory element to thereby cause a twisting of the inlet 110 in the direction indicated by the arrow 940.

Moreover, the shape memory element 868 of the various embodiments described herein could include a plurality of shape memory portions allowing the tongue 222 or inlet 110 to move in a variety of directions. Further, the shape memory element 868 can include a pair of antagonistic shape memory portions to allow the inlet 110 or tongue 222 to be controllably moved in one direction and in the opposite direction. Antagonistic shape memory elements are described further in U.S. Patent Publication No. 2003/0199818, which is hereby incorporated by reference. In particular, the first and second actuator members 52, 54 shown in FIG. 1 of U.S. Patent Publication No. 2003/0199818 could be included as part of the shape memory element 868 described herein.

Figure 21B:
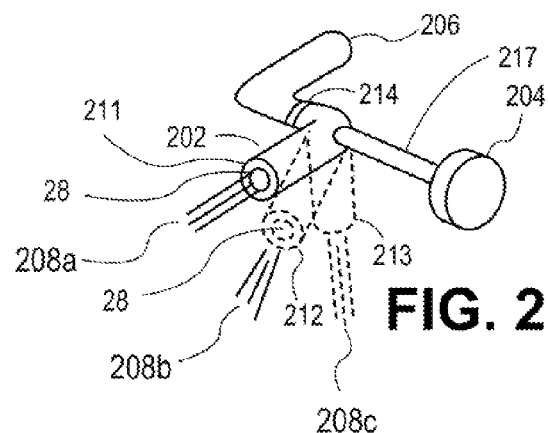
FIG. 21B is an enlarged view of the movable inlet of FIG. 21A.
Figure 21A:
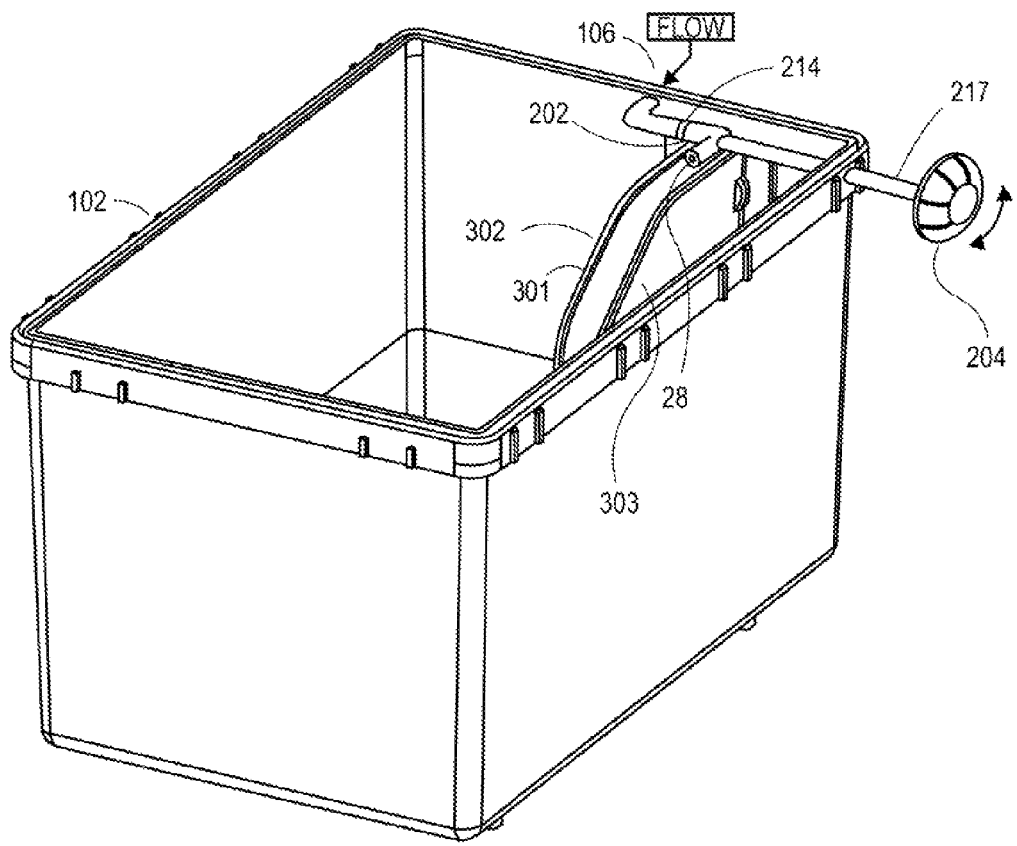
FIG. 21A illustrate an isometric view of a reservoir having a movable inlet used in conjunction with a baffle.

FIGS. 21A and 21B illustrate an embodiment of a moving inlet 202 in a reservoir 102. In FIGS. 21A and 21B, the moving inlet 202 includes a pivoting structure 214. The moving inlet 202 directs fluid flow from the reservoir inlet 106 via opening 28 into the reservoir 102. The reservoir inlet 106 is connected to the moving inlet 202 via pivoting structure 214. The pivoting structure 214 may be a sealed swivel hinge connection or another type of connection configured to allow movement of the moving inlet 202. The moving inlet 202 may pivot, rotate or move in any direction by altering the location of the pivoting structure 214 and its relationship to the inlet 202, the reservoir 102 or a structure within the reservoir 102, such as a baffle.

In particular with the embodiments of FIGS. 21A and 21B, the moving inlet 202 pivots from a horizontal position 211 generally along longitudinal axis to downwardly directed positions 212, 213. In the illustrated embodiment, a rotation mechanism, here a knob 204, is provided to adjust the deflection amount of moving inlet 202. The rotation mechanism 204 is connected to the pivoting structure 214 using shaft 217 or other suitable connector.

Figure 22A:
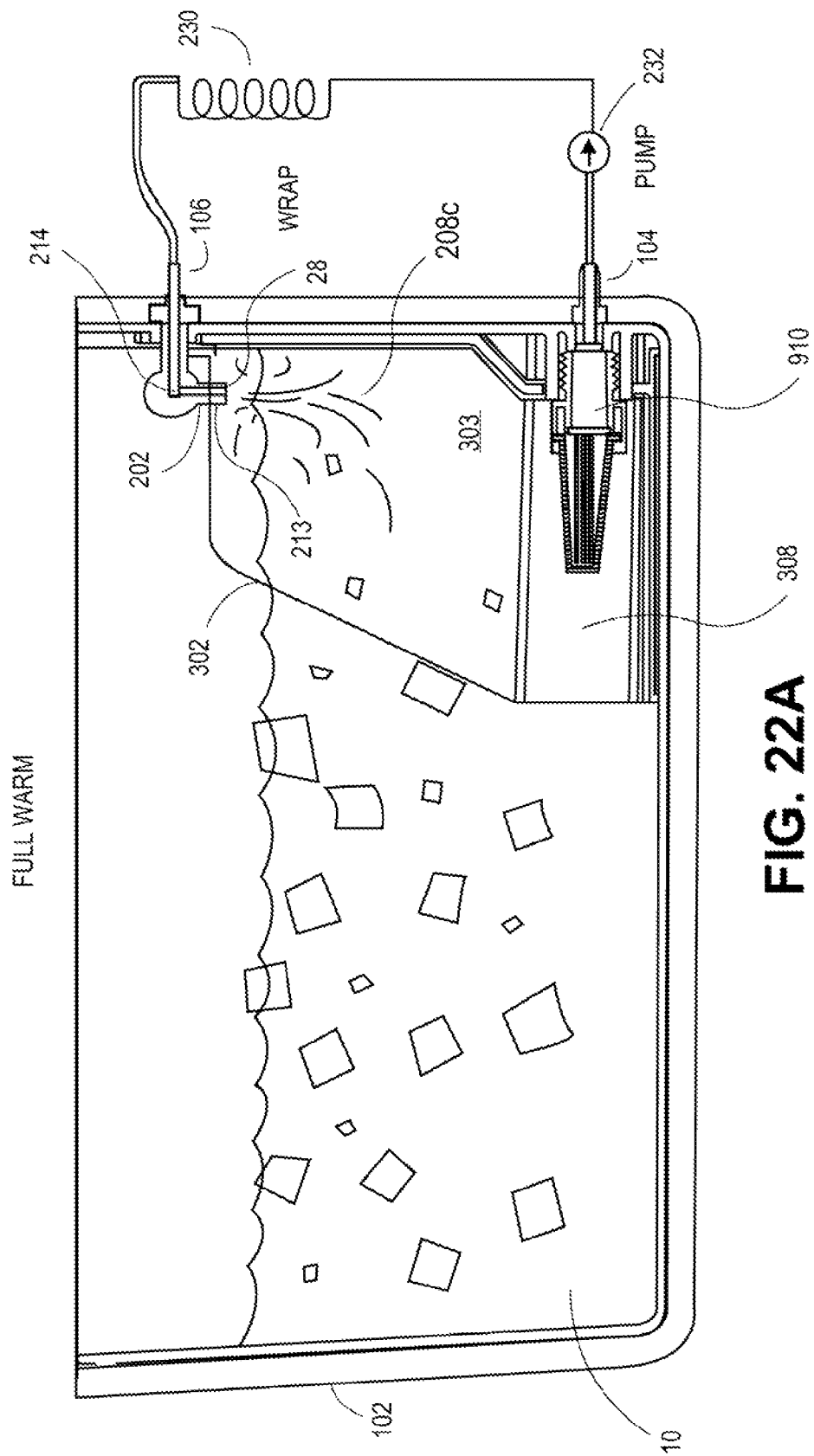
FIGS. 22A-22C illustrate the operation of a control system having a reservoir with a baffle and movable inlet used in cooperation.
Figure 22B:
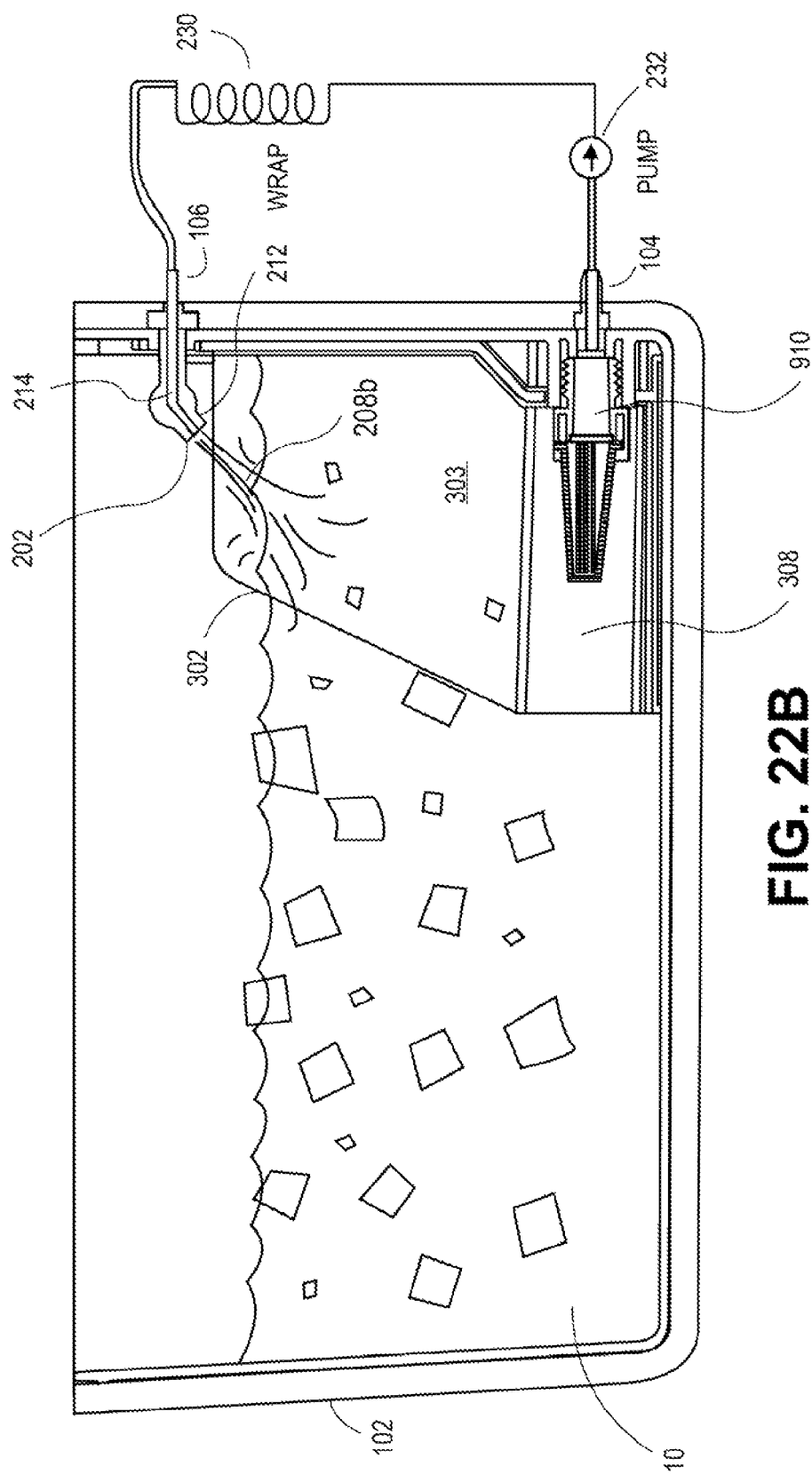
Figure 22C:
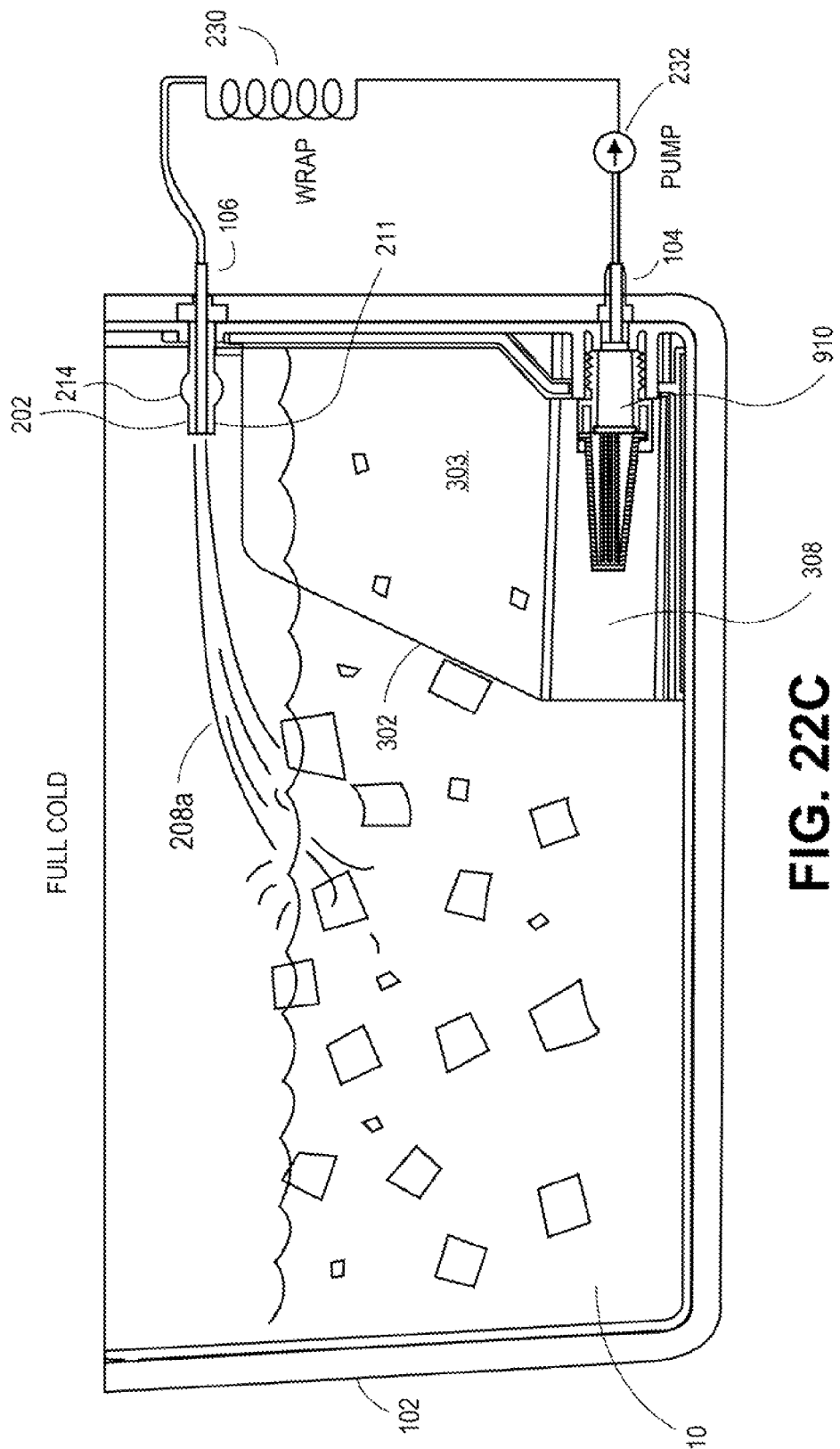

FIGS. 22A-22C illustrate embodiments of the return stream vector control with the moving inlet 202 shown in FIG. 21B in the context of a reservoir 102. FIG. 22A illustrates warmer water returning from the wrap 230 through the moving return 202 in position 213. In position 213, the return flow 208c is directed downward towards the bottom of baffle 302 and the outlet 104. FIG. 22B illustrates the moving inlet 202 position in flow position 212. When in flow position 212, the return flow 208b is directed towards the outer walls of the baffle towards the more central portion of reservoir 102. FIG. 22C illustrates the moving inlet 202 in flow position 211. In flow position 211 the return flow 208a is directed clear of the baffle walls towards the more central portion of the reservoir 102. In FIG. 22B and FIG. 22C, warmer water is directed farther away at different angles from reservoir outlet 104. FIGS. 22A-22C illustrate one aspect of moving that is by the pivoting of the moving inlet 202 as indicated in the various positions 211, 212 and 213.

FIGS. 21A, 21B and 22A-C illustrate a configuration of the pivoting structure 214 that permits the moving inlet 202 to be deflected in a manner that maintains the return flow in the region of the reservoir generally between the baffle walls 301, 303. Other orientations are possible for the moving inlet to introduce the return flow into other positions.

Figure 23:
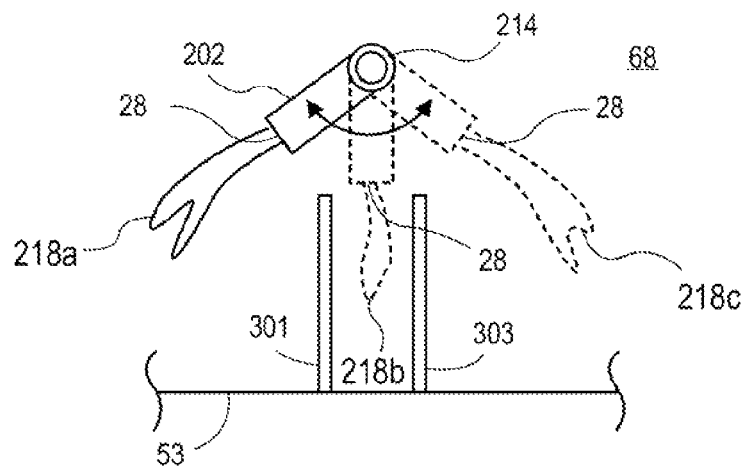
FIGS. 23 and 24 illustrate a movable inlet in different orientations with respect to a baffle.

FIG. 23 illustrates a view towards reservoir wall 68 and shows the alignment of the rotating structure 214 and moving inlet 202 relative to the top of baffle walls 301, 303. As shown in the embodiment of FIG. 23, operation of the rotating structure 214 causes the movable inlet 202 to direct outlet 28 to the side of wall 301 to produce directed flow 218a. The inlet 202 may be positioned between the walls 301, 303 to produce directed flow 218b. The inlet 202 may be positioned to the side of wall 303 to produce directed flow 218c. While moving relative to the baffles walls, the moving inlet 202 remains a generally downward directing orientation.

Figure 24:
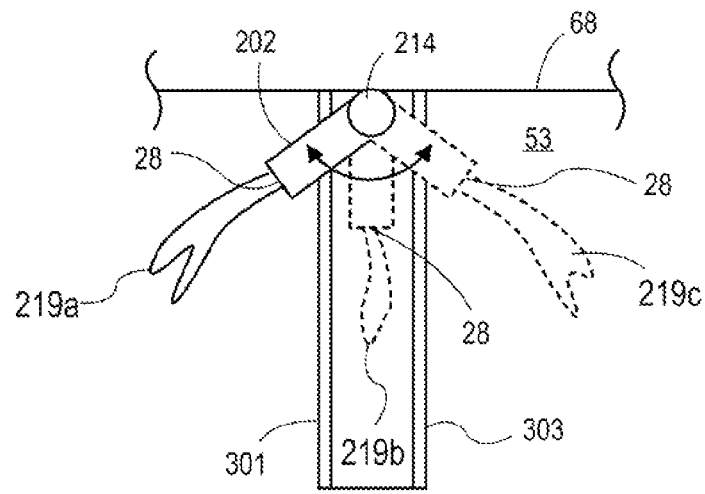

FIG. 24 illustrates a top down view towards a reservoir floor 53 of the movable inlet 202. The view of FIG. 24 shows the alignment of the rotating structure 214 and moving inlet 202 in a position above the top of baffle walls 301, 303. As shown in the embodiment of FIG. 24, operation of the rotating structure 214 causes the movable inlet 202 to direct outlet 28 to the side of wall 301 to produce directed flow 219a. The inlet 202 may be positioned between the walls 301, 303 to produce directed flow 219b. The inlet 202 may be positioned to the side of wall 303 to produce directed flow 219c.

Figure 25:
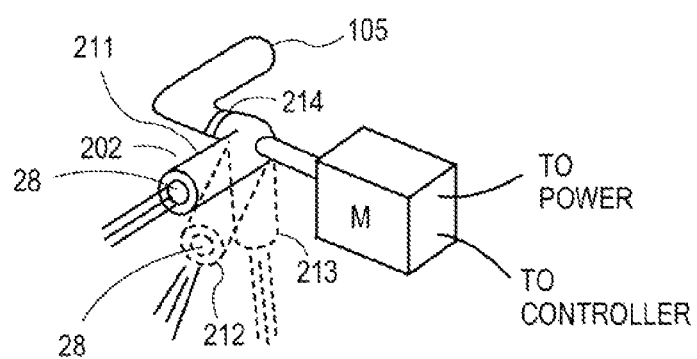
FIG. 25 illustrates the movable inlet of FIG. 21B configured for operation with a motor M.

The rotation mechanism 204 may be operated by the touch of a user or by mechanical and/or electrical operation. In one specific aspect, FIG. 25 illustrates a moving inlet 202 connected to a motor M via shaft 217. The motor M is connected to a suitable source of power. The motor M is in communication with a suitable controller. The controller for motor M may be a simple resistive dial. The dial may be labeled with an indicator showing inlet direction or angle of inlet deflection. Alternatively, the motor M is connected to a controller such as the controller 7 of the other all system. In this case, the controller will adjust the degree of inlet deflection as part of an overall system control scheme.

Figure 26:
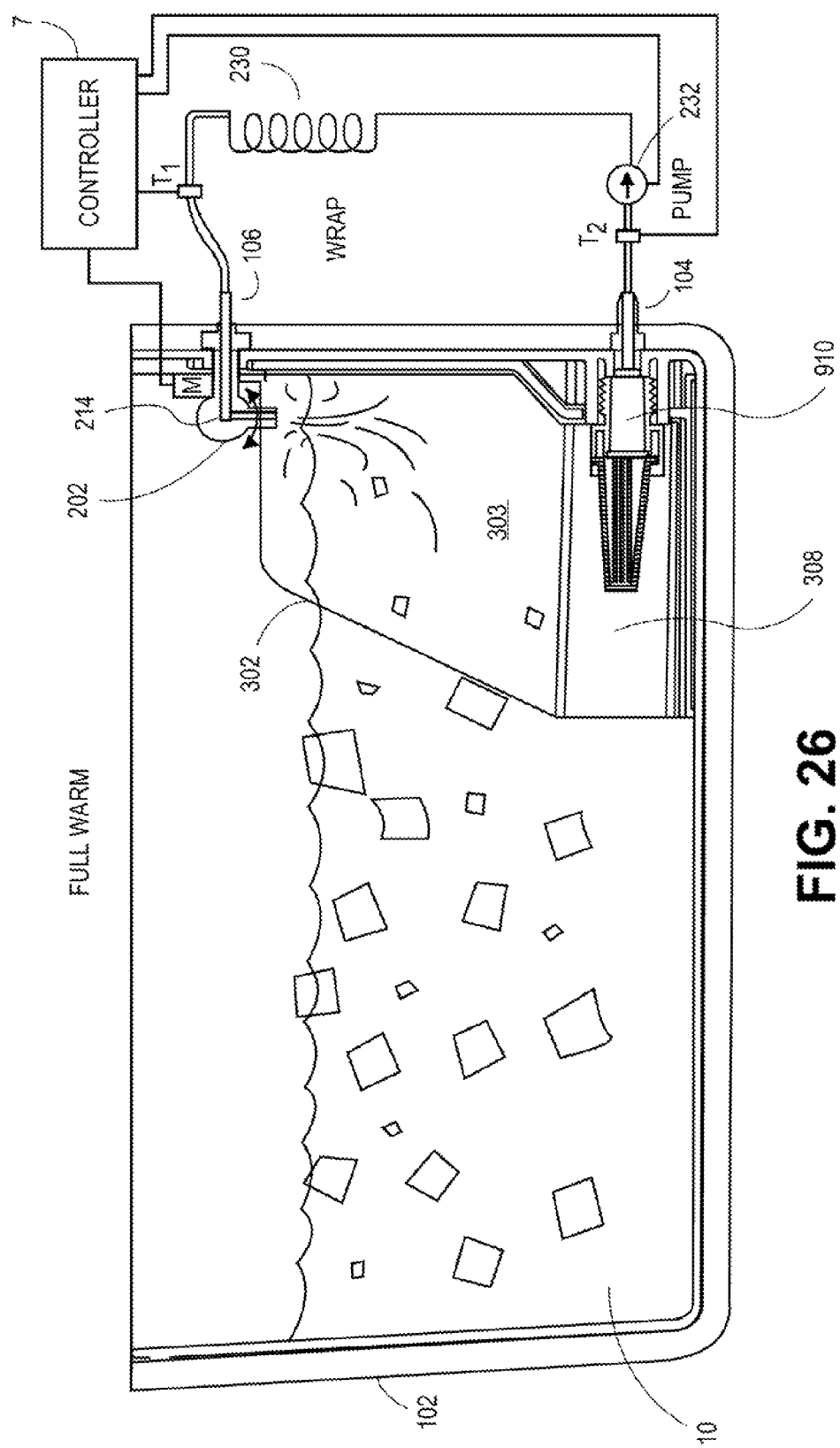
FIG. 26 illustrates the use of the movable inlet of FIG. 25 within a thermal therapy system.

FIG. 26 illustrates one exemplary thermal control system having a motor M configured to alter the position of a movable inlet 202. As shown in FIG. 26, the control system has a fluid circuit with a pump 232, wrap 230, reservoir 102, thermocouples T1, T2 and a movable inlet 214 driven by a motor M. In operation, the controller 7 receives inputs such as a temperature set point or other operational requirements along with information from sensors such as thermocouples T1 and T2 and produces outputs to control the operation of the pump 232 and the movable inlet 202 via the motor M.

Figure 27A:
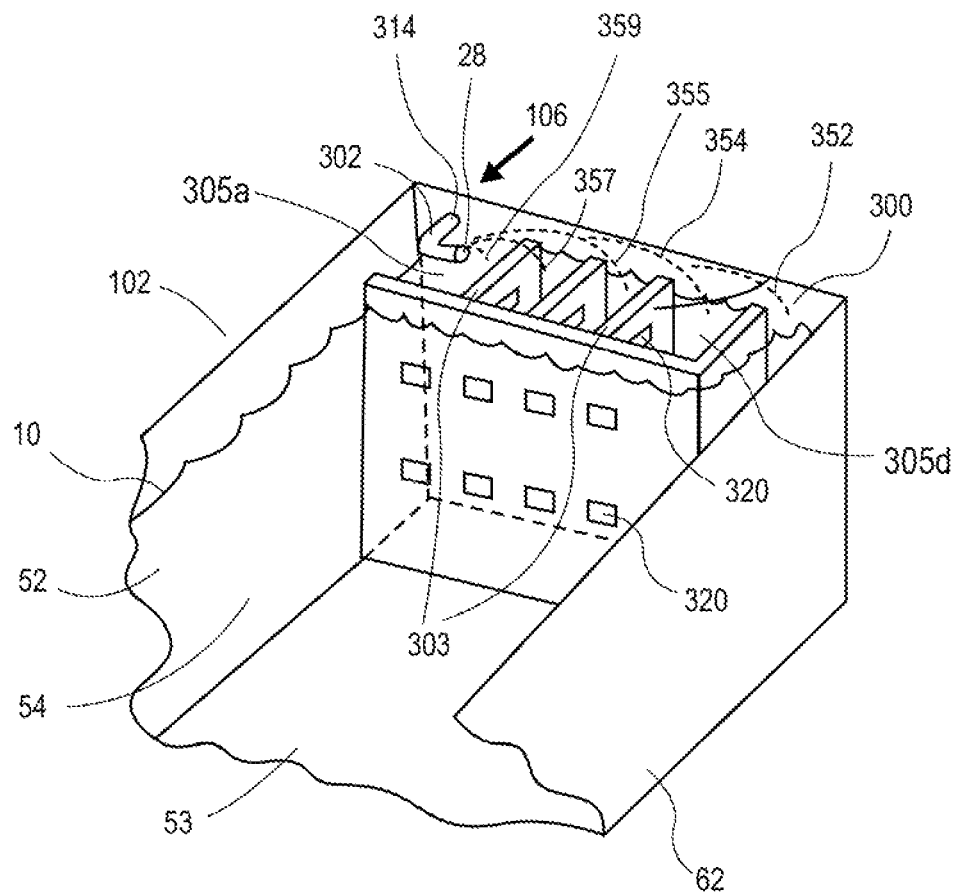
FIGS. 27A, B and C illustrate isometric, rear and side views of a multiple chamber baffle.
Figure 27B:
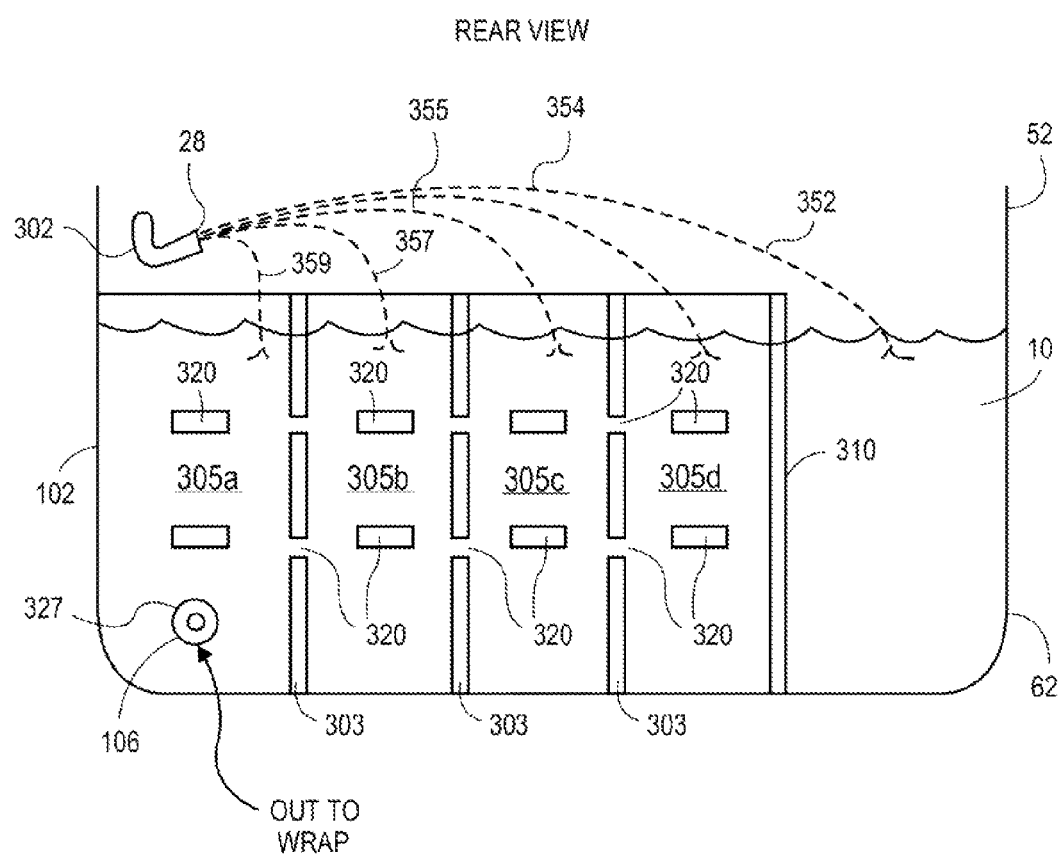
Figure 27C:
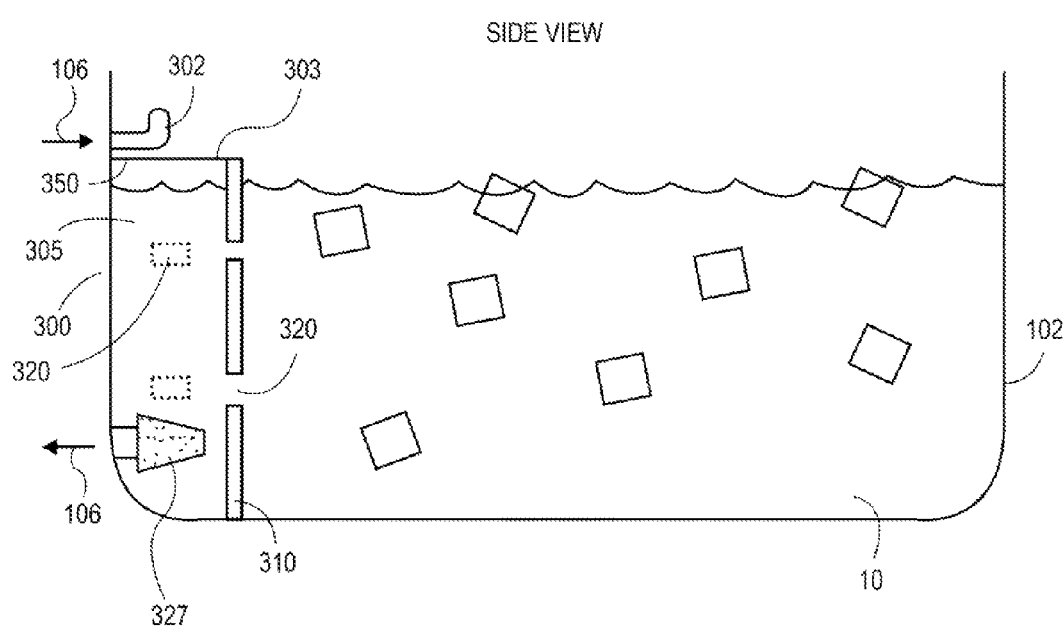

FIGS. 27A-C illustrate isometric, end and side views, respectively, of an embodiment of a multi-chamber baffle 300 in reservoir 102. The multi-chamber baffle 300 includes a chamber 305 formed by one or more outer walls 310 that separate the baffle chamber 305 from the reservoir interior. One or more dividing walls 303 may be used to partition the baffle chamber 305. As best seen in FIG. 27B, three dividing walls 303 are provided to create chambers 305a, 305b, 305c, and 305d. One or more openings 320 may be formed in the outer walls 310 and/or dividers 303. While only two, rectangular openings 320 of equal size are shown in the outer walls 310 for each of the chambers 305a-305d, more or fewer openings as well as different shape and size openings may be used. Similarly, while only two rectangular openings 320 of equal size are shown in the dividing walls 303, more or fewer openings as well as different shape and spacing of openings 320 may be used in the dividing walls 303.

The illustrated embodiment of multi-chamber baffle 300 is generally rectangular. One or more walls 310 may be used to form other baffle shapes. A single wall 310 may be curved about the inlet and outlet and attached to the same reservoir interior wall such that the baffle chamber 305 is formed from a single wall 310 in a generally curved shape. Alternatively, a baffle wall 310 may extend between two reservoir walls and an included corner to form a baffle chamber 305 of a generally triangular shape.

Also shown in FIG. 27B is the baffle 300 position within the reservoir on one side of the reservoir interior with the inlet and outlet along one side in the same chamber, here chamber 305a. Other inlet 302 positions are possible above any of the other chambers 305b, 305c or 305d. Moreover, the baffle 300 may be configured and positioned such that the inlet, and/or outlet are in different chambers by inserting addition dividing walls 303. Dividing walls are shown in a vertical orientation. Dividing walls 303 may be in horizontal orientations as well as angled orientations (i.e., orientations between vertical and horizontal orientations).

The inlet 302 of multi-chamber baffle 300 may be a fixed inlet or a moving inlet.

In the case of a fixed inlet, the inlet 302 is positioned within the chamber 305 at an inclined angle as best seen in FIG. 27B. The inclined angle is selected so that as flow speed changes, the fluid exiting opening 28 will be directed to various locations within the baffle chamber 305. In general, at slower flow speeds, the fluid leaving opening 28 remains closer to inlet 302. At higher flow speeds, the fluid leaves opening 28 and enters the chamber 305 at a greater distance from the inlet 302 in general proportion to the fluid speed.

The interaction of flow speed and discharge from inlet 302 is best seen in FIG. 27B. At a low speed, the fluid leaves opening 28 and follows fluid flow return path 359 into chamber 305a. At an increased speed, the fluid leaves opening 28 and follows fluid flow return path 357 into chamber 305b. At a still higher speed, the fluid leaves opening 28 and follows fluid flow return path 355 into chamber 305c. At a still higher speed, the fluid leaves opening 28 and follows fluid flow return path 354 into chamber 305d. At the highest flow speed, the fluid leaves opening 28 and follows fluid flow return path 352 beyond the baffle chamber 305 into the reservoir interior directly.

In the case of a moving inlet, the inlet 302 is positioned within the chamber 305 as described above. However, in contrast to the fixed inlet example, the moving inlet 302 includes a flex, joint, coupling or pivot to provide a change in the angle shown in FIG. 27B. The moving inlet 302 may be manipulated as with other moving inlet embodiments described herein to direct return flow to different portions of a multiple chamber baffle 300. The orientation, movement and control of the moving inlet 302 may be configured as described herein, by way of non-limiting examples, the configurations shown and described in FIGS. 18-20, 21A, 21B, 22A-22C, 23 and 24. The inclined angle of the moving inlet 302 is selected to complement or counteract the flow stream changes produced by changes in flow speed. As a result, changes in return flow direction as a result of flow speed changes as discussed above may be augmented or mitigated my adjusting the relationship of the moving inlet 302 to the baffle chamber 305.

Another method to improve the performance of a thermal therapy device is to provide robust mixing methods for cold temperatures. For instance, assuming ice fluid 10 is used in the reservoir 102, the reservoir temperature would be nearly 0° C. If the reservoir was well mixed with the warmer return fluid from the wrap 3, the reservoir outlet temperature would remain nearly 0° C. This would be ideal if the coldest possible wrap temperature is desired.

One exemplary mixing method includes adjusting the return flow stream to push ice towards reservoir outlet 106. The return stream may be directed in a number of different ways as further described in the embodiments that follow.

Figure 28A:
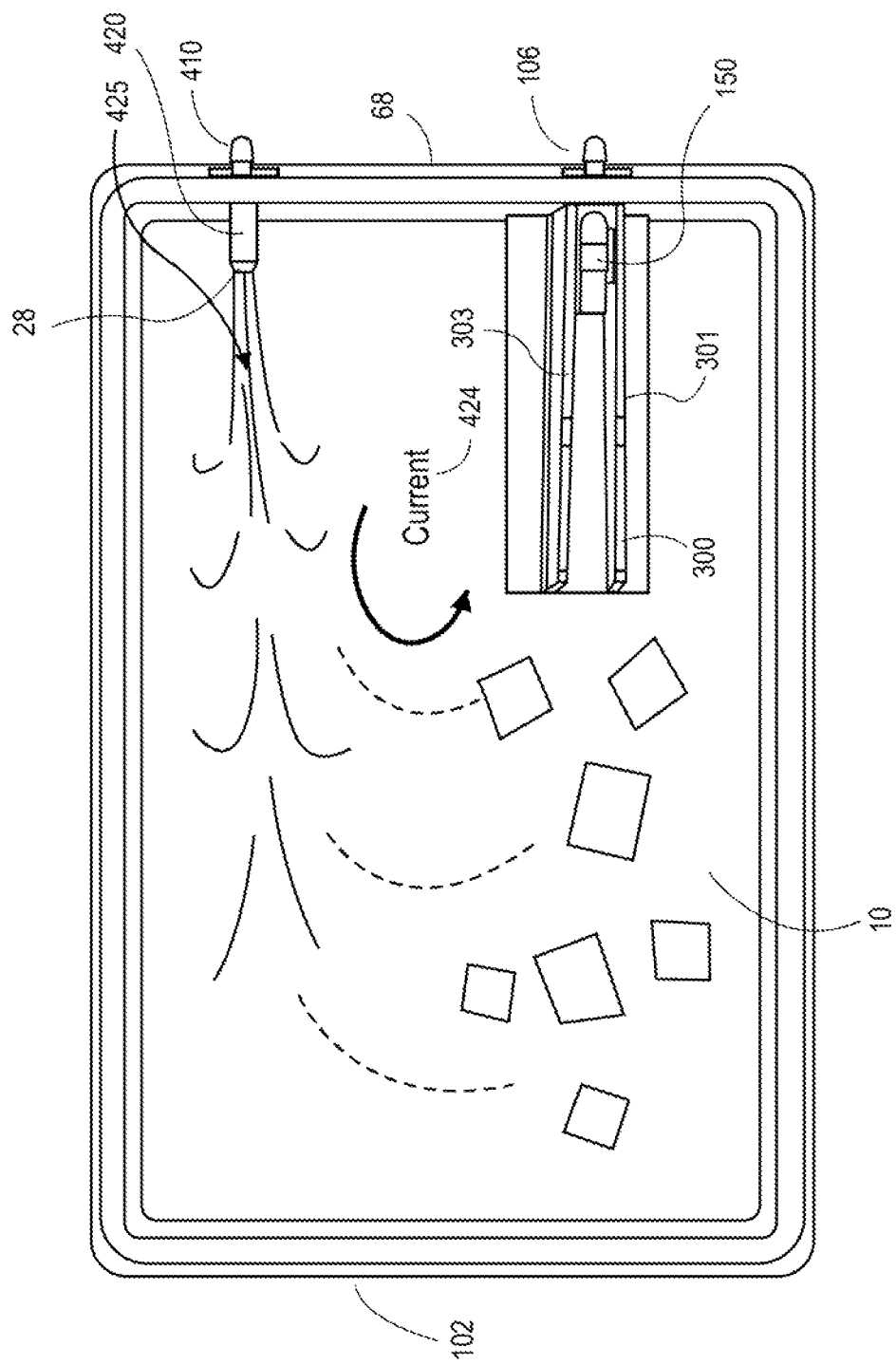
FIG. 28A is a top down view of a reservoir with a baffle and an an inlet displaced from the inlet associated with the baffle.
Figure 28B:
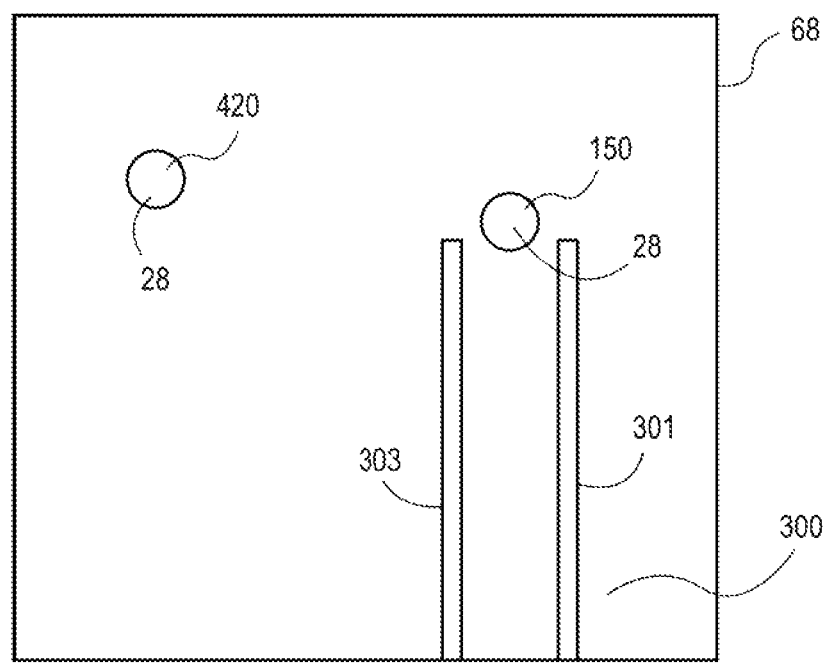
FIG. 28B is an end view of the reservoir in FIG. 28A showing the relative height and lateral separation of the inlets.

FIGS. 28A and 28B illustrate top down and partial end views, respectively, of a two inlet system. As best seen in FIG. 28A, two inlets are provided in different positions along the same wall, here reservoir wall 68. The two inlets are separated laterally (as shown in FIG. 28A) and are spaced about equally above the floor 53 (see FIG. 28B). The relative positions of the two or more inlets may be selected to create, alter or enhance a flow pattern or current within a reservoir interior.

In the illustrated embodiment, a first inlet is provided by an inlet 150 within a baffle 302 as described above. A second inlet 420 is provided as shown in a position laterally separated from the first inlet. The relative position of the openings 28 along wall 68 is best seen in FIG. 28B. The inlet 420 may be configured as a nozzle (i.e., reduced diameter within the inlet 420 directed towards the opening 28, see e.g., FIGS. 16 and 17). It is to be appreciated that any of the inlets embodiments described herein may be used to as the first inlet, second inlet or other inlets in a multiple inlet configuration.

In use, when a return fluid flow is directed to inlet 420, the resulting fluid stream 425 produces current 424 and the ice in the fluid mixture 10 to be pushed towards reservoir outlet within baffle 300. The return stream 425 from the wrap 3 may cause turbulence and mixing of the water of different temperatures. The return stream 425 may be a high velocity return stream (in the case of nozzle shown in FIG. 28A) in order to enhance the amount of turbulence created in the fluid mixture 10. One or more valves (not shown but described below) may be provided to adjust the amount of flow divided between the first inlet and the second inlet or alternatively to direct return flow to one of the first inlet or second inlet. The one or more valves may be under the manual control of a user or under the control of a system controller as described elsewhere in this application.

Figure 29:
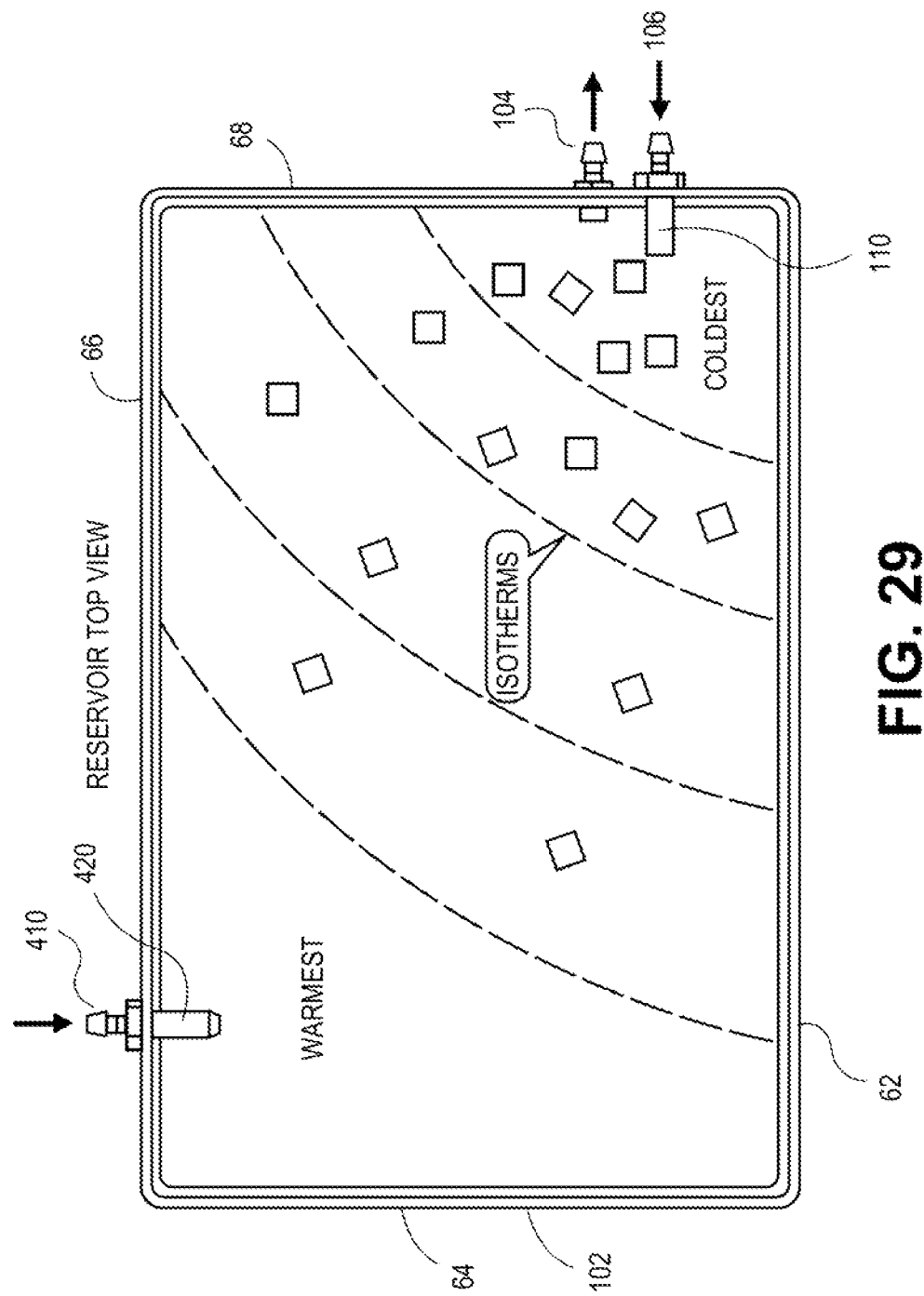
FIG. 29 is a top down view of a reservoir with an inlet on a wall different than the wall with the outlet.

An alternative multiple inlet configuration is illustrated in FIG. 29. In this embodiment, the first inlet is provided by the inlet tube 110. The inlet tube 110 connects the inlet 106 via reservoir wall 68 and is placed adjacent outlet 104 near where reservoir walls 68, 62 meet. The second inlet 410 is connected to nozzle inlet 420 though reservoir wall 66 near where walls 66, 64 meet. One or more valves (not shown but described below) may be provided to adjust the amount of flow divided between the first inlet and the second inlet or alternatively to direct return flow to one of the first inlet or second inlet. The one or more valves may be under the manual control or a user or under the control of a system controller as described elsewhere in this application. While illustrated without a baffle, a baffle may be used in conjunction with a multiple inlet system configuration.

In use, when a return fluid flow is directed to inlet 420, the resulting fluid stream produces current within the reservoir and the ice in the fluid mixture 10 to be pushed towards reservoir outlet 104. The return stream may cause turbulence and mixing of the water of different temperatures. The return stream produced in the configuration of FIG. 29 may be a high velocity return stream (in the case of nozzle shown in FIG. 29) in order to enhance the amount of turbulence created in the fluid mixture 10.

While the above embodiments describe multiple inlet embodiments with two inlets, the invention is not so limited. In some aspects, more than two inlets may be provided and the placement of the inlets may be along walls other than the same wall (FIG. 28A) or adjacent walls (FIG. 29). Moreover, the embodiments of the present invention have been described with regard to generally rectangular reservoirs 102. Other reservoir shapes are possible and will be described in the examples that follow.

FIG. 30A is a top down view of a rectangular reservoir 102 having walls 68, 62, 64 and 66. An outlet 104 is shown in wall 68 about midway between walls 66 and 62. Additional inlet locations 420 are shown in phantom. Inlet locations 420 may be used to exemplify inlet locations for embodiments having one inlet, two inlets or multiple inlets. The rectangular reservoir 102 in FIG. 30A shows additional inlet locations 420a, 420b and 420c are along wall 66. Additional inlet locations 420d and 420e are shown along wall 64. Additional inlet locations 420f, 420g and 420h are shown along wall 62.

The dashed line 425 in FIGS. 30A, 30B and 30C indicates a division of the reservoir interior into adjacent 425a and forward 425b portions. The location of an inlet may be described as being adjacent or forward of the outlet. In the embodiments illustrated in FIGS. 30A, 30B and 30C, all alternative inlets 420a-420g are shown in positions forward of outlet 104. FIG. 28A illustrates a two inlet embodiment where the second inlet 420 is placed in an adjacent position relative to the outlet 104.

A reservoir 102 may have a shape other than rectangular. FIG. 30B is a top down view of an oval reservoir 102 with a wall 68. An outlet 104 is shown in wall 68 within the portion 425a. Additional inlet locations 420a-420g are shown in phantom about the perimeter of the wall 68.

A reservoir may have a polygon shape or non-geometric shape. FIG. 30C is a top down view of a polygonal, non-rectangular reservoir 102. In the illustrated embodiment, the non-rectangular polygon is an octagon. The reservoir 102 in FIG. 30C has walls 67, 68, 62, 63, 64, 65 and 66. An outlet 104 is shown in wall 68 about midway between walls 61 and 67. Additional inlet locations 420 are shown in phantom. Inlet locations 420 may be used to exemplify inlet locations for embodiments having one inlet, two inlets or multiple inlets. The octagon reservoir 102 in FIG. 30C shows additional inlet locations of: 420a in wall 67, 420b in wall 66, 420c in wall 65, 420d in wall 64, 420e in wall 63, 420f in wall 62 and 420g in wall 61.

Figure 31:
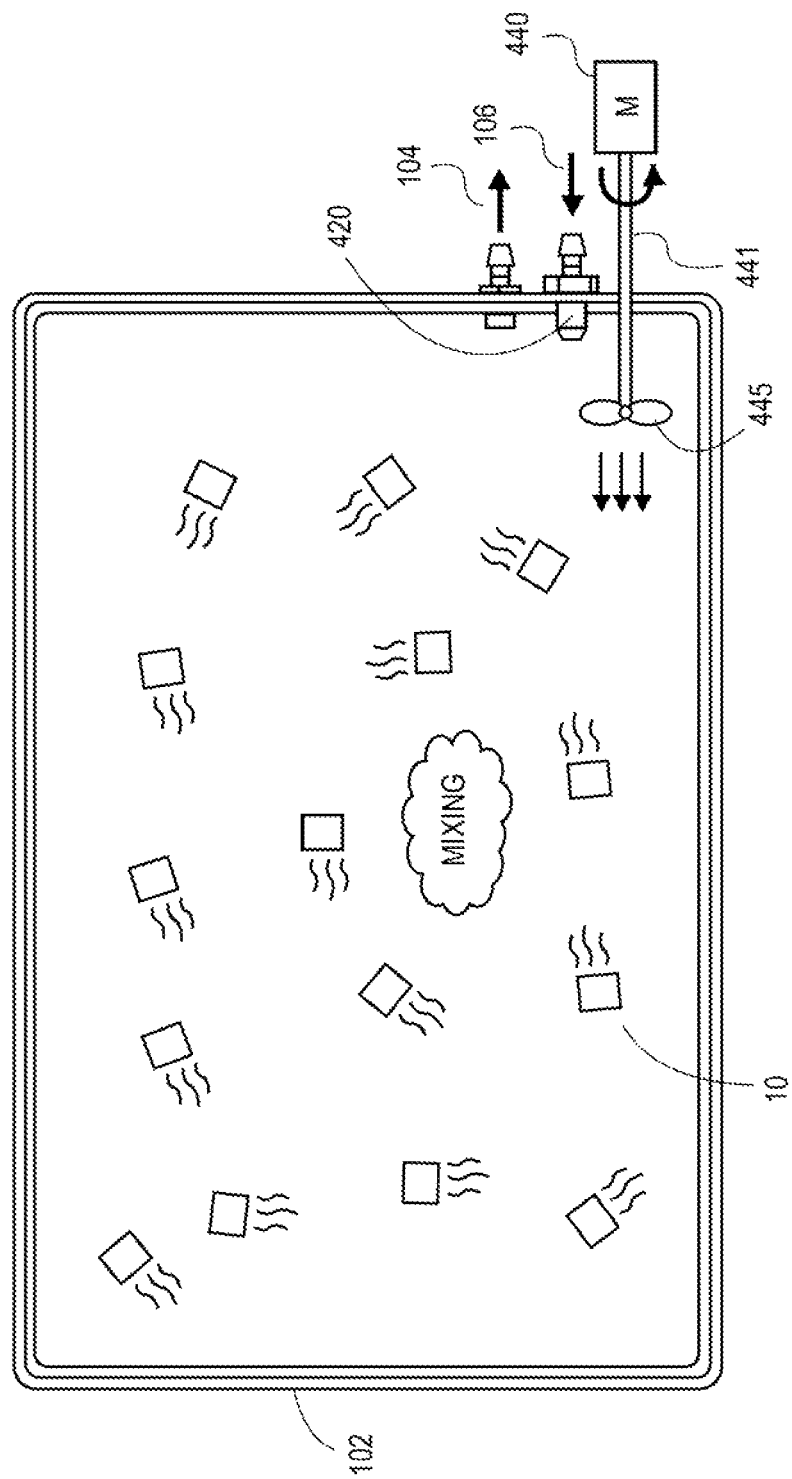
FIG. 31 is a top down view of a reservoir with an impeller.

Another mixing method comprises an agitator, impeller or other stirring implement to stir the reservoir fluid 10. As illustrated in the top down view of FIG. 31, a reservoir 102 includes an inlet 106 connected to a nozzle inlet 420 and an outlet 104. An impeller 445 is connected to movement mechanism 440 via a shaft 441. A suitable seal or bearing is provided on shaft 441 where it penetrates the reservoir wall. In operation, the impeller 445 mixes the reservoir fluid 10.

The orientation of the impeller 445 within the reservoir 102 may be fixed as shown, or variable. A coupling (not shown) may be provided enabling the impeller 445 to be flexed, rotated or pivoted in any direction within the reservoir. In addition or alternatively, the shaft 441 may be a flexible shaft that may be use to insert or withdraw the impeller 445 relative to the reservoir interior. The movement mechanism 440 and the coupling (if provided) may be operated manually or driven by any suitable electrical or mechanical device suited to mixing the reservoir fluid 10. The operation of the impeller 445, including, for example, rotation, insertion, withdrawal or variable orientation of the impeller, may be under control of the user or as system controller as described herein. The impeller 445 may be placed in a number of different locations around the reservoir wall as well as used in conjunction with different reservoir shapes. As such, the impeller may be placed as discussed above in the alternative positions and reservoir shapes of FIGS. 30A-30C or along the reservoir floor 53. Additionally, the impeller may be positioned in a wall in any of a wide variety of distances from the floor 53 depending upon the desired mixing result.

In still another alternative, a mixing method technique may include injecting air into the reservoir 102 to encourage mixing of the reservoir fluid 10. FIG. 32 is a side view of a reservoir 102 having an inlet 106 connected to an inlet tube 420 and an outlet 104 with a filter 910. An aperture 442 is provided in reservoir floor 53 adjacent an outlet 104. A source of air or air bubbler provides an air flow 450 through tubing 444 and aperture 442. Air exiting aperture 442 produces bubbles 448 injected upwards within the reservoir fluid 10. In the illustrated embodiment, the bubble action interacts with the return fluid flowing from the reservoir inlet 106 via tubing 420 and flowing out from reservoir outlet 104 to produce mixing 446 indicated by the arrows with in fluid 10. The source of air could be a dedicated air source. Alternatively, the source of air cold be a return air flow from the wrap where the wrap includes an air bladder or compressive capability. The air source could also be an air source or pump included in the system to provide air for the operation of the wrap.

Another method to alter the performance characteristics of a thermal therapy system 1 is to return fluid far away from the reservoir outlet 104 when cold temperatures are desired. In addition, in some situations, it may be advantageous for the fluid returning to the reservoir to enter in a manner the produces as little disruption to the existing thermal conditions within the reservoir 102. Techniques such a separating the inlet from the outlet describes above or use of moving inlets with or without alterations to pump or flow speed may also be utilized.

In addition to the techniques described above, a diffuser may be used in conjunction with an inlet to mitigate agitation produced by flow returns at higher flow rates. A diffuser may be used to slow the velocity of the return fluid in order to minimize turbulence and mixing in the reservoir. A number of diffuser embodiments will be described with reference to FIGS. 33A-C, 34 and 35. Each embodiment illustrates a top down view of a reservoir 102 with an outlet 104 in wall 68 and inlet in wall 66. In each embodiment, a diffuser embodiment is provided in proximity to the inlet to produce a diffused flow return 503. Each of the diffuser embodiments will now be described in turn. A diffuser may be formed from any suitable material such as mesh, plastic, metal or other material.

FIG. 33A illustrates a top down view of a reservoir 102 having a horn shaped diffuser 500. An isometric view of the diffuser 500 is provided in FIG. 33B. FIG. 33A illustrates a cross-sectional view of the outwardly shaped curvature diffuser 500 with an inlet 504 and an outlet 502. Fluid flow— initially having a faster velocity when entering at inlet 504— is slowed by the increasing diameter as the flow progresses towards outlet 502. FIG. 33A illustrates the outwardly shaped curvature diffuser 500 is connected to wall 66 and inlet 106. Return flow from outlet 502 produces a diffused flow pattern 503 within the reservoir 102.

FIG. 34B illustrates a top down view of a reservoir 102 having a block diffuser 550 positioned proximate to the inlet 522 connected to inlet 106. The block diffuser 550 is includes a number of walls 520 and with spacing or opening 522 distributed in order to deflect the incoming flow into a plurality of diffused flow patterns 503, 503b and 503c.

FIG. 35 illustrates screen diffuser 530 arranged about an inlet tube 110 connected to the reservoir inlet 106 in a reservoir 102. The screen diffuser 530 includes one or more screen layers. In the illustrative embodiment of FIG. 35, three screen layers 515a, 515b and 515c are shown. Fluid returning to the reservoir through inlet 106 passes through the screen diffuser 530 to produce a diffused flow pattern 503 within reservoir 102. In FIGS. 33A, 34 and 35, isotherms 8 may be created as a result of the diffuser produced flow 503 leading to to poor mixing of the warmed return fluid. In one aspect, a reservoir equipped with a diffuser may periodically divert flow to the diffuser inlet in order to re-establish isotherms in the reservoir. In one aspect, a method of providing thermal therapy would include diverting all or a portion of a return flow through an inlet adjacent a diffuser.

It should also be noted that the reservoir inlet diffusers could be moved to the reservoir outlet if warmer wrap temperatures are desired. The diffuser concept may also be combined with the diverter valve concepts and/or baffle concepts to achieve various performance levels.

Figure 36:
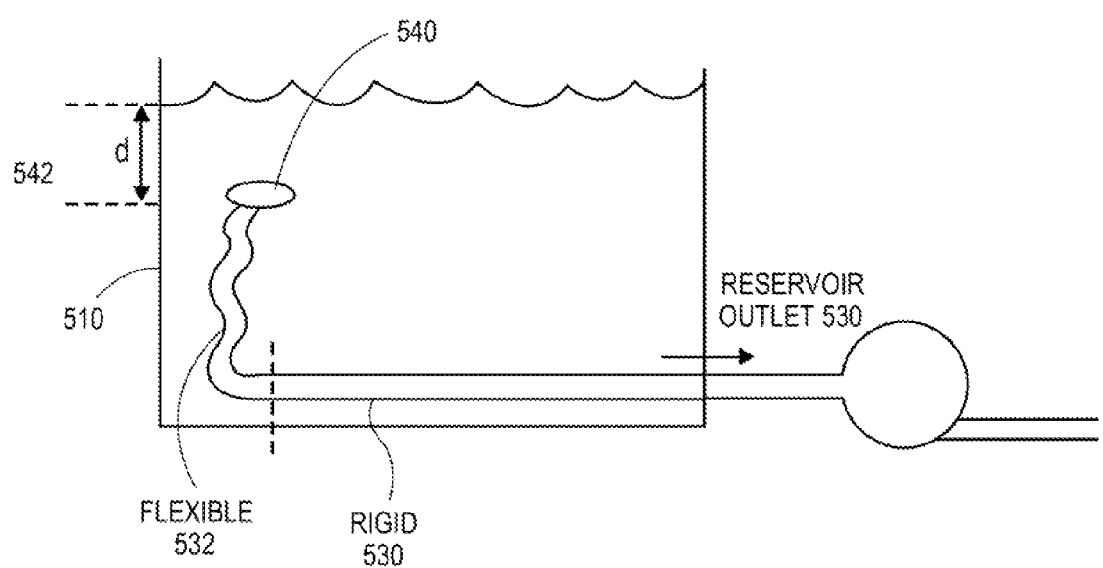
FIG. 36 illustrates a section view of a reservoir having a floating reservoir outlet tube in the reservoir.

Another method to improve the performance of the thermal therapy system 1 is a floating reservoir outlet tube to draw water from close to the top of the reservoir where the ice is and further to maximize full cold setting. FIG. 36 illustrates an embodiment of a floating reservoir outlet tube 540 in reservoir 510 floating beneath a reservoir fluid portion 542. The floating reservoir outlet tube 540 may have a rigid portion 530 and a flexible portion 532. Alternatively, the floating reservoir outlet tube 540 may be of one type of flexibility or rigidity. Additionally, this method may be combined with a diverter valve as described above.

Figure 37:
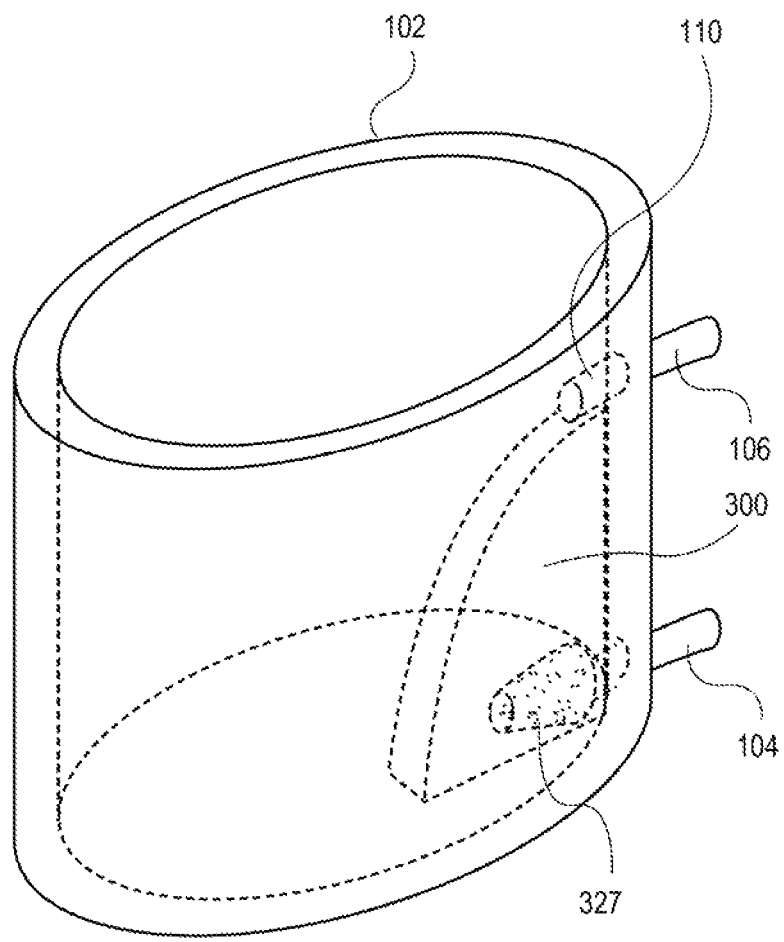
FIG. 37 is an isometric view of an oval shaped reservoir with a baffle and filter.

The thermal therapy systems described herein may be used with or without filters within the reservoir. Filters may be connected directly to or adjacent the reservoir outlet 104. This configuration is exemplified in FIG. 27C with filter 327. Alternatively, FIG. 37 illustrates isometric view of a cylindrical reservoir 102 with a filter 327 used in conjunction with a baffle.

Figure 38:
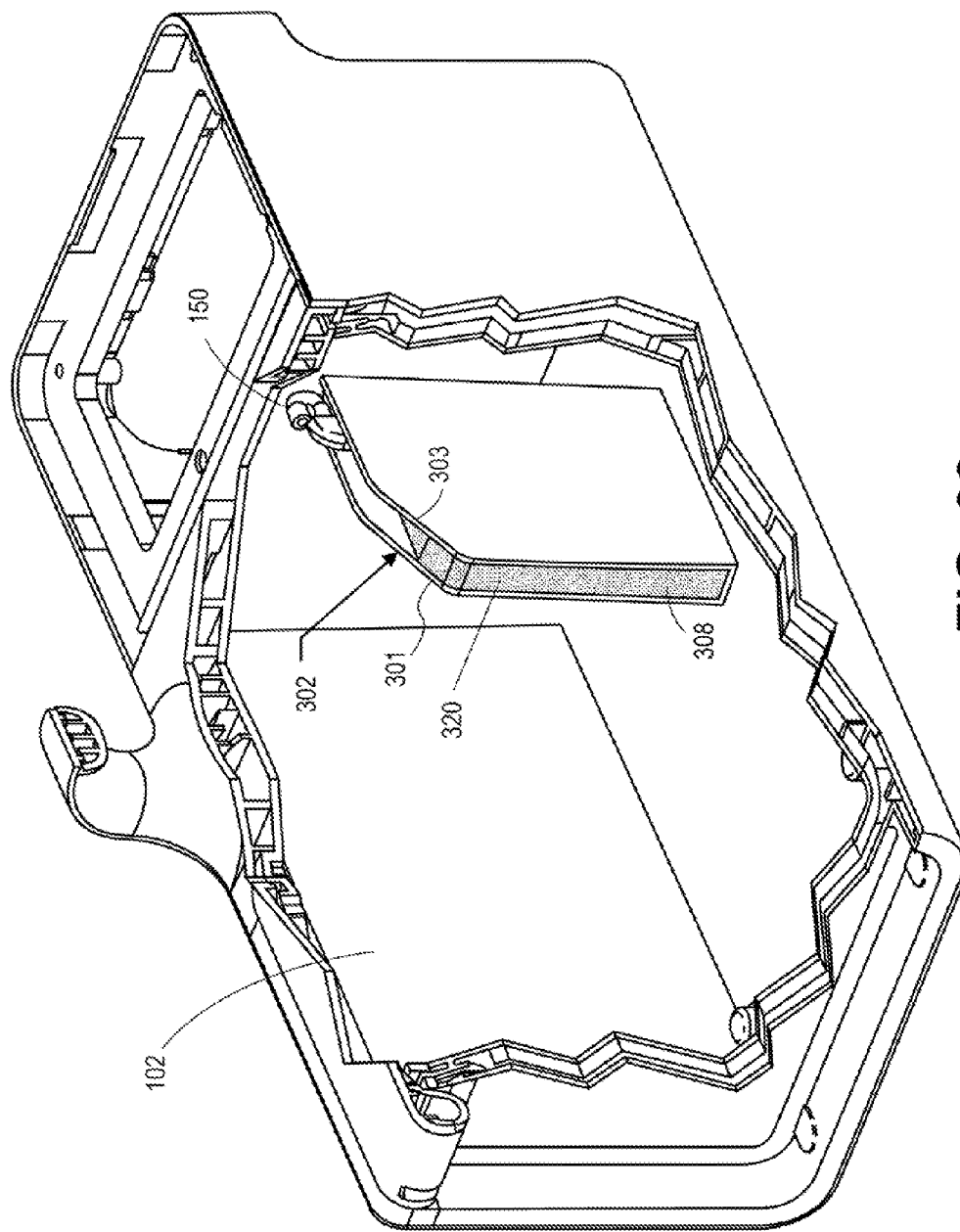
FIG. 38 is an isometric view of a baffle and filter cartridge.

A filter may also be inserted into and supported by a baffle. As illustrated in FIG. 38, a baffle 302 may support a filter cartridge 320. The filter cartridge 320 is configured to fit between the walls 301, 303. The filter cartridge 320 may include any suitable filter material such as spongy, porous, mesh or plastic materials. Instead of a cartridge 320, a filter material may be cut to fit and inserted between the walls 301, 303. In addition or alternatively, baffles may also include a screen across, partially across or extending from the walls 301, 303 to further aid in keeping ice out as well as acting as a filter.

Figure 39:
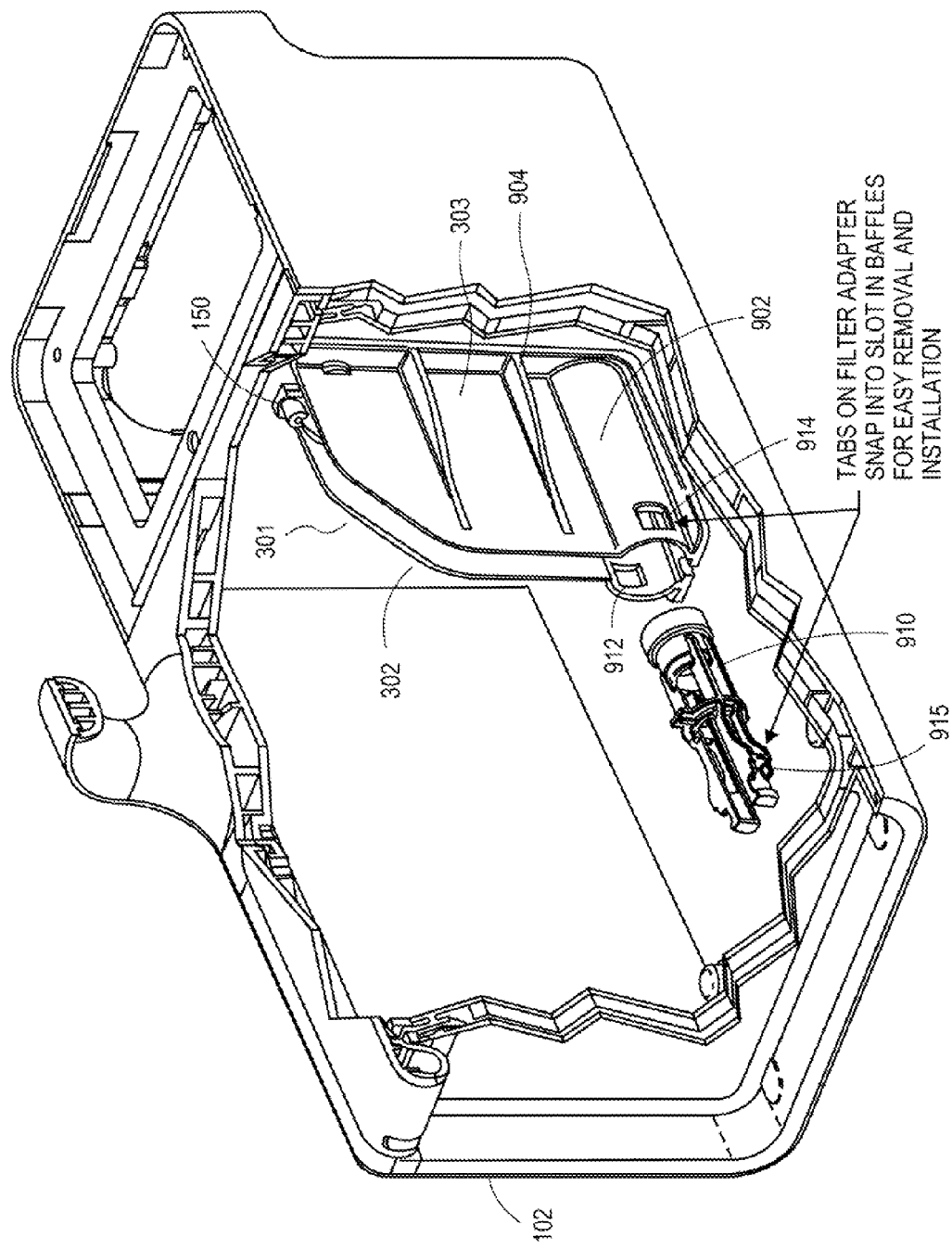
FIGS. 39, 40, and 41A-41D illustrate embodiments of a reservoir, baffle and filter assembly configured to be inserted inside a filter receptacle.
Figure 40:
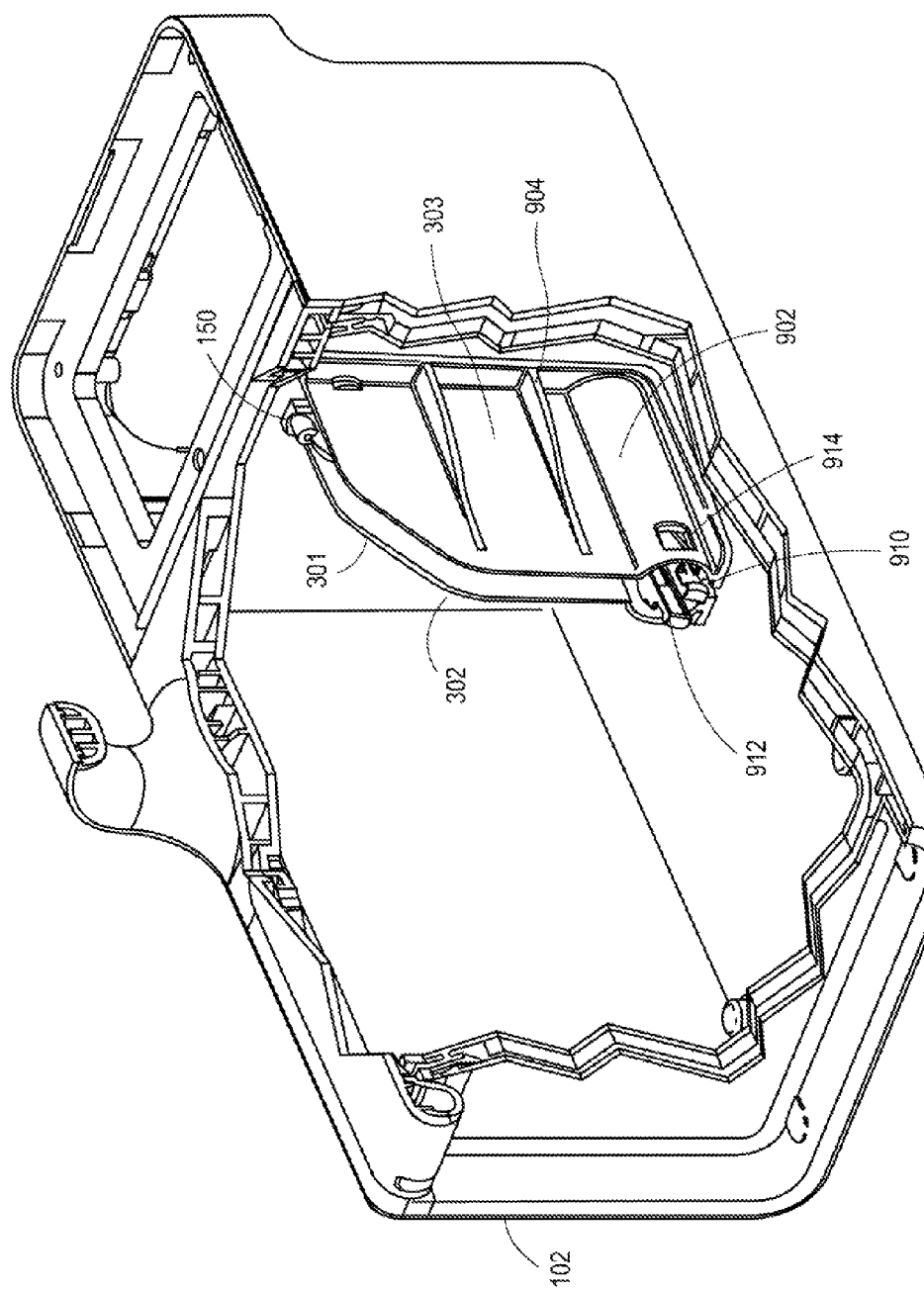

FIGS. 39, 40, and 41A-D illustrate embodiments of a reservoir, baffle and filter assembly configured to be inserted inside the filter receptacle 912 of the baffle 302. FIGS. 39 and 40 illustrate a baffle 302 with a filter receptacle 912 and tabs 915 of filter assembly 910 adapted to be inserted into the filter receptacle 912 and captured by slots 914. The filter receptacle 912 is in fluid connection with the pump system 5 via the outlet 104 as described above and as shown in FIG. 1. The filter receptacle 912 may be circular or another shape. The baffle 302 has baffle ribs 904 to keep the baffle wall rigid and/or connect them to the reservoir wall.

FIG. 39 illustrates the filter assembly 910 outside of the baffle prior to inserting filter assembly into the filter receptacle portion of the baffle. FIG. 40 illustrates the filter assembly 910 placed inside the baffle 302 with tabs 915 of the filter assembly 910 filling the slots 914, thus retaining the filter assembly 910 in place.

Figure 41A:
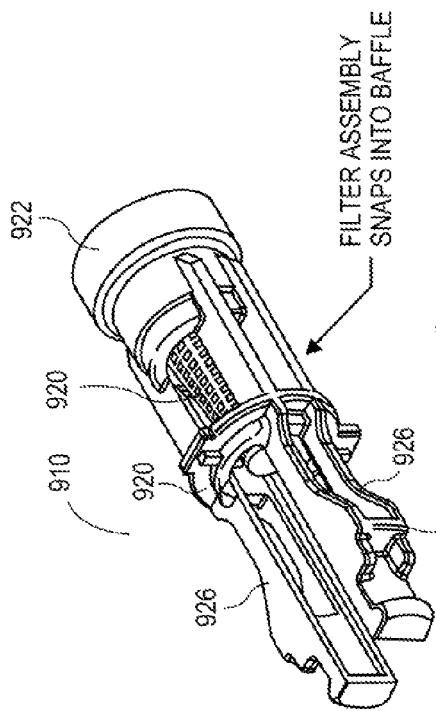
Figure 41B:
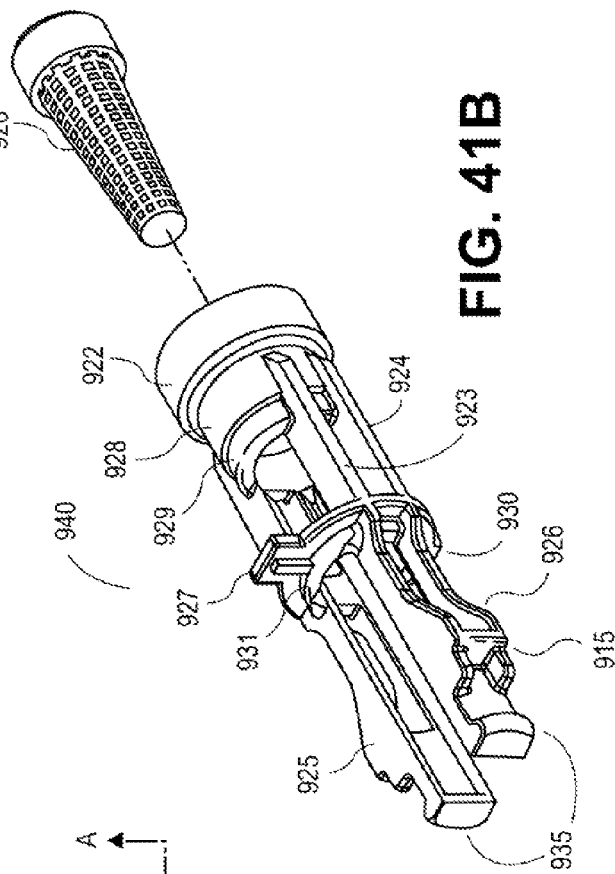
Figure 41C:
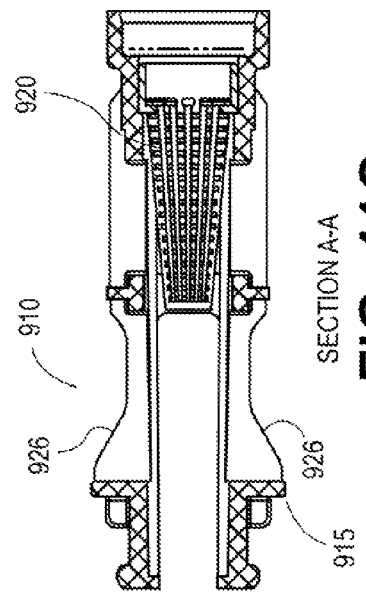
Figure 41D:
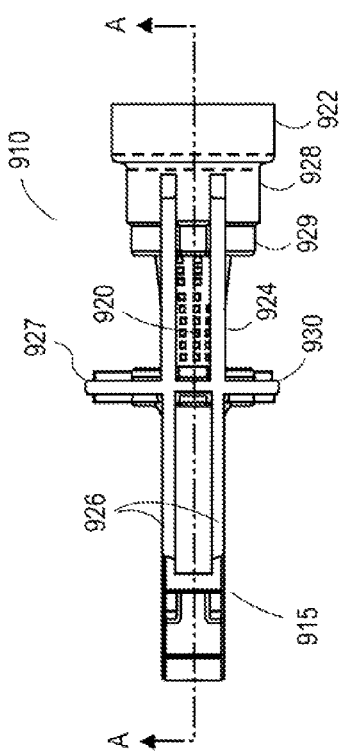

FIGS. 41A and 41B (exploded view) illustrate isometric view of the filter assembly 910. In FIG. 41A, the filter 920 is shown as inserted inside filter holder 940 along a filter center longitudinal axis. The axis is shown in FIG. 41B. FIG. 41B illustrates an exploded view of the filter assembly. FIG. 41C a section view of the filter assembly 910. FIG. 41D illustrates a side view of filter assembly 910.

The filter assembly 910 is comprised of two separated pillar extensions 925. The two back pillar extensions 925 located on both sides of the filter holder 940 comprise snap support ribs 926. The gripping area 935 may be pinched or brought together by a force, enabling the filter assembly 910 to be inserted inside the filter receptacle 912. The angles in snap support ribs 926 act as a guiding feature allowing the back pillar extensions 925 to deflect inwards when being inserted into a baffle. The back pillar extensions 925 comprise the four tabs 914. Alternatively, the filter assembly may have one tab or multiple tabs or alternatively, no tabs. Other connections, gripping mechanisms or guiding features may be used to insert the filter assembly 910 into the filter receptacle 912.

The filter holder 940 further comprises ring extension 930 for mating with the baffle walls 301, 303. The ring extension 930 unnecessary movement of the filter assembly 910 with respect to the filter receptacle 912. The ring extension 930 is a location feature to allow for proper axial alignment with the baffle 902. The ring extension 930 comprises ribs 931 for structural support. Keying feature 927 helps prevent rotation of the filter assembly and ensures proper mating of snap features 915 of filter assembly 910 with slots 914 of baffle 302. Other means to provide alignment as well as prevent rotation or unnecessary movement may be provided.

The filter holder 940 further comprises front pillar extensions 923 and 924 connected to the ring extension 930 and a third lip region 929. The front pillar extensions 923 and 924 provide structural support to the ring extension 930 and the third lip region 929. The extension 930 and a third lip region 929 may or may not touch the filter 920. The third lip region 929 surrounds the filter 920 and provides an open space for the filter to be inserted. Although not shown in the Figures, the filter may be supported by an additional support near the ring extension 930.

A second lip region 928 supports or fits over the filter. A first lip region 922 may couple with a protrusion in the reservoir wall 950 or the reservoir outlet 952 so as to effectively filter fluid prior to leaving reservoir. Alternatively, the filter holder 940 may comprise one connected lip region for support of the filter. The filter assembly 910 may also be comprised of ribs and additional components to enable correct placement and support of the filter 920.

Figure 42:
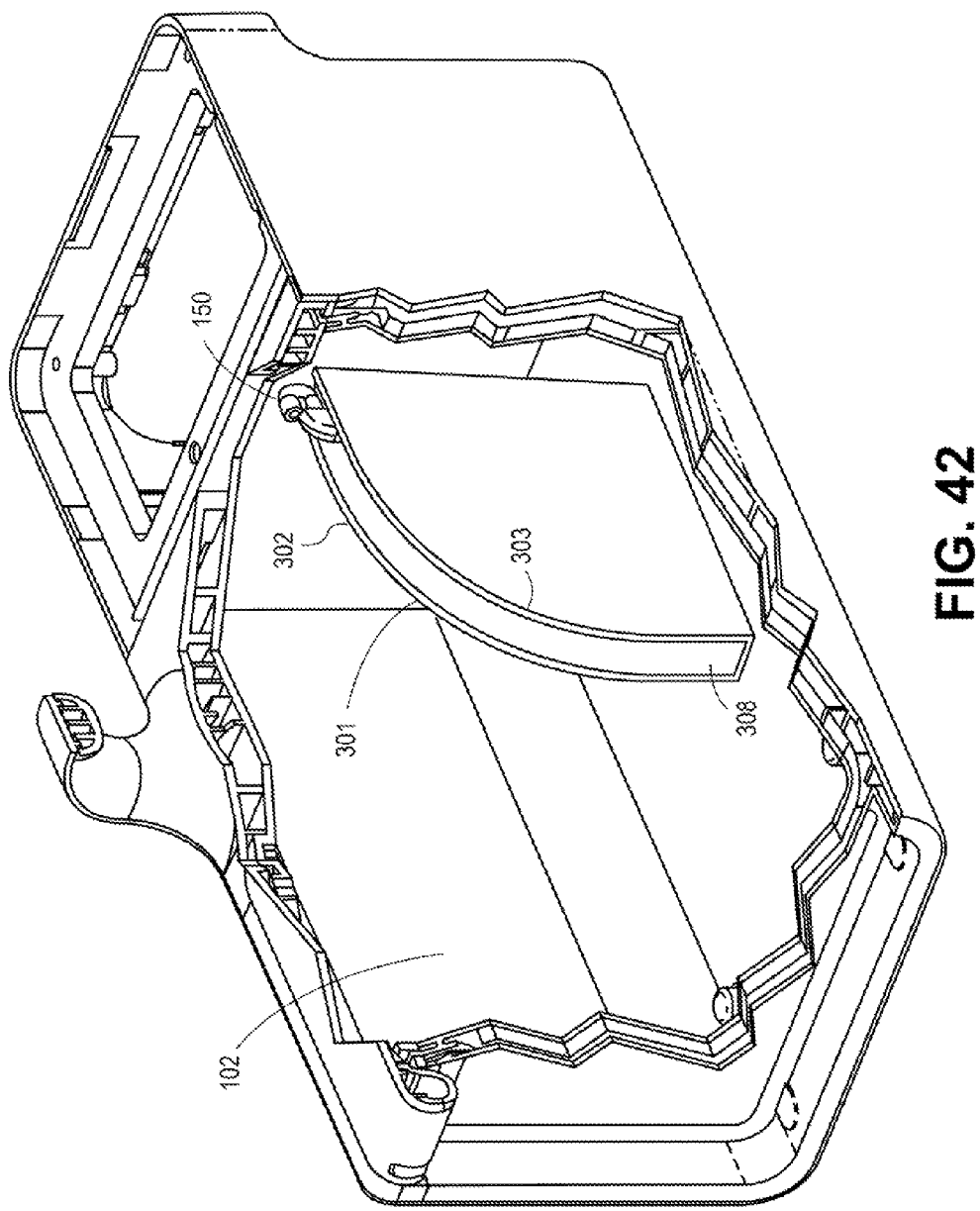
FIGS. 42, 43A and 43B illustrate a baffle in a reservoir (FIG. 42), and isometric and end views of the baffle of FIG. 42.
Figure 43B:
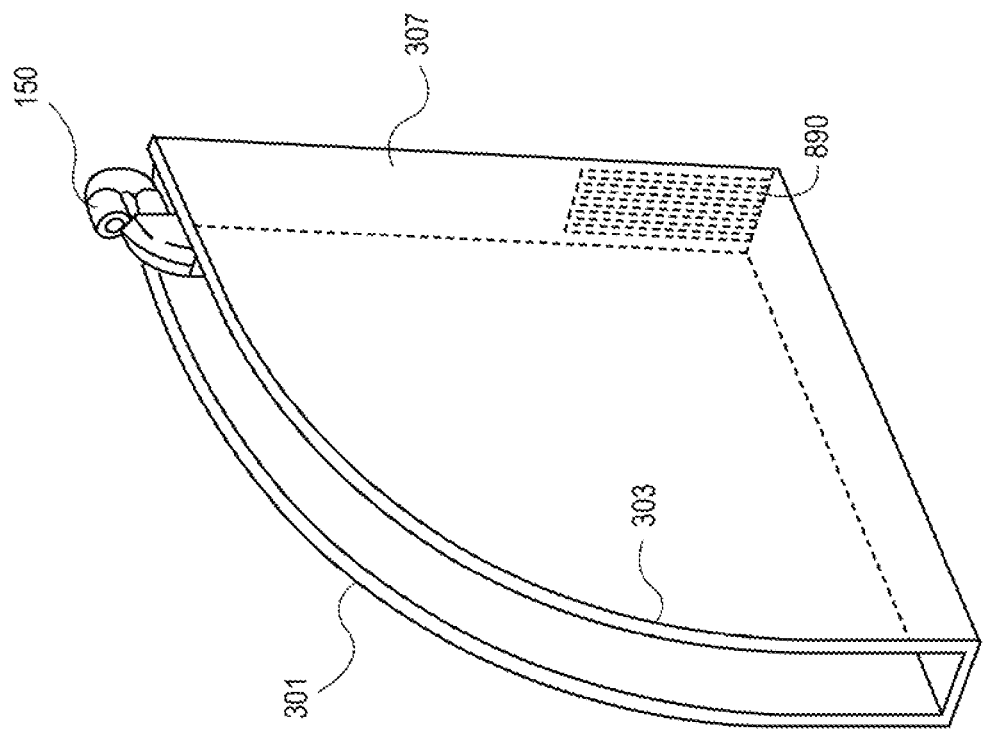
Figure 43A:
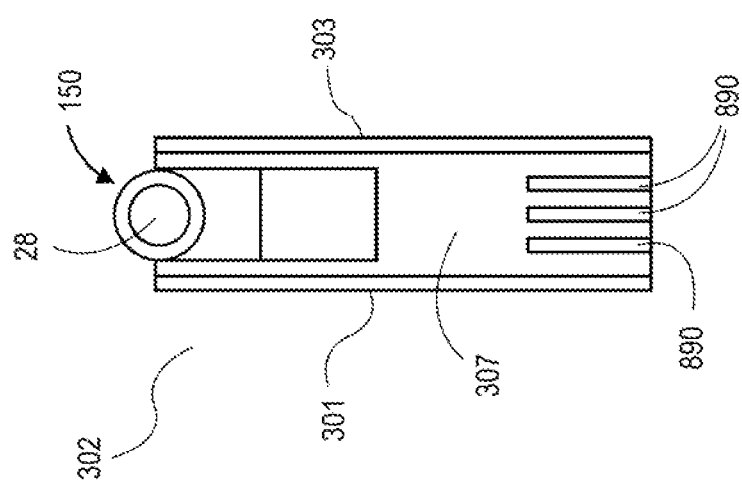
Figure 43C:
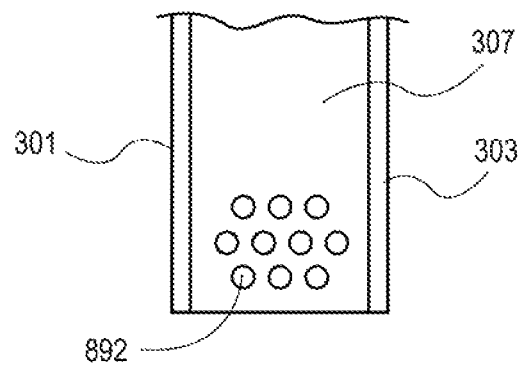
FIGS. 43C and 43D illustrate alternative openings in the baffle.
Figure 43D:
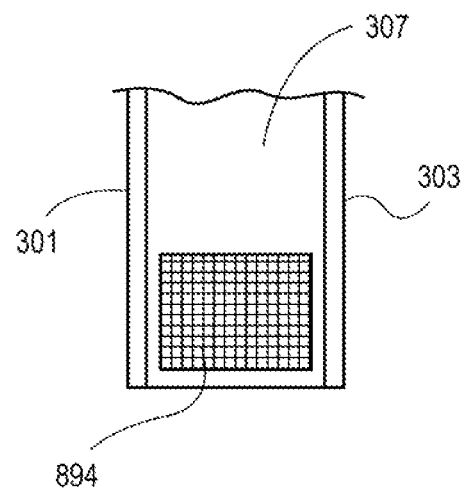

Alternatively, a baffle may be altered to provide filtering capabilities by providing apertures in one or more baffle walls adjacent the outlet 104. FIG. 42 illustrates a baffle 302 positioned within a reservoir 102. The walls 301, 303 are straight meaning that there is not a flared bottom 308 as in earlier embodiments such as the baffle of FIGS. 39 and 40. FIGS. 43A and 43B are end and isometric views of a baffle 302 with a back wall 307 modified in proximity to the inlet 104 when the baffle 302 is positioned for use in a reservoir 102. In the illustrative embodiment shown in FIGS. 43A and 43B the back wall 307 has been modified to provide vertically extending slots 890. The baffle back wall 307 may be modified in any number of ways to provide a filtering capability. As shown in FIG. 43C, the baffle back wall 307 may be modified to include a plurality of apertures 892. As shown in FIG. 43D, the baffle back wall 307 may be modified to form rectangular openings or to permit a screen 894 to be inserted across a suitable opening adjacent the inlet 104.

Another method to improve the performance of the thermal therapy system 1 is a set point control system. The flow rate may be controlled through the control system 7 by using a closed feedback loop based on temperature of the wrap 3 or fluid leaving and/or returning to the control unit. A user may set a desired temperature, and the flow rate may be adjusted until a temperature sensor reads that value, and then continuously updated to keep the desired set point. The desired temperature may also be stored in a central processor or elsewhere. The baffle embodiments and inlet embodiments described herein may be used in conjunction with a wide variety of thermal systems to improve or alter the performance of those systems.

Yet another method to improve the performance of the thermal therapy system 1 provides a return stream vector control with a diverter valve. The diverter valve may comprise a valve or other switching means to direct some return fluid proximal to the reservoir outlet, and the balance of the return stream distal to the reservoir outlet, or any ratio. The fluid flow rate may not need to be reduced. The diverter valve is configured to provide adjustments outside the reservoir by simplifying design or by bringing controls to a more convenient location to the user. Moreover, the diverter valve is used to help create temperature gradient/isotherms in the reservoir, when desired.

Figure 44A:
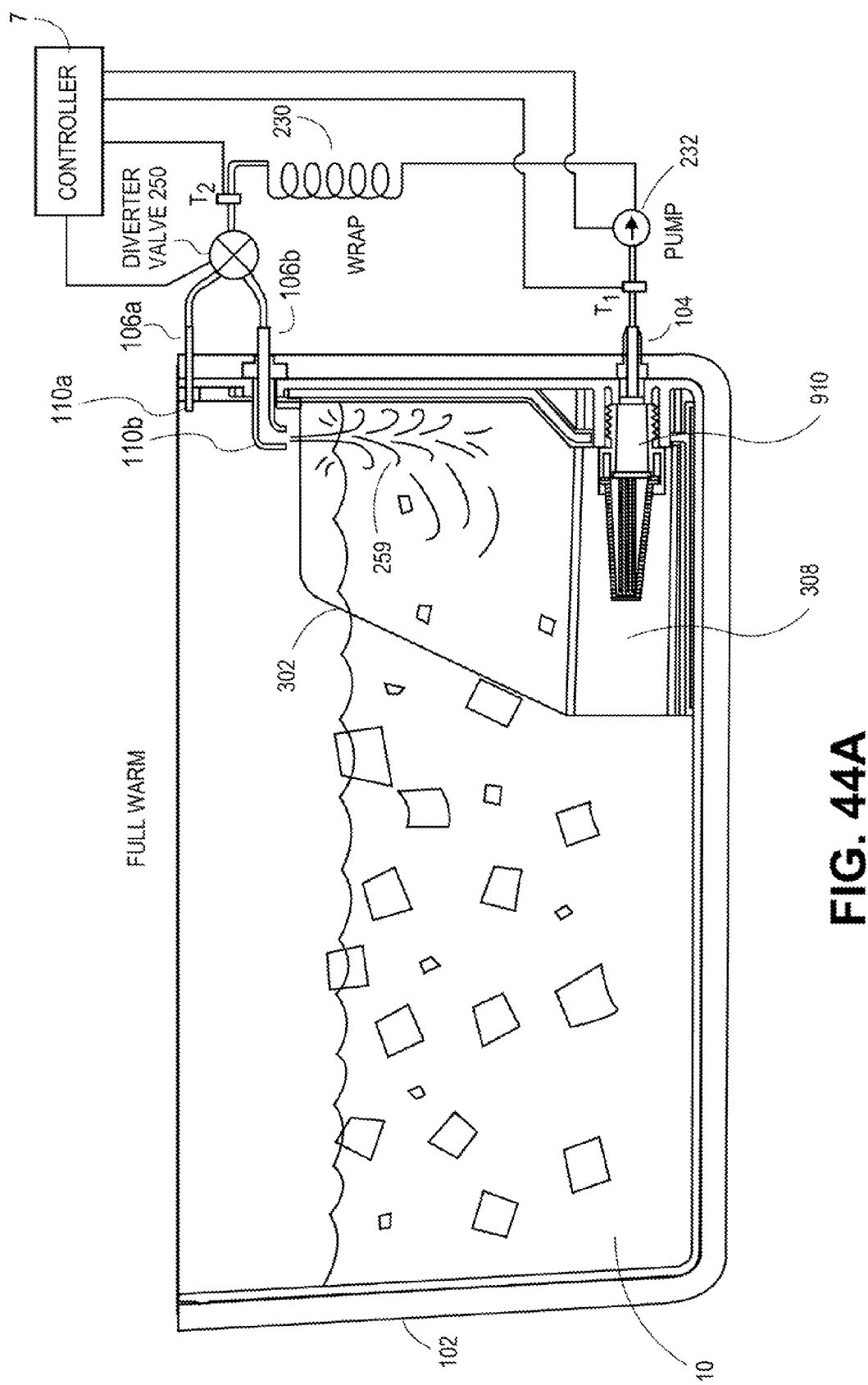
FIGS. 44A, 44B and 44C illustrate the operation of a therapy system having a baffle, two inlets and a diverter valve in different stages of operation and flow conditions.
Figure 44B:
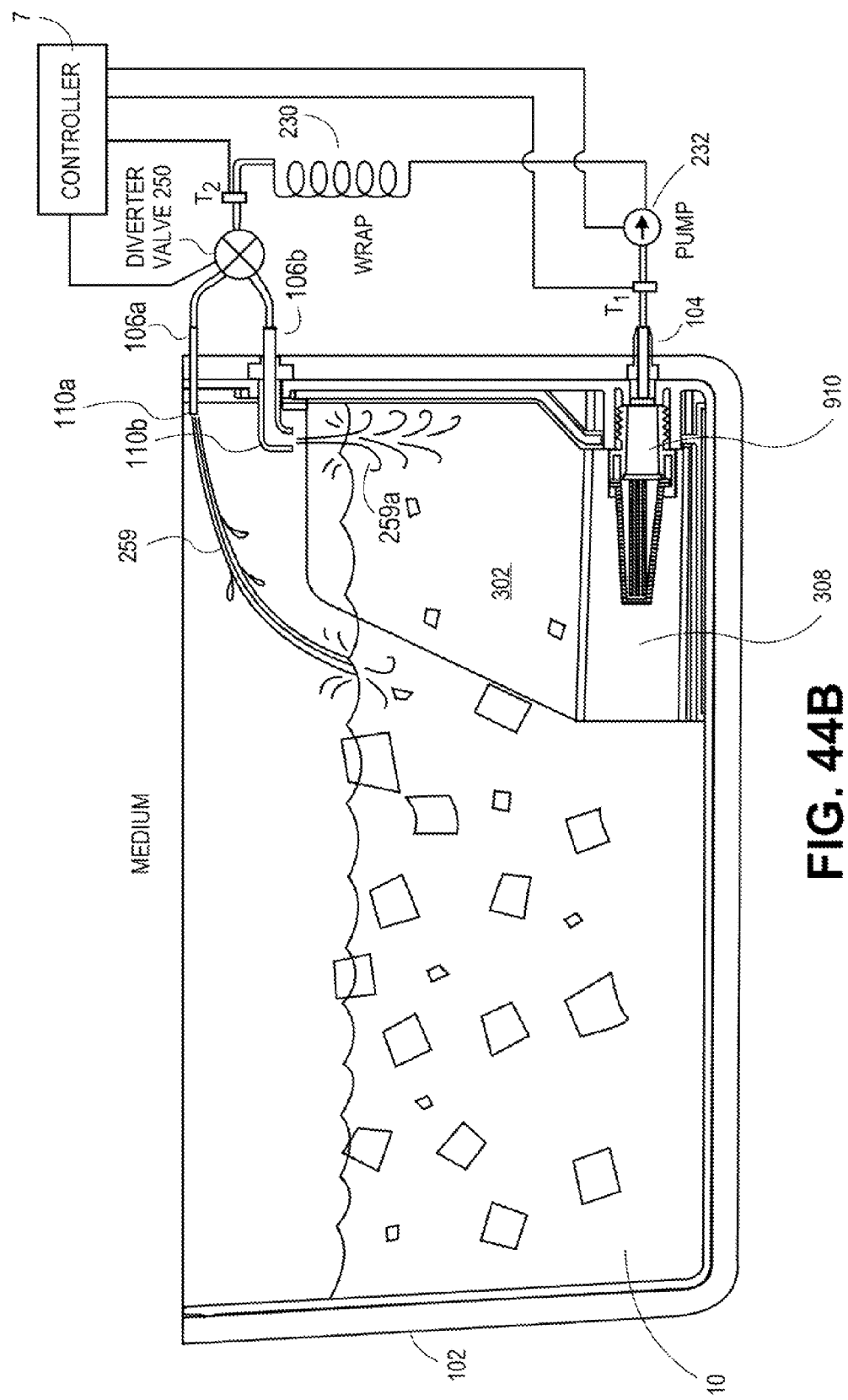
Figure 44C:
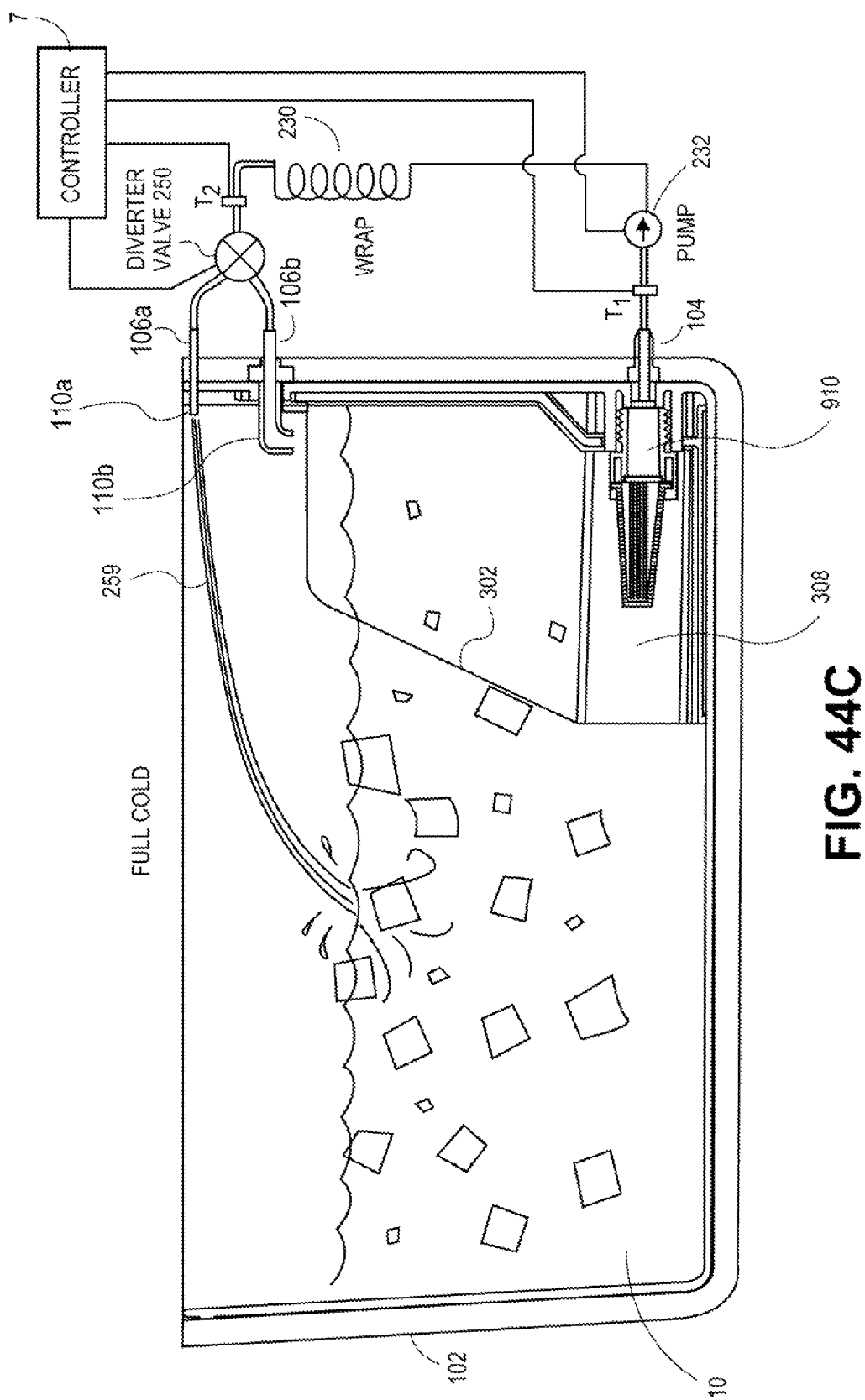

FIGS. 44A-44C illustrate embodiments of the return stream vector control with a diverter valve 250. The illustrated thermal system includes a reservoir 102 having an outlet 104 within a baffle 302 and an upper inlet 106a and lower inlet 106b. The upper inlet 106a is connected to an inlet tube 110a and the lower inlet 106b is connected to a downwardly directed inlet 110b. A diverter valve 250 is in under the control of controller 7 and in fluid communication to direct flow from the wrap 230 to the inlets 106a, 106b. The system also includes a pump 232 and sensors T1, T2 to monitor the fluid temperature in the system. Sensor T1 is positioned at the outlet 104 and sensor T2 is positioned at the outlet of wrap 230. The pump 232 and sensors T1 and T2 are in communication with the controller 7. The pump 232 operating under instructions from the controller 7 or, alternatively, from user input.

Under control of the system controller 7 or, alternatively, a user, the diverter valve 250 allows and/or prevents flow through the inlets 110a, 110b. As a result of the relative orientations of the inlets (i.e., 110a towards the reservoir interior and 110b towards the outlet 104), the diverter valve 250 also directs return of warmer water from the wrap 230 closer or farther away from reservoir outlet 104. Fluid flow may be diverted entirely through inlet 106b and 110b as shown in FIG. 44A. In this operational state, the return flow 259 is directed only towards inlet 104. Alternatively, fluid flow may be diverted through both inlets 110a, 110b producing dual flows 259a towards the outlet 104 and 259b towards the reservoir as shown in FIG. 44B. For colder temperature fluid supplied to wrap 302, the diverter 250 may direct flow entirely to the upper inlet 106a and flow tube 110b to produce the flow 259 shown in FIG. 44C.

While illustrated with fixed inlet tubes 110a, 110b, other inlet configurations such as with surface directed tongues, movable inlets or nozzle inlets, among others may be used with the diverter valve system of FIGS. 44A-44C.

Alternatively, the diverter valve may be used to selectively draw fluid from one or more reservoir outlet locations to draw either warm fluid or cold fluid or any combination thereof. In addition, a thermal control system may include multiple diverter valves either coupled together for synchronous operation or independent operation.

Figure 45:
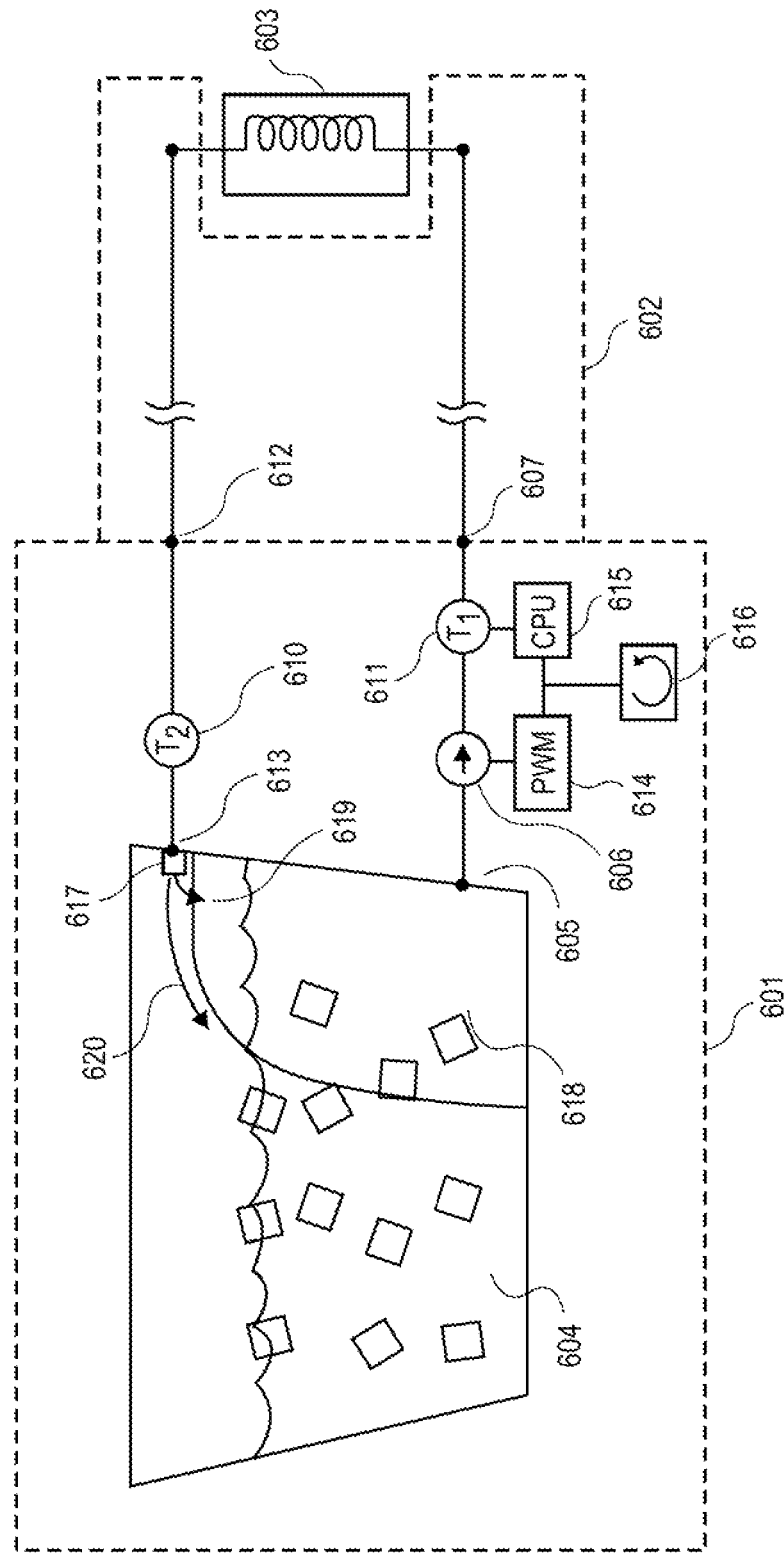
FIG. 45 illustrates an embodiment of a temperature control system with a set point control system.

In another alternative thermal system embodiment, the inlet and baffle improvements may be utilized in the thermal system illustrated schematically in FIG. 45. The various inlet improvements described herein are represented schematically by the inlet 617. The various baffle improvements described herein are represented schematically by the baffle 618. As the system varies the speed of pump 606, the flow entering the reservoir 604 will be directed within the baffle 618 towards inlet 605(flow path 619) or towards the interior and clear of the baffles 618 (flow path 620). Based on operation of pump 606, the inlet 617 directs the return fluid 620 far away from the reservoir outlet 605 in an exemplary cold setting. In warmer setting, the operation of pump 606 provides a return fluid path 619 is directed closer to the reservoir outlet 605.

The set point control system provides for an automatic control of the temperature of reservoir 2 (see FIG. 1). The embodiment of FIG. 45 illustrates a thermal treatment system with a temperature control system having set point control. In this embodiment, the treatment system 601 comprises a pump 606, a first temperature sensor 611, a CPU/controller 615, a second temperature sensor 610, and a control 616 for adjusting, inputting or indicating the desired temperature of wrap 603. Temperature sensor 611 may read the temperature of the fluid on the path towards the wrap 603 prior to leaving the control unit at point 607. Temperature sensor 610 may read the temperature at return flow after returning to the control unit at point 612. The flow rate through the system can be adjusted in order to achieve a desired reservoir outlet temperature read at first temperature sensor 611. In addition or alternatively, the system parameters can be adjusted in order to achieve a desired wrap temperature employing a pulse width modulation control scheme (PWM) 614 in conjunction with controller 615.

The average wrap temperature may be estimated by averaging temperatures as read by the first temperature sensor 611 and the second temperature sensor 612. Other techniques may be used to estimate wrap temperatures. The temperature may be displayed to the user. The PWM may alternatively be replaced by another method of controlling fluid pump motor speed.

Alternatively, the set point control system may include more than two temperature sensors or only one sensor. Other temperature sensing methods may be used in the set point control system.

In the alternative, one or more temperature sensor(s) may be added to the thermal therapy device 1 in combination with an improved reservoir (i.e., baffle, nozzle, etc), improved control system or improved wrap as shown above. The temperature sensor(s) may be provided 1) on an inside surface or on an outside surface of the fluid lines, 2) in the control system 7, 3) in the return system 9 and/or 4) in the wrap 3.

Moreover, methods of flow control illustrated above may utilize a pinch valve (instead of or in addition to a PWM), a rheostat, or a dimmer switch or a buck regulator. Methods of flow control illustrated above may utilize a resistor matrix or other mechanism coupled to the pump motor for control of pump settings.

Below are alternative methods of temperature control. These methods also change the temperature in the wrap 3 by changing the flow rate of the fluid through the wrap 3. In all possible valve positions described, the fluid from the wrap 3 is returned to the reservoir.

Figure 46:
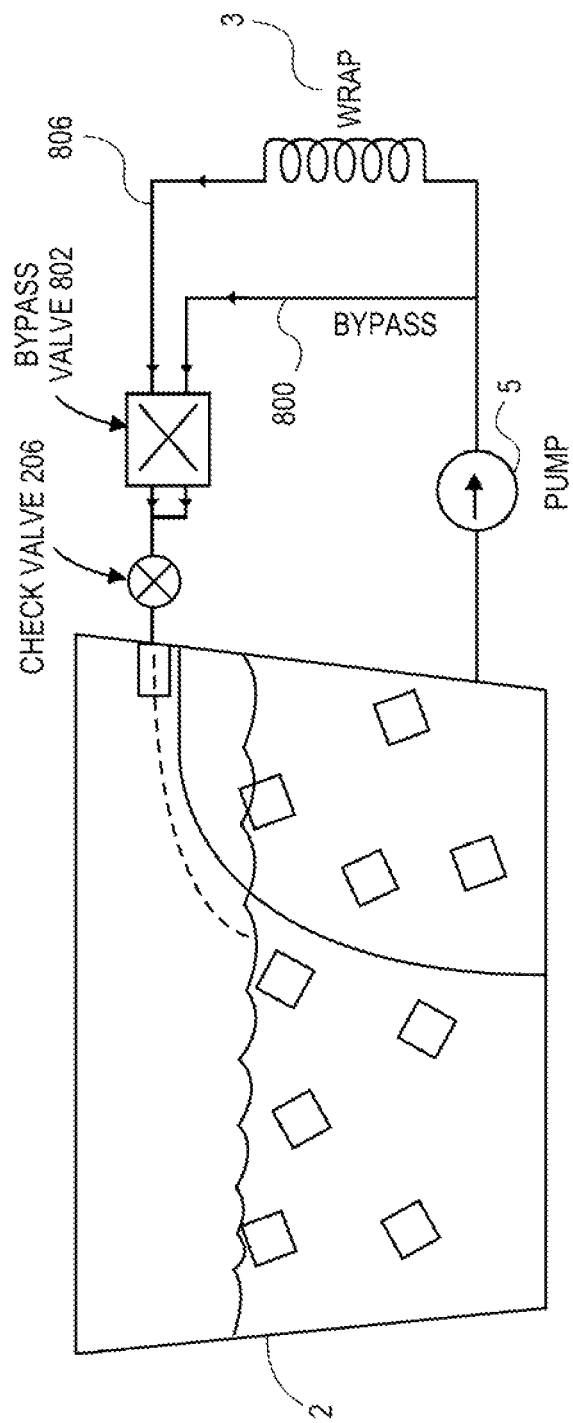
FIG. 46 illustrates a pump and two fluid paths configured to optimize flow though a wrap controlled with a bypass valve.

FIG. 46 illustrates a pump and two fluid paths 800 and 806. The first fluid path 806 is through the wrap 3, and the second fluid path 800 is a bypass path that allows fluid to bypass the wrap. The amount of bypass can be controlled by a "Bypass Valve" that can be positioned to allow 0% bypass, 100% bypass, or anywhere in between. A condition of 0% bypass would force all the fluid to be pumped through the wrap, giving maximum cold. A condition of 100% bypass would force all fluid to be pumped past the wrap (no flow through the wrap) which would provide little active cooling. A condition of 50% bypass would allow half the fluid to be pumped through the wrap 3, and half the fluid to be pumped past the wrap which would provide a "medium" level of cooling, etc. The use of a check valve (or orifice, or needle valve) between the Bypass Valve and the reservoir allows for backpressure to be applied to the wrap which is beneficial in that the back pressure tends to "inflate" the fluid chamber in the wrap and thus helps to prevent kinks that may develop—particularly during the compression cycle of the wraps. The bypass valve may be of many different designs, such as a 3-way ball valve and two discrete 2-way valves controlled simultaneously.

Figure 47:
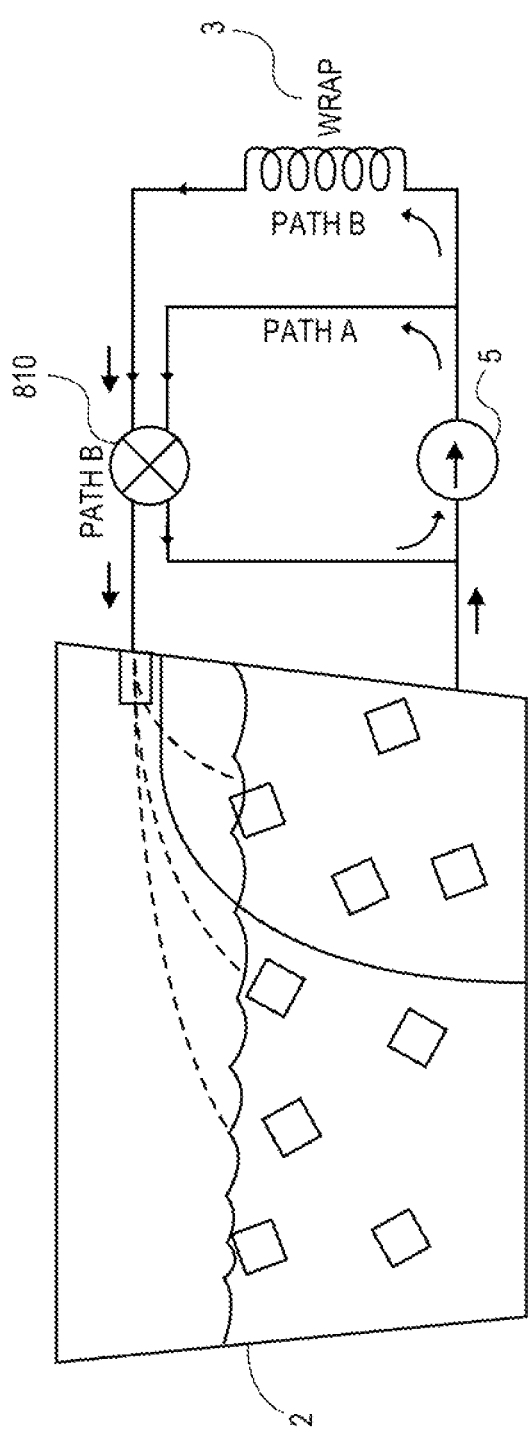
FIG. 47 illustrates fluid paths with a valve configured to optimize flow.

The embodiment of FIG. 47 illustrates fluid paths with a valve 810 to optimize flow. The fluid in Path A may be warmed by friction, or by gaining heat from the pump. Moreover, a heat source (such as the pump motor) may be placed in close proximity as to provide heat exchange and thus warm the fluid in Path A.

Each of the control systems described herein may be modified to include appropriate electronics, processing capabilities, instructions and the like to operate any of the reservoir or system improvements described herein. For example, a system controller configured to operate with a movable inlet would include, if needed, appropriate additional hardware, software or firmware to facilitate control of the actuator or control element used with the movable inlet. If the movable inlet is configured to operate with a motor as in FIGS. 25 and 26, then the controller includes capabilities suited to the control of the motor M. If the movable inlet is configured for use with a shape memory alloy element as described above with regard to FIGS. 18-20C, then the system controller includes appropriate instructions in software, firmware or hardware to facilitate operate of the shape memory alloy element to accomplish the desired functionality as a movable inlet.

While preferred embodiments of the present invention have been shown and described herein, these embodiments are provided by way of example only. Numerous variations, changes, and substitutions will now occur to those skilled in the art without departing from the invention. For example, the inlet opening 28 is illustrated as circular. The inlet opening may have other shapes, for example, oval, elliptical or rectangular. In addition, the inlet size, shape, and/or opening geometry may be altered to produce a return flow in a specific pattern. A wide variety of spray patterns may be produced with the inlet embodiments described herein. Inlets of the present invention may be modified to produce a jet spray pattern, a flat spray pattern, a conical spray pattern or other spray pattern. Moreover, the inlet configured to produce a spray pattern may also be configured as a movable inlet, further described above. In one aspect, the inlet 110*b* (FIG. 44A) may be used as a movable inlet as shown in FIGS. 22A-22C in any of the orientations of FIGS. 23 and 24 or in an orientation that permits controlled lateral movement relative to the baffles or sweeping movement of the inlet 110*b*. In addition, the inlet 110*b* may be configured to provide a spray pattern. In one embodiment, the inlet 110*b* is configured to provide a fan spray pattern.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A temperature controlled therapy system, the system comprising:
   a reservoir comprising a container with an interior defined by a floor and at least one wall, an outlet and an inlet, the inlet having an opening directed towards an interior of the reservoir;
   a therapy wrap having an inlet and an outlet, the outlet of the therapy wrap in communication with the inlet of the reservoir;
   a pump having an inlet in communication with the reservoir outlet and an outlet in communication with the therapy wrap inlet, the pump configured to circulate fluid between the reservoir and the therapy wrap;
   a flow control surface adjacent the opening configured to direct fluid flow from the opening; and
   a control system configured to control the velocity of the fluid to direct flow of the fluid to a plurality of locations from an area proximate the outlet of the reservoir to an area further away from the outlet of the reservoir, wherein at low velocities the fluid is directed to an area proximate the outlet of the reservoir and at high velocities the fluid is directed to an area further away from the outlet of the reservoir.

2. The temperature controlled therapy system of claim 1, wherein fluid moving from a proximal end to a distal end of the flow control surface at a low velocity is directed towards a predetermined location in the reservoir.

3. The temperature controlled therapy system of claim 1, wherein the predetermined location is proximate the outlet of the reservoir.

4. The temperature controlled therapy system of claim 1, wherein the flow control surface curves towards the container floor.

5. The temperature controlled therapy system of claim 1, wherein the flow control surface has a v-shaped profile.

6. The temperature controlled therapy system of claim 1, wherein the flow control surface comprises a ridge that extends from proximate the inlet of the reservoir towards the interior.

7. The temperature controlled therapy system of claim 6, wherein the ridge remains generally along the central portion of the flow control surface.

8. The temperature controlled therapy system of claim 1, wherein the flow control surface has an overall curvature from a proximal end adjacent the inlet of the reservoir to a distal end wherein the overall curvature controls the trajectory of a fluid flowing from the inlet of the reservoir to remain on the flow control surface.

9. The temperature controlled therapy system of claim 1, further comprising a nozzle on the inlet of the reservoir.

10. The temperature controlled therapy system of claim 1, wherein the inlet of the reservoir is spaced at a distance from the floor so that in use the inlet of the reservoir is above the level of a heat transfer fluid used in the reservoir.

11. The temperature controlled therapy system of claim 1, wherein the reservoir further comprises a baffle created by a first wall and a second wall within the interior such that the outlet of the reservoir is between the first wall and the second wall and the spacing between the first and second walls is less than the width of the interior adjacent the inlet of the reservoir.

12. The temperature controlled therapy system of claim 11 wherein the first wall and the second wall are joined to form a baffle assembly.

13. The temperature controlled therapy system of claim 12, wherein the baffle assembly is formed as part of the container.

14. The temperature controlled therapy system of claim 12 wherein the baffle assembly is an insert attached to the interior.

15. The temperature controlled therapy system of claim 11, wherein the spacing between the first and second walls is less than the width of a wall penetrated by both the inlet of the reservoir and the outlet of the reservoir.

16. The temperature controlled therapy system of claim 11, further comprising a filter over the outlet of the reservoir.

17. The temperature controlled therapy system of claim 11, further comprising a filter cartridge having a housing shaped to fit between the first wall and the second wall to align a filter within the cartridge over the outlet of the reservoir.

18. The temperature controlled therapy system of claim 1, wherein the flow control surface comprises a ridge beginning in a central portion of the flow control surface proximate the inlet of the reservoir and then extends towards the first wall or the second wall in a proximal portion of the flow control surface.

19. The temperature controlled therapy system of claim 1, wherein the outlet of the reservoir is in fluid communication with the interior through a penetration in the at least one wall at a location closer to the floor than the inlet of the reservoir.

20. The temperature controlled therapy system of claim 1, wherein at low velocities the fluid exits the outlet of the reservoir at a higher temperature and at high velocities the fluid exits the outlet of the reservoir at a lower temperature.

21. The temperature controlled therapy system of claim 1, wherein the control system is configured to control the velocity of the fluid such that at low velocities, the fluid is directed to flow over the flow control surface to an area proximate the outlet of the reservoir.

22. The temperature controlled therapy system of claim 1, wherein the control system is configured to control the velocity of the fluid such that at intermediate velocities, the fluid is directed to split into a first flow stream that flows over the flow control surface and a second flow stream that flows separately from the flow control surface.

23. The temperature controlled therapy system of claim 1, wherein the control system is configured to control the velocity of the fluid such that at high velocities, the fluid is directed to flow separately from the flow control surface.

24. The temperature controlled therapy system of claim 1, further comprising a temperature control system comprising a first temperature sensor configured to read the temperature of fluid exiting the reservoir, and a control configured to receive an input indicating the desired temperature and the temperature measured by the first temperature sensor, wherein the control is configured to adjust the velocity or flow rate of fluid based on the desired temperature and the temperature measured by the first temperature sensor.

25. The temperature controlled therapy system of claim 24, wherein a reduction in the velocity or flow rate of the fluid causes an increase in the temperature measured by the first temperature sensor, and an increase in the velocity or flow rate of the fluid causes a decrease in the temperature measured by the first temperature sensor.

26. A temperature controlled therapy system, the system comprising:
   a reservoir comprising a container with an interior defined by a floor and at least one wall, an outlet, an inlet, the inlet having an opening directed towards an interior of the reservoir, and a baffle created by a first wall and a second wall within the interior such that the outlet of the reservoir is between the first wall and the second wall and the spacing between the first and second walls is less than the width of the interior adjacent the inlet of the reservoir;
   a therapy wrap having an inlet and an outlet, the outlet of the therapy wrap in communication with the inlet of the reservoir;
   a pump having an inlet in communication with the reservoir outlet and an outlet in communication with the therapy wrap inlet, the pump configured to circulate fluid between the reservoir and the therapy wrap; and
   a control system configured to control the velocity of the fluid to direct flow of the fluid to a plurality of locations from an area proximate the outlet of the reservoir to an area further away from the outlet of the reservoir, wherein at low velocities the fluid is directed to an area proximate the outlet of the reservoir and at high velocities the fluid is directed to an area further away from the outlet of the reservoir.

27. The temperature controlled therapy system of claim 26, wherein the reservoir comprises a flow control surface adjacent the opening configured to direct fluid flow from the opening.

28. The temperature controlled therapy system of claim 27, wherein fluid moving from a proximal end to a distal end of the flow control surface at a low velocity is directed towards a predetermined location in the reservoir.

29. The temperature controlled therapy system of claim 28, wherein the predetermined location is proximate the outlet of the reservoir.

30. The temperature controlled therapy system of claim 26, wherein at low velocities the fluid exits the outlet of the reservoir at a higher temperature and at high velocities the fluid exits the outlet of the reservoir at a lower temperature.

31. A temperature controlled therapy system, the system comprising:
   a reservoir comprising a container with an interior defined by a floor and at least one wall, an outlet, an inlet, the inlet having an opening directed towards an interior of the reservoir, a baffle created by a first wall and a second wall within the interior such that the outlet of the reservoir is between the first wall and the second wall and the spacing between the first and second walls is less than the width of the interior adjacent the inlet of the reservoir, and a flow control surface adjacent the opening configured to direct fluid flow from the opening;
   a therapy wrap having an inlet and an outlet, the outlet of the therapy wrap in communication with the inlet of the reservoir;
   a pump having an inlet in communication with the reservoir outlet and an outlet in communication with the therapy wrap inlet, the pump configured to circulate fluid between the reservoir and the therapy wrap; and
   a control system configured to control the velocity of the fluid to direct flow of the fluid to a plurality of locations from an area proximate the outlet of the reservoir to an area further away from the outlet of the reservoir, wherein at low velocities the fluid is directed to an area proximate the outlet of the reservoir and at high velocities the fluid is directed to an area further away from the outlet of the reservoir.

32. The temperature controlled therapy system of claim 31, wherein at low velocities the fluid exits the outlet of the reservoir at a higher temperature and at high velocities the fluid exits the outlet of the reservoir at a lower temperature.

33. The temperature controlled therapy system of claim 31, wherein fluid moving from a proximal end to a distal end of the flow control surface at a low velocity is directed towards a predetermined location in the reservoir.

34. The temperature controlled therapy system of claim 31, wherein the predetermined location is proximate the outlet of the reservoir.

* * * * *